(12) United States Patent
Appleyard et al.

(10) Patent No.: US 12,350,665 B2
(45) Date of Patent: Jul. 8, 2025

(54) CELL DIFFERENTIATION BASED ON MULTI-DIRECTIONAL LIGHT FROM A MICROFLUIDIC CHIP

(71) Applicant: ABS Global, Inc., DeForest, WI (US)

(72) Inventors: David Appleyard, Madison, WI (US); Daniel McAda, Madison, WI (US); Zheng Xia, Middleton, WI (US); James Maxwell Schiller, Madison, WI (US); Frederick Savage, Austin, TX (US); John Walker Rupel, II, Madison, WI (US); Timothy Miller, Fitchburg, WI (US); Alec Fisher, Madison, WI (US)

(73) Assignee: ABS Global, Inc., DeForest, WI (US)

( * ) Notice: Subject to any disclaimer, the term of this patent is extended or adjusted under 35 U.S.C. 154(b) by 708 days.

(21) Appl. No.: 17/696,688

(22) Filed: Mar. 16, 2022

(65) Prior Publication Data

US 2022/0297121 A1    Sep. 22, 2022

Related U.S. Application Data

(60) Provisional application No. 63/162,138, filed on Mar. 17, 2021.

(51) Int. Cl.
*B01L 3/00* (2006.01)
*A61D 19/02* (2006.01)
(Continued)

(52) U.S. Cl.
CPC ...... *B01L 3/502715* (2013.01); *A61D 19/022* (2013.01); *G01N 15/1425* (2013.01);
(Continued)

(58) Field of Classification Search
CPC ....... B01L 3/502715; B01L 2300/0663; A61D 19/022; G01N 15/1425; G01N 15/1484; G01N 2015/1402
See application file for complete search history.

(56) References Cited

U.S. PATENT DOCUMENTS

| 2011/0090500 A1 | 4/2011 | Hu et al. |
| 2017/0052105 A1 | 2/2017 | Appleyard et al. |

FOREIGN PATENT DOCUMENTS

WO    WO-2014/142924 A1    9/2014

OTHER PUBLICATIONS

International Search Report and Written Opinion in PCT/US2022/020615 dated Jul. 28, 2022 (20 pages).
(Continued)

*Primary Examiner* — Brian J. Sines
(74) *Attorney, Agent, or Firm* — Foley & Lardner LLP

(57) ABSTRACT

Disclosed is an approach to differentiating between different particle types in samples flowing through microfluidics chips. A sample may have an initial proportion of a first cell type to a second cell type. An illuminating light source may emit a coherent light at the sample, and light leaving the chip in a first direction may be detected using a first light detector, and light leaving the chip in a second direction (e.g., orthogonal to the first direction) may be detected using a second light detector. The detected light may be fluorescence. An orientational feature of a plurality of cells in the sample may be determined based on the light detected by the detectors. Based on the orientational features and the detected light, a biasing operation may be performed for each cell in the sample to obtain a modified proportion of cell types in the sample.

20 Claims, 28 Drawing Sheets

(51) Int. Cl.
*G01N 15/14* (2024.01)
*G01N 15/1434* (2024.01)

(52) U.S. Cl.
CPC ..... *G01N 15/1434* (2013.01); *G01N 15/1484* (2013.01); *B01L 2300/0663* (2013.01); *G01N 2015/1402* (2013.01)

(56) References Cited

OTHER PUBLICATIONS

Extended European Search Report on EP 22772158.6 dated Jan. 3, 2025.

1301  1302  1303

1540    1530    1520  1510a   1510

CELL DIFFERENTIATION BASED ON MULTI-DIRECTIONAL LIGHT FROM A MICROFLUIDIC CHIP

CROSS REFERENCE TO RELATED APPLICATIONS

This application claims the benefit of and priority to U.S. Patent Application No. 63/162,138, filed on Mar. 17, 2021, the contents of which are incorporated herein by reference in their entirety.

BACKGROUND

Standard flow cytometric approaches are insufficient to effectively and specifically differentiate certain particles or cell types in samples. When distinguishing different cell types, one differentiating characteristic or factor may be amount of nucleic acid found in the different cell types. But if the cells or particles have asymmetric shapes, the apparent characteristic or factor (e.g., the amount of DNA detectable using fluorescence in different cells) may vary according to a position or orientation of the cells or particles, distorting results and making comparisons less reliable. For example, the amount of DNA detectable in X-chromosome-bearing sperm cells ("female" sperm cells) is about 4 percent greater than the amount of DNA detectable in Y-chromosome-bearing sperm cells ("male" sperm cells). However, the male sperm cell may appear to have as much DNA as, more DNA than, or an otherwise insignificantly different amount of DNA from, a female sperm cell depending on the position and/or orientation of the male sperm cell when fluorescence is observed. The male sperm cell may thus appear indistinguishable from the female sperm cell, and male sperm cells may be misclassified as female sperm cells and female sperm cells may be misclassified as male sperm cells.

SUMMARY

Various embodiments relate to a method comprising: providing, to a microfluidic chip having a sample channel, a sample comprising a particle population having a proportion of a first particle type to a second particle type; emitting, from a light source, an illuminating light along a first axis such that the illuminating light coincides with particles in the sample as the sample passes through the channel; detecting, using a first light detector, a first light emitted from the sample along a first axis; detecting, using the first light detector or a second light detector, a second light emitted from the sample along a second axis; and performing, based on the detected first light emitted along the first axis and on the detected second light emitted along the second axis, a biasing operation that modifies the proportion of the first particle type to the second particle type.

In various embodiments, the first light and the second light are fluorescence (i) that results from incidence of the illuminating light on particles in the sample and (ii) that travels in multiple different directions from fluorescing particles in the sample. In various embodiments, the method further comprises: generating, based on the light emitted from the sample along the first and second axes, an intensity map of peak fluorescence associated with each particle type; detecting, based on the intensity map, a first population center associated with the first particle type, and a second population center associated with the second particle type; calculating a relative intensity along a first line passing through the first population center; calculating a slope of a second line joining the first population center and the second population center; locating a first saddle point along a third line joining a first population associated with the first particle type, and a second population associated with a second particle type; locating a second saddle point along a fourth line joining the first population, and the second population; generating a gate by bounding the first population or the second population, wherein the gate is bounded based on the first saddle point, the second saddle point, and additional bounding points. In various embodiments, the method further comprises: calculating a kernel within a pixel map; adding a first instance of the kernel to the pixel map based on the light emitted from the sample along the first and second axes; adding a second instance of the kernel to the pixel map based on the light emitted from the sample along the first and second axes; deriving a first histogram from the pixel map; removing data from the pixel map; deriving a second histogram from a first row of the pixel map; generating a first trough point from the second histogram; deriving a third histogram from a second row of the pixel map; generating a second trough point from the third histogram; and generating a polynomial function based on the first and second trough points; bounding a population based on the polynomial function and additional bounding points. In various embodiments, the method further comprises: calculating a kernel within a pixel map; adding a pre-defined number of instances of the kernel to the pixel map based on the light emitted from a plurality of samples along the first and second axes; deriving a first histogram from the pixel map along the first axis; removing data from the pixel map, based on the first histogram; generating a second histogram from the pixel map along the second axis; determining an area of interest within the pixel map, based on the second histogram; generating an additional plurality of histograms along the second axis of the area of interest of the pixel map; and determining a plurality of trough points based on the additional plurality of histograms; generating a polynomial function based on the plurality of trough points; bounding a population based on the polynomial function and additional bounding points. In various embodiments, the first axis makes an angle with respect to the second axis, and the angle is between 45 degrees and 135 degrees. In various embodiments, the angle is between 75 degrees and 105 degrees. In various embodiments, the angle is between 85 degrees and 95 degrees. In various embodiments, the first axis is orthogonal to the second axis. In various embodiments, the first axis and the second axis are along a same direction, and a beam splitter or a dichroic mirror is used to observe, using the first detector, the first and second lights based on differences in wavelength. In various embodiments, the first light is detected using the first detector situated at a first position along the first axis, and the second light is detected using the second detector situated at a second position along the second axis. In various embodiments, no more than two detectors are used to detect light emissions from the sample. In various embodiments, (i) the first light is detected using the first detector situated at a first position along the first axis, and (ii) the second light is detected using the first detector via a fiber optic element that transmits light from a second position along the second axis to the first position along the first axis. In various embodiments, the first detector comprises an avalanche photodiode with a first pixel detection region and a second pixel detection region, and the method further comprises determining, based on intensities of the first and second lights at the first and second pixel detection regions, respectively, a physical positional characteristic of each particle. In various embodiments, the biasing operation comprises emitting, using a second light source, a third light at the sample to change states of individual particles in the sample. In various embodiments, the third light is emitted to activate a particle in the sample. In various embodiments, the particle is of the first particle type, and activating the particle using the third light transforms the particle to the second particle type. In various embodiments, the second light is emitted to deactivate a particle in the sample. In various embodiments, particles in the particle population are cells, and deactivating the cells comprises ablating the cells. In various embodiments, the illuminating light coincides with the sample at a first location in a path of the sample flowing through the sample channel, and the third light is emitted at the sample so as to coincide with the sample at a second location in the path of the sample, wherein the second location is downstream of the first location. In various embodiments, the method further comprises determining an orientational feature of each particle in a set of one or more particles in the sample. In various embodiments, the orientational feature is determined based on the detected first light and on the detected second light. In various embodiments, the biasing operation is performed on each particle based on its orientational feature. In various embodiments, the particle population is a cell population, the first particle type is a first cell type, and the second particle type is a second cell type. In various embodiments, the method further comprises determining an orientational feature of each cell in the sample based on the detected first light and on the detected second light. In various embodiments, the orientational feature comprises a relative orientation of a primary surface of each cell with respect to the second axis. In various embodiments, the primary surface of each cell is a flat side of the cell or an edge side of the cell. In various embodiments, the first cell type is a male sperm cell with a Y chromosome and the second cell type is a female sperm cell without the Y chromosome. In various embodiments the second cell type is an "XY" sperm cell with an X chromosome and with a Y chromosome that would yield an XXY-type offspring. In various embodiments, the first cell type may be a desired ("target") cell type (e.g., "male" sperm cells with one Y chromosome each cell, or "female" sperm cells with one X chromosome each cell) and the second cell type may be all other cell types (e.g., "non-male" or "non-female" cell types with multiple chromosomes) that are undesired and to be eliminated or otherwise reduced proportionally or restricted. In various embodiments, the proportion, as modified by the biasing operation, comprises more male sperm cells relative to female sperm cells. In various embodiments, performing the biasing operation comprises deactivating female sperm cells in the sample. In various embodiments, the light source is a laser having a first wavelength, and the first and second lights are fluorescence with a second wavelength that is different from the first wavelength. In various embodiments, the light source is a first light source, and performing the biasing operation comprises using a second light source to emit light at the sample to change a state of particles of either the first particle type or of the second particle type in the sample. In various embodiments, the biasing operation is performed based on fluorescence detected along the first axis in combination with fluorescence detected along the second axis. In various embodiments, the method further comprises generating a histogram of intensity along the first and second axes, and identifying a region in the histogram corresponding with particles of the first type or particles of the second type. In various embodiments, the first light and the second light are fluorescence of particles in the sample, and the histogram corresponds to fluorescence intensity along the first and second axes. In various embodiments, the first light and the second light are fluorescence, and the method further comprises (i) determining an orientational feature of each particle in a set particles in the sample based on the detected first light and on the detected second light, (ii) generating a histogram of fluorescence intensity in the first and second axes, and (iii) identifying a region in the histogram corresponding with particles having a first orientational feature and particles having a second orientational feature. In various embodiments, the method is implemented on a first microfluidics system in which light is detected in multiple directions, and the method further comprises performing, on a second microfluidics system without multi-directional light detection, a second biasing operation based on the identified region. In various embodiments, the microfluidic chip further comprises an access port via which the second light emitted along the second axis is collected. In various embodiments, the access port of the microfluidic chip comprises a fiber optic element for transmitting the second set of lights. In various embodiments, the fiber optic element terminates in a beam splitting element configured to separate a fluorescence wavelength from a wavelength corresponding to the illuminating light source. In various embodiments, the method further comprises performing a gating operation based on the detected first light emitted along the first axis and on the detected second light emitted along the second axis. In various embodiments, the gating operation affects a hydrodynamic flow of the sample in the microfluidic chip. In various embodiments, the biasing operation requires both the detected first light and the detected second light in order to modify the proportion of the first particle type to the second particle type. Various embodiments relate to a product comprising the particle population having the modified proportion of the first particle type to the second particle type produced according to the method.

Various embodiments relate to a method comprising: providing a sample to a microfluidic chip having a sample channel, the sample comprising a particle population having a first proportion of a first particle type to a second particle type; emitting, using an illuminating light source, a coherent light along an illumination axis such that the coherent light coincides with the sample as the sample passes through the channel; detecting, using a first light detector at a first location along a first direction from the microfluidic chip, a first set of one or more lights at one or more wavelengths traveling from the sample in the first direction; detecting, using a second light detector at the first location or at a second location along a second direction from the microfluidic chip, a second set of one or more lights at one or more wavelengths traveling from the sample in the second direction; and performing, based on the first set of lights and the second set of lights, a biasing operation so as to obtain a modified particle population having a second proportion of the first particle type to the second particle type.

In various embodiments, the method further comprises: generating, based on the light emitted from the sample along the first and second axes, an intensity map of peak fluorescence associated with each particle type; detecting, based on the intensity map, a first population center associated with the first particle type, and a second population center associated with the second particle type; calculating a relative intensity along a first line passing through the first population center; calculating a slope of a second line joining the first population center and the second population center; locate a first saddle point along a third line joining a first population associated with the first particle type, and a second population associated with a second particle type; locate a second saddle point along a fourth line joining the first population, and the second population; generate a gate by bounding the first population or the second population, wherein the gate is bounded based on the first saddle point, the second saddle point, and additional bounding points. In various embodiments, the method further comprises: calculating a kernel within a pixel map; adding a first instance of the kernel to the pixel map based on the light emitted from the sample along the first and second axes; adding a second instance of the kernel to the pixel map based on the light emitted from the sample along the first and second axes; deriving a first histogram from the pixel map; removing data from the pixel map; deriving a second histogram from a first row of the pixel map; generating a first trough point from the second histogram; deriving a third histogram from a second row of the pixel map; generating a second trough point from the third histogram; generating a polynomial function based on the first and second trough points; bounding a population based on the polynomial function and additional bounding points. In various embodiments, the first set of lights comprises fluorescence in the first direction from particles in the sample, and the second set of lights comprises fluorescence in the second direction from particles in the sample. In various embodiments, the illuminating light incident on particles in the sample results in fluorescence of the particles in the sample. In various embodiments, the biasing operation comprises a gating operation affecting sample flow in the microfluidic chip. In various embodiments, the biasing operation comprises emitting a second coherent light at the sample. In various embodiments, the second coherent light is emitted using a second light source. In various embodiments, the second coherent light has a wavelength that is lower than the wavelength of the first coherent light. In various embodiments, the first coherent light coincides with the sample at a first location along a path of sample flow, and the second coherent light is emitted to coincide with the sample at a second location along the path that is downstream of the first location. In various embodiments, the second coherent light activates particles in the sample. In various embodiments, the second coherent light deactivates particles in the sample. In various embodiments, the first light detector is a first detection region of a detector module, and the second detector is a second detection region of the detector module. In various embodiments, the method further comprises determining, based on intensities of the first and second lights at the first and second detection regions, respectively, a physical positional characteristic of each particle. In various embodiments, the particle population is a cell population, the first particle type is a first cell type, and the second particle type is a second cell type. In various embodiments, the method further comprises determining an orientational feature of a plurality of cells in the sample. In various embodiments, the orientational feature is determined based on the detected first set of lights and on the detected second set of lights. In various embodiments, the biasing operation is performed (i) on each of the plurality of cells, and (ii) additionally based on the orientational feature of each of the plurality of cells. In various embodiments, the first cell type is a male sperm cell with a Y chromosome and the second cell type is a female sperm cell without the Y chromosome (e.g., with an X chromosome). In various embodiments, the orientational features of the plurality of cells comprise (i) a first orientation corresponding to a primary surface of cells facing the illumination access, and (ii) a second orientation corresponding to a secondary surface of cells oriented facing the illumination axis. In various embodiments, the orientational features of the plurality of cells comprise (i) a first orientation corresponding to cells oriented flat side to at least one of the first detector or the second detector, and (ii) a second orientation corresponding to cells oriented edge side to at least one of the first detector or the second detector. In various embodiments, the orientational features of the plurality of cells further comprise a third orientation corresponding to cells orientated transitionally between the edge side and flat side. In various embodiments, the second proportion is greater than the first proportion such that the modified cell population has more male sperm cells relative to female sperm cells as a result of the biasing operation. In various embodiments, performing the biasing operation comprises deactivating one or more cells of the first cell type or of the second cell type in the sample. In various embodiments, the first set of lights comprises at least one of light scatter or fluorescence in the first direction, and the second set of lights comprises at least one of light scatter or fluorescence in the second direction. In various embodiments, the illuminating light source is a laser having a first wavelength, and the fluorescence has a second wavelength that is different from the first wavelength. In various embodiments, performing the biasing operation comprises changing a state of one or more particles of the first particle type or of the second particle type in the sample. In various embodiments, the biasing operation is performed based on fluorescence detected in the first direction in combination with fluorescence detected in the second direction. In various embodiments, the biasing operation is performed based on (i) fluorescence in the first direction, and on (ii) both light scatter and fluorescence in the second direction. In various embodiments, the method further comprises generating a histogram of fluorescence intensity in the first and second directions, and identifying a region in the histogram corresponding with particles of the first cell type or particles of the second cell type. In various embodiments, the method further comprises generating a histogram of fluorescence intensity in the first and second directions, and identifying a region in the histogram corresponding with particles having a first orientational feature and particles having a second orientational feature. In various embodiments, the method further comprises generating a histogram of fluorescence intensity in the first and second directions, and identifying a region in the histogram corresponding with at least one of (i) particles of the first cell type, (ii) particles of the second cell type, (iii) particles having a first orientational feature, or (iv) particles having a second orientational feature. In various embodiments, the method is implemented on a first microfluidics system in which light is detected in multiple directions, and the method further comprises performing, on a second microfluidics system without multi-directional light detection, a second biasing operation based on the identified region. In various embodiments, the first direction is along the illumination axis, and the second direction is along a second axis that is angled with respect to the illumination axis. In various embodiments, the second direction is orthogonal to the illumination axis. In various embodiments, the second direction is at an angle with respect to the illumination axis, and the angle is between 45 degrees and 135 degrees. In various embodiments, the microfluidic chip further comprises an access port via which the second set of lights is collected. In various embodiments, the access port of the microfluidic chip comprises a fiber optic element for transmitting the second set of lights. In various embodiments, the fiber optic element terminates in a beam splitting element configured to separate a fluorescence wavelength from a wavelength corresponding to the illuminating light source. In various embodiments, the method further comprises filtering a third set of lights from a second illuminating light source. In various embodiments, the filtering further comprises filtering by an optical fiber defined by a length having a curvilinear shape. In various embodiment, filtering may be wavelength-based (e.g., by usage of embedded Bragg grating) and/or spatial-based (e.g., based on position and/or numeral aperture (NA)) of a fiber. In various embodiments, the method further comprises determining a deactivation of a particle in the sample based on detecting a characteristic of the third set of lights. In various embodiments, the method further comprises changing, based on the modified cell population, at least one of (i) the microfluidic chip or (ii) a manner in which the sample is provided to the microfluidic chip so as to obtain a third proportion of the first particle type to the second particle type. In various embodiments, the method further comprises collecting the sample via the channel following the biasing operation. Various embodiments relate to a product comprising the modified particle population having the second proportion of the first particle type to the second particle type produced according to the method.

Various embodiments relate to a flow cytometry system comprising: an illuminating light source configured to emit coherent light that has a first wavelength and that coincides with a sample channel of a microfluidic chip; a first light detector that is configured to detect light traveling from the sample channel in a first direction; a second light detector that is configured to detect light traveling from the sample channel in a second direction; and a control unit configured to: (i) illuminate a sample passing through the sample channel of the microfluidic chip, the sample comprising a cell population with a first proportion of a first cell type to a second cell type, (ii) detect a first light using the first light detector and a second light using the second light detector, and (iii) control one or more biasing mechanisms to perform, based on both the first light detected using the first light detector and the second light detected using the second light detector, a biasing operation to modify the cell population to obtain a second proportion of the first cell type to the second cell type.

In various embodiments, the system further comprises the microfluidic chip, wherein the microfluidic chip comprises an access port with a fiber optic element through which the second light travels to reach the second detector. In various embodiments, the first direction is an illumination axis of the illuminating light source and the second detector is positioned to detect light that is at an angle with respect to the illumination axis. In various embodiments, the angle is between 45 degrees and 135 degrees. In various embodiments, the first direction is an illumination axis of the illuminating light source and the second detector is positioned to detect light that travels orthogonally to the illumination axis. In various embodiments, the one or more biasing mechanisms comprises a second laser having a higher intensity or lower wavelength relative to the illuminating laser, and the control unit is further configured to use the second laser to deactivate one or more cells of the first cell type or of the second cell type in the sample. In various embodiments, the one or more biasing mechanisms comprises an actuator affecting sample flow in the microfluidic chip. In various embodiments, the control unit is configured to perform the biasing operation based on forward fluorescence detected using the first detector and side fluorescence detected using the second detector. In various embodiments, the control unit is further configured to generate a histogram of fluorescence intensity in the first and second directions. In various embodiments, the control unit is further configured to identify a region in the histogram corresponding with at least one of (i) particles of the first cell type, (ii) particles of the second cell type, (iii) particles having a first orientational feature, or (iv) particles having a second orientational feature. In various embodiments, the control unit is further configured to control, based on the identified region, the one or more biasing mechanisms to perform, using only detected light traveling in the first direction not the second direction, a second biasing operation for a second sample.

Various embodiments relate to a method that comprises providing a sample to a microfluidic chip having a sample channel. The sample may comprise a population having a first proportion of a first particle type to a second particle type. For example, the sample may comprise a cell population having a first proportion of a first cell type to a second cell type. An illuminating light source may be used to provide a coherent light along an illumination axis. The coherent light may be provided such that the coherent light coincides with the sample as the sample passes through the channel. A first light detector may be used to detect a first set of one or more lights at one or more wavelengths. The first set of lights may be detected in a first direction (e.g., along the illumination axis) from the microfluidic chip. The first light detector may be positioned or situated at a first location with respect to, for example, the microfluidic chip or the illuminating light source. A second light detector may be used to detect a second set of one or more lights at one or more wavelengths. The second set of lights may be detected in a second direction (that is angled with respect to the first direction) from the microfluidic chip. The second light detector may be positioned or situated at a second location with respect to, for example, the microfluidic chip or with respect to the microfluidic chip or the illuminating light source. A biasing operation may be performed. The biasing operation may be performed based at least in part on the first set of lights and the second set of lights. The biasing operation may be performed so as to obtain, for example, a modified cell population. The modified cell population may have a second proportion of the first cell type to the second cell type. The second proportion may be higher or lower than the first population.

In various embodiments, one or more orientational features and/or one or more positional features of a plurality of cells or other particles in the sample (e.g., each cell traveling in the sample channel) may be determined.

In various embodiments, orientational features and/or positional features may be determined based on, for example, the detected first set of lights and the detected second set of lights.

In various embodiments, the biasing operation may be performed on each of the plurality of cells. The biasing operation may be based on one or more orientational features and/or positional features of each of the plurality of cells.

In various embodiments, the first cell type may be a male sperm cell with a Y chromosome. The second cell type may be, for example, a female sperm cell with an X chromosome, or otherwise without a single Y chromosome. The second cell type may be, for example, a sperm cell with an X and with a Y chromosome which may be an "XY" sperm cell.

In various embodiments, orientational features of the plurality of cells may comprise a first orientation corresponding to cells oriented flat side to at least one of the first detector or the second detector. The orientational features may comprise a second orientation corresponding to cells oriented edge side to at least one of the first detector or the second detector. The orientational features may comprise a third orientation corresponding to cells orientated transitionally between the edge side and flat side.

In various embodiments, the second proportion may be greater than the first proportion such that the modified cell population has more male sperm cells relative to female sperm cells as a result of the biasing operation.

In various embodiments, the first set of lights may comprise light scatter and/or fluorescence in the first direction. The second set of lights may comprise light scatter and/or fluorescence in the second direction. In certain embodiments, the first and second sets of lights are fluorescence emitted in two different directions.

In various embodiments, the illuminating light source may be a laser having a first wavelength. The fluorescence may have a second wavelength that is different from the first wavelength.

In various embodiments, performing the biasing operation may comprise ablating, deactivating, or otherwise changing the state of one or more cells (or other particles) of the first cell type and/or of the second cell type in the sample. Particle states may be changed using emissions from a light source. For example, cells may be ablated using emissions from an ablative light source, which may have a higher intensity and/or different wavelength (e.g., lower wavelength) than the illuminating light source. The ablative light source may have a different fluence (e.g., intensity/area) than a detection or non-ablative light source. The light source may deactivate or "kill" cells or other particles in the sample.

In various embodiments, the biasing operation may be performed based on fluorescence detected in the first direction in combination with fluorescence detected in the second direction.

In various embodiments, the biasing operation may be performed based on (i) fluorescence in the first direction, and on (ii) both light scatter and fluorescence in the second direction.

In various embodiments, a histogram of fluorescence intensity in the first and second directions may be generated. A region in the histogram corresponding with particles (e.g., cells) of the first particle type (e.g., first cell type) or particles (e.g., cells) of the second particle type (e.g., second cell type) may be identified.

In various embodiments, a histogram of fluorescence intensity in the first and second directions may be generated. A region in the histogram corresponding with particles (e.g., cells) having a first orientational feature and particles (e.g., cells) having a second orientational feature may be identified.

In various embodiments, the method may be implemented on a first microfluidics system in which light is detected in multiple directions (e.g., using first and second detectors at first and second positions, respectively). What is learned may subsequently be applied to microfluidics system without multi-directional light detection. In various embodiments, a second biasing operation may be performed based on the identified region on a second microfluidics system without multi-directional light detection. The identified region may serve as a guide that indicates expected particle or cell type based on light from a single detector.

In various embodiments, the first direction may be along the illumination axis, and the second direction may be along a second axis that is angled with respect to the illumination axis.

In various embodiments, the second direction may be orthogonal to the illumination axis.

In various embodiments, the second direction may be at an angle with respect to the illumination axis. The angle may be, for example, between 85 degrees and 95 degrees, or between 80 degrees and 100 degrees, or between 75 and 105 degrees, or between 70 degrees and 110 degrees, or between 65 degrees and 115 degrees, or between 60 and 120 degrees, or between 55 degrees and 125 degrees, or between 50 degrees and 130 degrees, or between 45 and 135 degrees, or between 30 degrees and 150 degrees.

In various embodiments, the microfluidic chip may further comprise an access port via which the second set of lights is collected.

In various embodiments, an access port of the microfluidic chip may comprise one or more fiber optic elements. The fiber optic elements may transmit the second set of lights to, for example, the second detector.

In various embodiments, the fiber optic element may terminate in a beam splitting element. The beam-splitting element may be configured to separate a fluorescence wavelength from a wavelength corresponding to the illuminating light source.

In various embodiments, a third set of lights may be filtered from a second illuminating light source.

In various embodiments, the filtering may comprise filtering by an optical fiber defined by a length having a curvilinear shape.

In various embodiments, a deactivation of a cell in the sample may be determined based on the third set of lights.

In various embodiments, based on the modified cell population, at least one of (i) the microfluidic chip or (ii) a manner in which the sample is provided to the microfluidic chip may be changed to, for example, obtain a third proportion of the first cell type to the second cell type.

In various embodiments, the sample may be collected via the channel following the biasing operation.

Various embodiments relate to a product comprising the modified particle population having the second proportion of the first particle type to the second particle type produced according to the method discussed above.

Various embodiments relate to a flow cytometry system. The system may comprise an illuminating light source that may be configured to emit coherent light that has a first wavelength and that coincides with a sample channel of a microfluidic chip. The system may comprise a first light detector that is configured to detect light traveling from the sample channel in a first direction. The system may comprise a second light detector that is configured to detect light traveling from the sample channel in a second direction. The system may comprise a control unit. The control may be configured to illuminate a sample passing through the sample channel of the microfluidic chip. The sample may comprise a cell population (or other particle population) with a first proportion of a first cell type (or a first particle type) to a second cell type (or a second particle type). The control unit may be configured to use the first light detector to detect a first light and use the second light detector to detect a second light. The control unit may control a biasing mechanism to perform a biasing operation. The biasing operation may be based on both the first light detected using the first light detector and the second light detected using the second light detector. The biasing operation may be performed to modify the cell population (or particle population) to obtain a second proportion of the first cell type (or the first particle type) to the second cell type (or the second particle type).

In various embodiments, the system may comprise the microfluidic chip. The microfluidic chip may comprise an access port. The access port may comprise a fiber optic element through which the second light travels to reach the second detector.

In various embodiments, the first direction may be an illumination axis of the illuminating light source. The second detector may be positioned to detect light that is at an angle with respect to the illumination axis. The angle may be between 75 and 105 degrees, or between 60 and 120 degrees, or between 45 and 135 degrees, or between 30 degrees and 150 degrees. The angle may be substantially 90 degrees, such that the second detector detects light that travels orthogonally to the illumination axis.

In various embodiments, the biasing mechanism may comprise a second light source, which may be an ablation laser or other deactivating light source. The control unit may be configured to use the ablation laser or other deactivating light source to ablate or otherwise deactivate one or more cells of the first cell type or of the second cell type in the sample (or otherwise to ablate or deactivate one or more particles of the first particle type or of the second particle type in the sample). The biasing mechanism may (alternatively or additionally to the ablation laser or deactivating light source) include one or more activating light sources that may be controlled by the control unit to, for example, activate particles in the sample based on detected light.

In various embodiments, the control unit may be configured to perform the biasing operation based on "forward" fluorescence detected using the first detector and "side" fluorescence detected using the second detector. In various embodiments, the control unit may be configured to perform the biasing operation based on a first fluorescence detected using a first detector and a second fluorescence using the second detector. The first fluorescence and the second fluorescence may each be a fluorescence detected from one direction. The first fluorescence and the second fluorescence may be fluorescences detected from different directions. In various embodiments, the disclosed axes may be "flipped" with respect to each other, such that, for example, either detector could be labeled the "first" detector or the "second" detector, and similarly, either direction may be the "forward" direction or the "side" direction.

Various embodiments relate to a microfluidic chip. The chip may comprise a sample channel extending from a sample inlet to a sample outlet. The chip may be configured to receive a sample comprising a cell population (or other particle population). The chip may comprise an access port extending from an opening in the microfluidic chip to the sample channel. The chip may comprise a fiber optic element that is situated in the access port and is configured to transmit wavelengths of light having wavelengths corresponding to at least one of light scatter and fluorescence from a sample passing through the sample channel. The microfluidic chip may be configured for illumination of the sample using an illumination laser along an illumination axis. The chip may be configured for collection of light emitted co-axially to the illumination axis. The fiber optic element may be configured to collect light emitted orthogonally from cells illuminated using the illumination laser. An orientational feature of a cell in the cell population of the sample may be derivable from light collected by the fiber optic element and from light collected co-axially to the illumination axis.

In various embodiments, the chip may comprise a beam splitting element configured to separate fluorescence wavelengths of light from scatter wavelengths of light transmitted through the fiber optic element.

In various embodiments, the orientational feature of the cell in the cell population of the sample is a relative orientation of a primary surface of the particle to the illumination axis.

Various embodiments relate to a product comprising a modified cell population having a modified proportion of a first cell type to a second cell type produced according to a specific method. The method may comprise providing a sample to a microfluidic chip having a sample channel. The sample may comprise a cell population having an initial proportion of the first cell type to the second cell type. The method may comprise emitting, using an illuminating light source, a coherent light along an illumination axis such that the coherent light coincides with the sample as the sample passes through the channel. The method may comprise detecting, in a first direction from the microfluidic chip and at a first location, using a first light detector at the first location, a first set of one or more lights at one or more wavelengths. The method may comprise detecting, in a second direction from the microfluidic chip and at a second location, using a second light detector at the second location, a second set of one or more lights at one or more wavelengths. The method may comprise determining a position and/or an orientation for each cell in the sample based on the detected first set of lights and the detected second set of lights. The method may comprise performing a biasing operation so as to obtain the modified cell population having the modified proportion of the first cell type to the second cell type. The biasing operation may be performed based on the first set of lights, the second set of lights, and/or the determined orientation and/or position.

In various embodiments, the first cell type may be a male sperm cell with a Y chromosome and the second cell type may be a female sperm cell without the Y chromosome.

In various embodiments, the modified proportion may be greater than the initial proportion such that the modified cell population has more male sperm cells relative to female sperm cells as a result of the biasing operation.

In various embodiments, the first set of lights may comprise at least one of light scatter or fluorescence in the first direction, and the second set of lights may comprise at least one of light scatter or fluorescence in the second direction.

In various embodiments, the illuminating light source may be a laser having a first wavelength, and the fluorescence may have a second wavelength that is different from the first wavelength.

In various embodiments, performing the biasing operation may comprise ablating one or more cells of the first cell type or of the second cell type in the sample.

In various embodiments, the biasing operation may be performed based on fluorescence detected in the first direction in combination with fluorescence detected in the second direction.

In various embodiments, the biasing operation may be performed based on (i) fluorescence in the first direction, and on (ii) both light scatter and fluorescence in the second direction.

In various embodiments, the method may comprise generating a histogram of fluorescence intensity in the first and second directions, and identifying a region in the histogram corresponding with cells of the first cell type or cells of the second cell type.

In various embodiments, the first direction may be along the illumination axis, and the second direction may be along a second axis that is angled with respect to the illumination axis.

In various embodiments, the second direction may be orthogonal to the illumination axis.

In various embodiments, the second direction may be at an angle with respect to the illumination axis. The angle may be between 75 and 105 degrees, or between 60 and 120 degrees, or between 45 and 135 degrees, or between 30 degrees and 150 degrees.

In various embodiments, the microfluidic chip may comprise an access port via which the second set of lights is collected.

In various embodiments, the access port of the microfluidic chip may comprise a fiber optic element for transmitting the second set of lights.

In various embodiments, the fiber optic element may terminate in a beam splitting element configured to separate a fluorescence wavelength from a wavelength corresponding to the illuminating light source.

In various embodiments, the method may comprise filtering a third set of lights from a second illuminating light source.

In various embodiments, the filtering may comprise filtering by an optical fiber defined by a length having a curvilinear shape.

In various embodiments, the method may further comprise determining a deactivation of a cell in the sample based on the third set of lights.

In various embodiments, the method may further comprise filtering a third set of lights from a second illuminating light source.

Various embodiments relate to a method comprising emitting, using an illuminating light source, a coherent light along an illumination axis such that the coherent light coincides with a sample as the sample passes through a sample channel of a microfluidic chip. The sample may comprise a cell population having a first proportion of a first cell type to a second cell type. A first light detector at a first location may be used to detect, in a first direction (e.g., along or parallel to the illumination axis) from the microfluidic chip, a first set of one or more lights at one or more wavelengths. A second light detector at a second location may be used to detect, in a second direction (e.g., an axis that is angled with respect to the first direction) from the microfluidic chip, a second set of one or more lights at one or more wavelengths. An orientational feature of a plurality of cells in the sample may be determined based on the first set of lights and the second set of lights. A biasing operation may be performed so as to obtain a modified cell population having a second proportion of the first cell type to the second cell type. The biasing operation may be performed based on (i) the orientational features of the plurality of cells and (ii) at least one of the first set of lights or the second set of lights.

In various embodiments, the first cell type may be a male sperm cell with a Y chromosome and the second cell type is a female sperm cell without the Y chromosome.

In various embodiments, the second proportion may be greater than the first proportion such that the modified cell population has more male sperm cells relative to female sperm cells as a result of the biasing operation.

In various embodiments, the orientational features of the plurality of cells may comprise (i) a first orientation corresponding to cells oriented flat side to at least one of the first detector or the second detector, and (ii) a second orientation corresponding to cells oriented edge side to at least one of the first detector or the second detector.

In various embodiments, the orientational features of the plurality of cells may comprise a third orientation corresponding to cells orientated transitionally between the edge side and flat side.

In various embodiments, the first set of lights may comprise at least one of light scatter or fluorescence in the first direction, and the second set of lights may comprise at least one of light scatter or fluorescence in the second direction.

In various embodiments, the illuminating light source may be a laser having a first wavelength, and the fluorescence may have a second wavelength that is different from the first wavelength.

In various embodiments, the performing the biasing operation may comprise ablating one or more cells of the first cell type or of the second cell type in the sample.

In various embodiments, the biasing operation may be performed based on fluorescence detected in the first direction and fluorescence detected in the second direction.

In various embodiments, a histogram of fluorescence intensity in the first and second directions may be generated. In various embodiments, the histogram is a two-dimensional (2D) histogram that combines information from both detectors (as opposed to a pair of one-dimensional (1-D) histograms for independent detectors). A first region in the histogram corresponding with cells of the first cell type or cells of the second cell type may be identified. Alternatively or additionally, a second region in the histogram corresponding to cells having a first orientational feature may be identified, and a third region corresponding to cells having a second orientational feature may be identified.

In various embodiments, a histogram of fluorescence intensity in the first direction may be generated and a histogram of fluorescence intensity in the second direction may be generated. A first histogram may be generated based upon fluorescence detected by a first detector and a second histogram may be generated based upon fluorescence detected by a second detector. In various embodiments, a first and a second histogram may be combined or overlaid to generate a combined histogram comprising fluorescence information detected from a first and a second direction, or from a first and a second detector.

In certain example embodiments, a proportion of first to second particle types is modified by a biasing operation. In a hypothetical, if a sample includes 1000 cells (or other particles), with 450 (45%) a first type (e.g., "female"), 450 (45%) a second type ("male"), and 100 (10%) a third type (e.g., dead cells), there would be a sample with a proportion of 450 to 450 first type to second type (e.g., male to female), or a 1:1 ratio. Following a biasing operation that tends to ablate, kill, or otherwise inactivate the first type (e.g., female cells) in a sample that includes the first and second types (e.g., female and male cells), for example, that could yield 100 (10%) female cells, 400 (40%) male cells, and 500 (50%) dead cells. The new (modified) proportion of first to second cell types in this hypothetical case would be 100 female to 400 male, or a 1:4 ratio. Another hypothetical biasing operation might leave yield 50 female, 500 male, 150 dead, and 300 of a fourth type (e.g., "neutered"). Here, the modified proportion would be 50 female to 500 male, or 1:10. In yet another hypothetical, if zero female cells are left, the modified proportion would be 0:1. Accordingly, in various embodiments, even though there could be a different mix of particle types (e.g., types of cells), the proportion can be changed such that a particular type is proportionally higher or lower after biasing as compared to before biasing.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
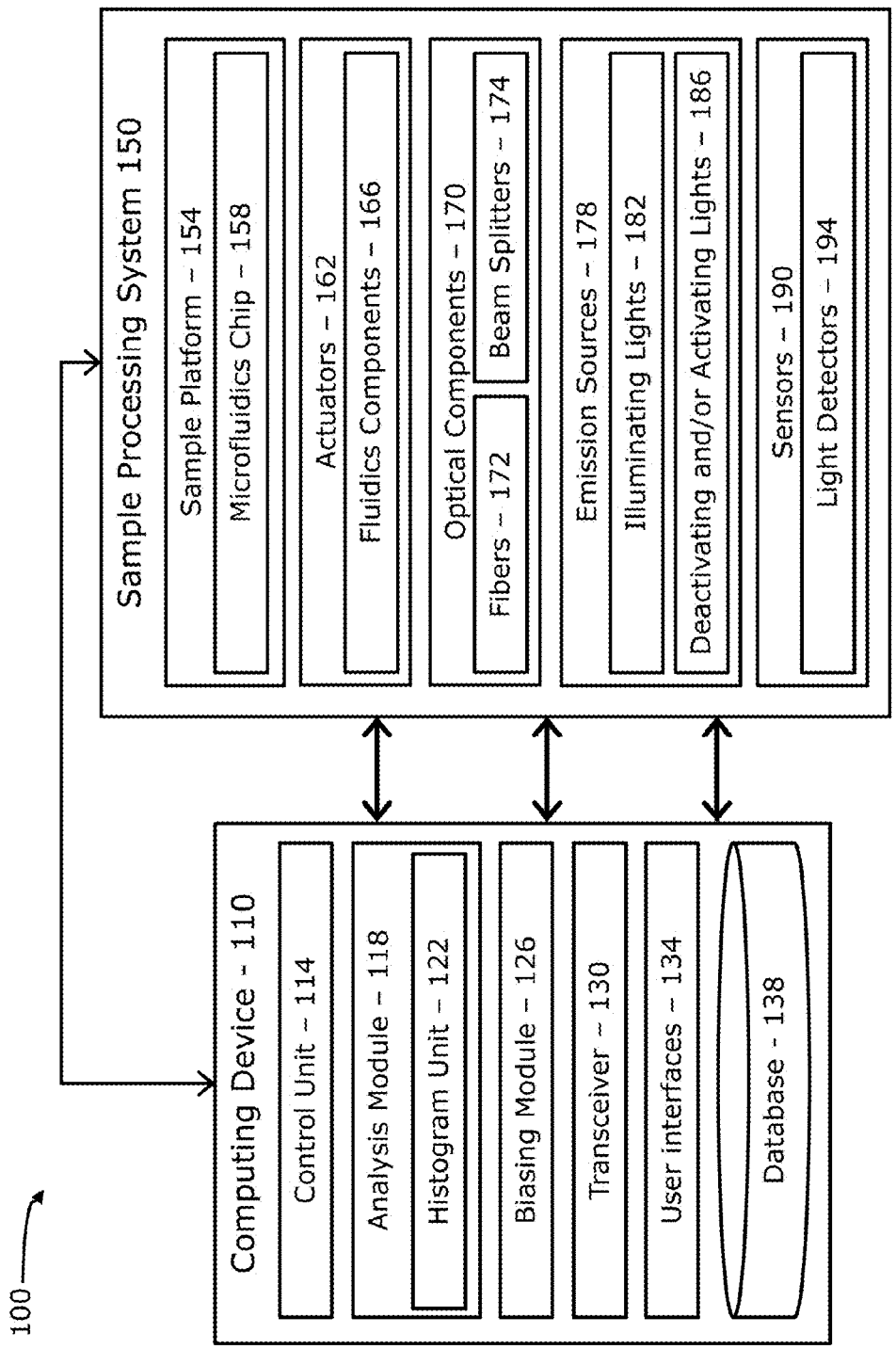
FIG. 1 depicts a microfluidics system that includes a computing device and a sample processing system according to various potential embodiments.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and make part of this disclosure.

Various embodiments provide applications for skewing a particle population in a sample to favor a first particle type or a second particle type. The particles may be cellular or molecular. A biasing operation may, for example, be employed to select for certain particles or cells, such as by deactivating selected particles, activating selected particles, ablating, slicing, photodamaging cells or otherwise rendering cells nonfunctional, and/or physically separating components of a sample. The effectiveness of biasing operations may depend on knowing an orientation or position of particles. For example, a cell may be illuminated so as to excite fluorophore-tagged components of the cell to thereby give rise to detectable fluorescence. The intensity of fluorescence may be deemed to correspond with a characteristic of the cell. In such a case, an area of a detection surface (i.e., the surface being hit by excitation light) may positively correlate with fluorescence intensity such that the greater the surface area, the greater the excitation and thus the greater the fluorescence. If the cell is irregularly-shaped or otherwise non-symmetrical, it may effectively have multiple "surfaces" (i.e., the area of the detection surface may vary), such as a primary surface with the relatively greatest area, a tertiary surface with the relatively smallest area, and a secondary surface with an area in between the areas of the primary and tertiary surface.

In an example, a sample may include semen with both male and female sperm cells, and a sexed semen product that is predominantly Y-chromosome-bearing ("Y-skew") may be desired. Standard flow cytometric approaches have been insufficient to effectively specifically differentiate Y-chromosome-bearing sperm cells for the production of a Y-skew sexed semen product. In particular, the relative shape and overlap of X- and Y-chromosome-bearing sperm cells as depicted on a histogram of fluorescence intensity (i.e., the observable about 4 percent difference in chromosomal DNA stained with a fluorescent DNA dye (e.g., Hoechst 33342 dye) between male and female sperm cells) under typical flow cytometer operation (i.e., single detector oriented coaxially with the detection laser beam) does not permit the Y-chromosome peak to be as effectively differentiated from the X-chromosome peak to a sufficient extent to enhance the ability to eliminate the X-chromosome bearing sperm cells at the high throughputs and skew rates that are associated with commercially viable products. Based on a combination of light detected in multiple directions, position and/or orientation of cells or other particles may be identified and accounted-for in distinguishing between different cell types. For example, in various embodiments, a fiber optic may be integrated into a microfluidic chip to gather emitted light in a direction that is, for example, orthogonal to (or otherwise angled with respect to) the illumination laser axis (and also potentially orthogonal or otherwise angled with respect to the direction of sample flow). Such a fiber optic facilitates gathering of side fluorescence and side scatter data from the cells. Identifying regions on a two-dimensional histogram helps to more effectively distinguish between different orientations and particle types.

Referring to FIG. 1, in various embodiments, a microfluidics system 100 may include a computing device 110 (or multiple computing devices, co-located or remote to each other) and a sample processing system 150. In various embodiments, computing device 110 (or components thereof) may be integrated with the sample processing system 150 (or components thereof). The sample processing system 150 may include a sample platform 154, which may receive a microfluidics chip 158 that receives a sample through a sample channel. The delivery and movement of samples may be controlled by actuators 162 that include fluidics components 166 that control fluid flow or reposition optical components. Optical components 170 may include optical fibers 172, beam splitters 174, or other components (e.g., optical filters, mirrors, and lenses) for receiving, separating, combining, delivering, transmitting, focusing, defocusing, collimating, or guiding light emissions. As used herein, "guiding" may include focusing, defocusing, and/or collimating operations with respect to various beams of light. Emissions sources 178 may include various sources of light at different wavelengths and power levels, such as illuminating lights 182 (e.g., an excitation laser) and deactivating and/or activating lights 186 (e.g., a "kill" laser). Sample processing system 150 includes sensors 190, such as a set of light detectors 194 situated at various positions. Sensors 190 may detect light scatter (e.g., light that hits a sample and is scattered in various directions) and fluorescence light (e.g., light emitted, upon excitation by one of the emissions sources 178, by fluorophores in cells or other particles in samples).

The computing device 110 (or multiple computing devices) may be used to control, and receive signals acquired via, components of sample processing system 150 (e.g., light detected using light detectors 194). The computing device 110 may include one or more processors and one or more volatile and non-volatile memories for storing computing code and data that are captured, acquired, recorded, and/or generated. The computing device 110 may include a control unit 114 that is configured to exchange control signals with sample platform 154, actuators 162, optical components 170, emission sources 178, and/or sensors 190, allowing the computing device 110 to be used to control, for example, delivery of samples, illumination with light, detection and performance of biasing operations. An analysis module 118 may be used to perform computations on and analyses of data captured using sample processing system 150, and may include, for example, a histogram unit 122 that may generate and process histograms. A biasing module 126 may identify and perform operations based on light detected using sensors 190, such as by controlling actuators 162 (to, e.g., perform gating operations that affect sample flow or reorient light sources to affect aim of the light emitted by the light sources) and/or emission sources 178 (to, e.g., emit light that activates or deactivates particles).

A transceiver 130 allows the computing device 110 to exchange readings, control commands, and/or other data with sample processing system 150 (or components thereof). One or more user interfaces 134 allow the computing device 110 to receive user inputs (e.g., via a keyboard, touchscreen, microphone, camera, etc.) and provide outputs (e.g., via display screen, audio speakers, etc.). The computing device 110 may additionally include one or more databases 138 for storing, for example, signals acquired via one or more sensors 190, histograms generated, etc. In some implementations, database 138 (or portions thereof) may alternatively or additionally be part of another computing device that is co-located or remote and in communication with computing device 110 and/or sample processing system 150 (or components thereof).

Figure 2:
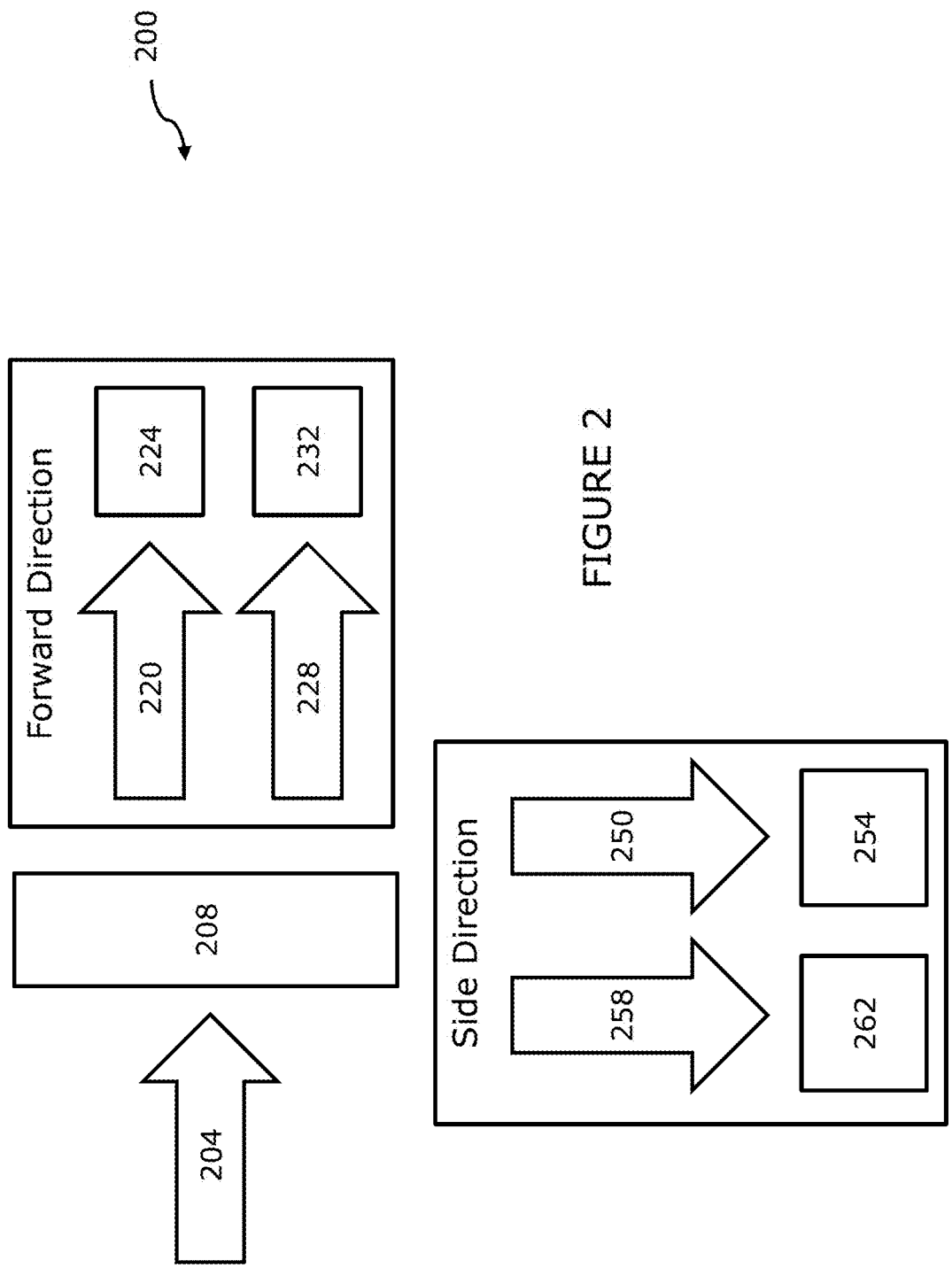
FIG. 2 represents an example configuration for components of a sample processing system according to various potential embodiments.

Referring to FIG. 2, an example configuration 200 is represented. Laser light 204 may be emitted at a microfluidics chip 208. In a forward direction (e.g., in a first direction that may be along an illumination axis), laser scatter 220 and fluorescence 228 may be received from the chip 208. The laser scatter 220 may be detected using a forward scatter ("FS") detector 224, and the fluorescence 228 may be detected using a forward fluorescence ("FF") detector 232. In a side direction (e.g., in a second direction that may be substantially orthogonal to, or otherwise at an angle with respect to, the first direction), laser scatter 250 and fluorescence 258 may be received from the chip 208. The laser scatter 250 may be detected using a side scatter ("SS") detector 254, and the fluorescence 258 may be detected using a side fluorescence ("SF") detector 262.

Figure 3:
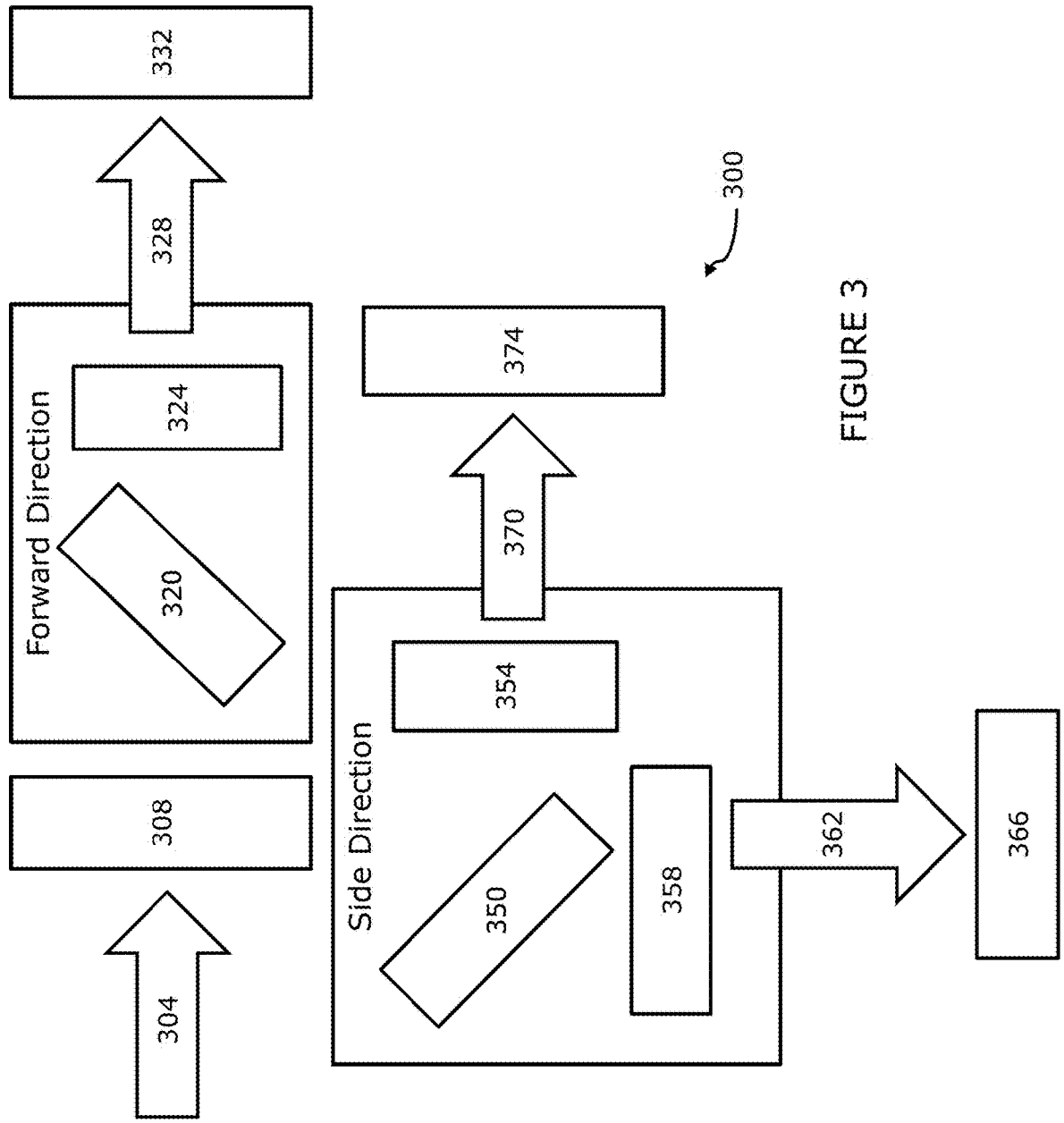
FIG. 3 represents another example configuration for components of a sample processing system according to various potential embodiments.

Referring to FIG. 3, an example configuration 300 shows separation of side fluorescence and side scatter signals in a multi-side detector arrangement that includes a dichroic (e.g., single laser dichroic Z355rdc from Chroma Technology Corp.). Laser light 304 reaches microfluidics chip 308, and in a forward direction, a dichroic 320 and filter 324 (e.g., a long wave pass filter, such as Colored-Glass Alternative CGA-395 filter from Newport Corp.) may be used to obtain fluorescence 328, which may be received at FF avalanche photodiode (APD) 332. In a side direction, dichroic 350 may be used to obtain fluorescence 362 and laser scatter 370. Filter 354 (e.g., 360LP low-pass mask aligner filter from Omega Optical, LLC) may be used to filter laser scatter 370 that is received at SS photomultiplier tube (PMT) 374, and filter 358 (e.g., a 360/23 band-pass filter) may be used to filter fluorescence 362 that is received at SF PMT 366.

Figure 4:
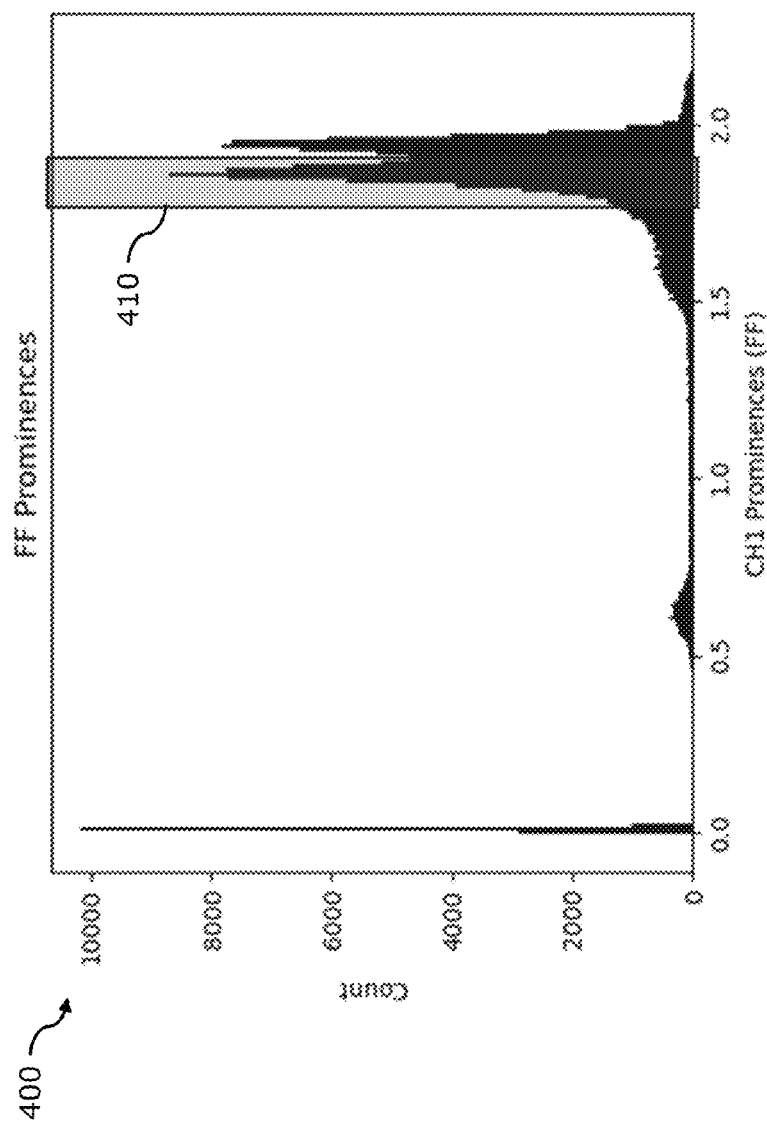
FIG. 4 depicts forward fluorescence data acquired using a single-detector sample processing system according to various potential embodiments.

FIG. 4 represents a single detector (one-dimensional) histogram 400 obtained based on forward fluorescence (FF) alone (i.e., no light detected from a second direction) depicting an attempt to identify cell types in a cell population. FIG. 4 represents number of cells versus forward fluorescence ("CH1 Prominences") for a sample, and shows two peaks, with the lower-intensity peak on the left-hand side and the higher-intensity peak on the right-hand side. Cells with relatively less DNA (e.g., male sperm cells) would be expected to correspond to the left-hand peak, and cells with relatively more DNA (e.g., female sperm cells) would be expected to correspond to the right-hand peak. But, the heads of sperm cells have a disk-like shape, and may be oriented such that fluorescence may be received from the wider flat face or "primary surface" (such that fluorescence has the relatively highest intensity that is detected from the sperm cell), the narrower edge or "tertiary surface" (such that fluorescence has the relatively lowest intensity that is detected from the sperm cell), or a transitional orientation between the flat face and the edge or "secondary surface" (such that fluorescence has an intensity between the higher flat-face intensity and the lower edge intensity). As a result, unless all cells are oriented to have the same orientation when fluorescence is detected (i.e., unless the area of the detection surface remains fairly constant), some female cells may be observed at intensities otherwise expected for male cells (thus falling in the left-hand peak), and some male cells may be observed at intensities otherwise expected for female cells (thus falling in the right-hand peak). In the one-detector setup of FIG. 4, the cells falling in region 410 may be deemed to be male or other targeted cells (and cells falling outside of region 410 may be deactivated for not being targeted cells, such as female cells), although some targeted (male) cells may have fallen outside of region 410, and some not-targeted (female) cells may have fallen within region 410.

Figure 5:
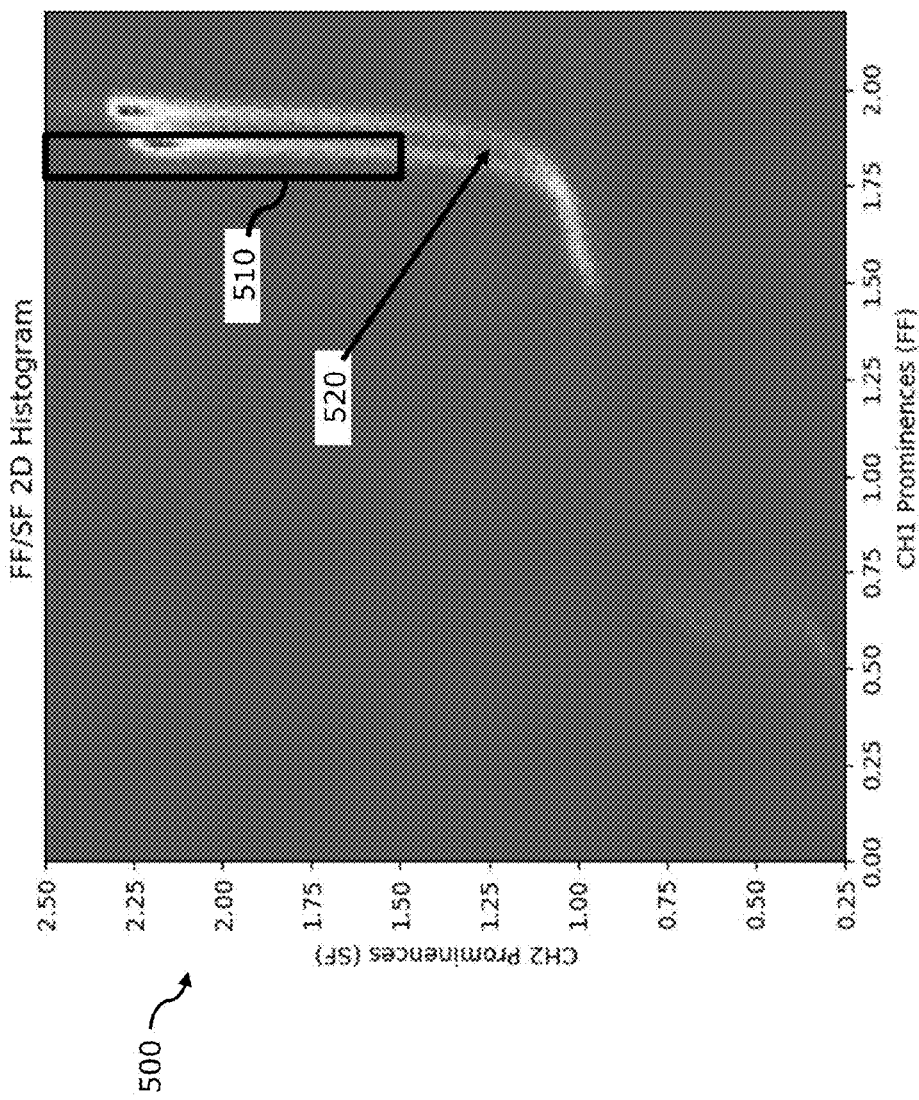
FIG. 5 depicts a histogram of forward fluorescence and side fluorescence acquired using a dual-detector sample processing system according to various potential embodiments.
Figure 6:
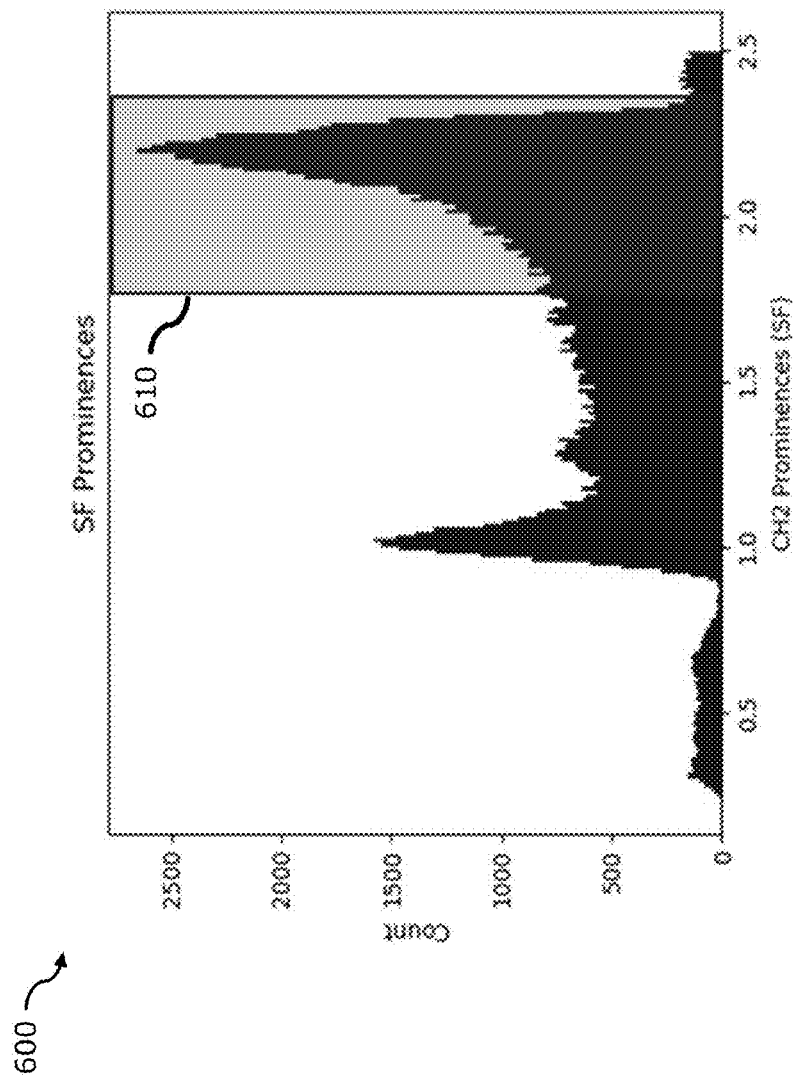
FIG. 6. depicts side fluorescence data acquired using a sample processing system according to various potential embodiments.
Figure 7:
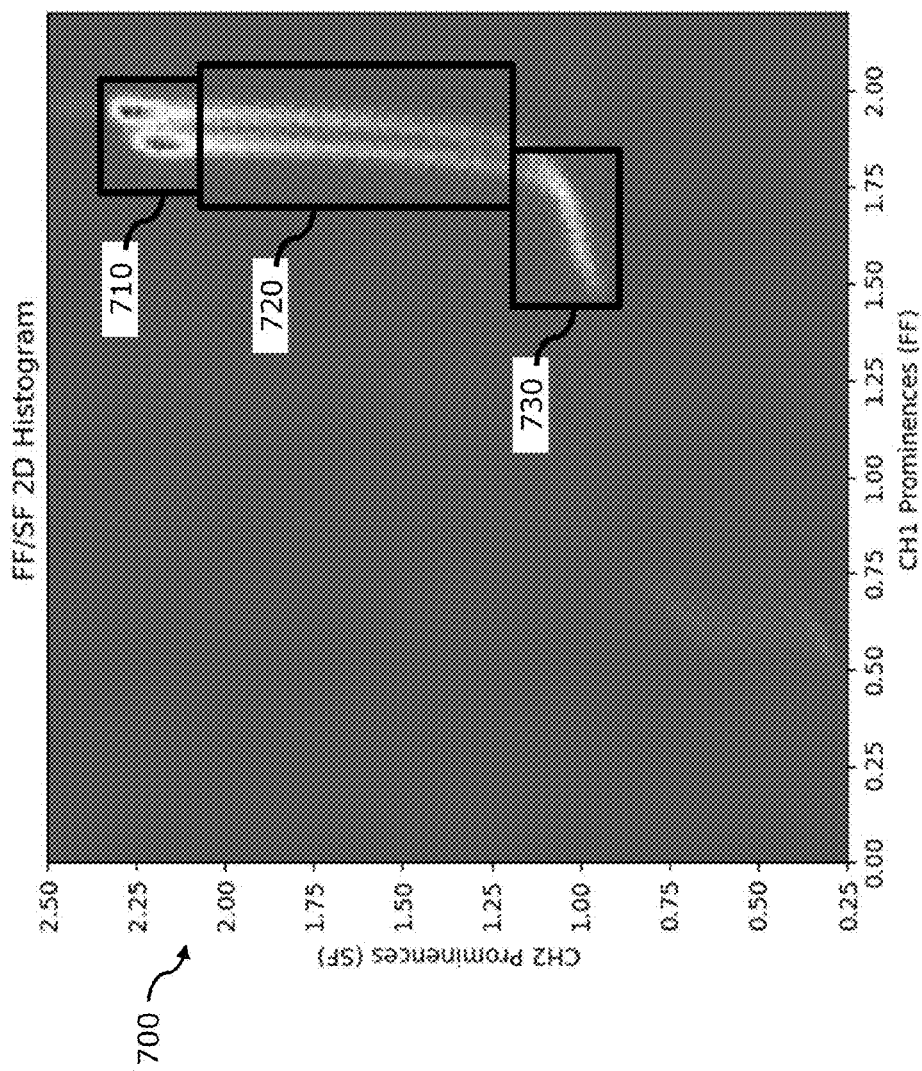
FIG. 7 depicts the data of FIG. 5 with indicating regions corresponding to different orientational features of cells in a sample according to various potential embodiments.

Referring to FIG. 5, an example forward fluorescence/side fluorescence (FF/SF) two-dimensional (2D) histogram 500 is depicted, plotting forward fluorescence (FF) ("CH1 Prominences") on the X-axis and side fluorescence (SF) ("CH2 Prominences") on the Y-axis. Histogram 500 uses a two-detector system on the cell population 410 highlighted on the 2D histogram 400. Region 510 points to the identifiable male population, with arrow 520 pointing to the "tail" of the female population that is contaminating the desired male collection. Histogram 600 in FIG. 6 depicts side fluorescence (SF) ("CH2 Prominences") on the X-axis and number of cells ("Count") on the Y-axis number of cells ("Count") on the Y-axis for the sample, with region 610 corresponding to the targeted cells. Here, target cells refers to cells which are to remain alive and which are not to be deactivated, ablated, sliced, or destroyed. Referring to FIG. 7, it can thus be determined that certain regions correspond with certain orientations and/or positions (e.g., cells with particular orientational features). In histogram 700 (based on the same data as FIG. 5), a first example region 710 may correspond to cells oriented flat side to a primary detector, a second example region 720 may correspond to cells oriented transitionally (between flat and edge), and a third example region 730 may correspond to cells oriented edge side to the primary detector. Based on the orientational features, and the sets of lights detected using forward and side detectors, the different cell types can be better distinguished.

In various embodiments, biasing cannot be achieved (or cannot be achieved as effectively or as efficiently), or is otherwise not performed, with a single detection location alone. In various embodiments, biasing operations are not derivable from a single set of lights (e.g., from only forward fluorescence or only side fluorescence), and thus the biasing operations may require two sets of lights traveling in multiple directions. In various embodiments, if biasing can be achieved using a single set of lights or from a single detection location it cannot be performed as efficiently or effectively as in biasing using more than one set of lights or lights from more than one direction.

To facilitate collection of light in multiple directions, various embodiments may integrate a fiber optic with a microfluidic chip that enables gathering emitted light (e.g., side fluorescence and side scatter from cells) in a direction that is substantially orthogonal to (or otherwise angled with respect to) the illumination laser axis. Referring to FIGS. 8A, 8B, 8C, and 8D, cutaway drawings of example microfluidic chips 800a, 800b, 800c, and 800d, respectively, with a sample channel 810 that has a flow axis 815, are shown. Chips 800a, 800b, 800c, and 800d include access ports 820a, 820b, 820c, and 820d for fiber optic elements 830a, 830b, 830c, and 830d, respectively, which may be inserted orthogonal to one or both of the illumination optical axis and/or the flow axis, or otherwise angled with respect thereto, in various embodiments. The access ports may have various configurations and may make various angles with respect to flow axis and/or with respect to the "forward" illumination axis, as represented in FIGS. 8A-8D. The fiber optic element (e.g., 830a, 830b, 830c, and 830d) may be selected for wavelength transmission, and be capable of collecting light emitted orthogonally, for example, from the cells that are being illuminated by an illumination laser (e.g., excitation laser). In various embodiments, this fiber optic element ("fiber") may be relatively large. This enhances the capture/detection of photons (i.e., increase number of photons captured and detected). A smaller fiber may not be able to collect a sufficient number of photons for discerning, for example, the 4% difference in DNA content (e.g., 4% difference in emission intensity) between X and Y chromosomes. In various embodiments, the fiber optic element may be positioned such that emissions from or caused by excitation by additional light sources (e.g., a kill laser or lasers that otherwise change the state of cells or other particles in a sample) are not captured. In certain embodiments, the fiber optic element may be partially masked or filtered (e.g., partial masks and/or filters 811 and 812 (FIG. 8D) which may comprise one or more suitable lenses or opaque components) to exclude such kill laser emissions. Alternatively or additionally, the size of the fiber may be selected to be spatially selective as to the detection location for a set of lights. For example, a smaller fiber may be used to only capture lights associated with a first fluorescence or excitation event and not from a second fluorescence or excitation event. However, a smaller fiber may reduce the quantity of photons that may be collected. Alternatively or additionally, the fiber may be angled or curved to position the face of the fiber such that kill laser emissions/excitation emissions are not captured by the fiber. These solutions may be more suitable the larger the fiber. The fiber optic element diameter may be such that, if not properly positioned, masked, or filtered, the fiber optic element may capture emissions related to both kill and detection lasers.

In various embodiments, the fiber may be selected based on a desired diameter and/or on a numerical aperture. The size of the fiber may be limited by the thickness of the microfluidic chip or by the manner of connection of the fiber to the chip. In various embodiments, the fiber may be between 10 and 600 microns in diameter. The diameter may be selected such that the fiber is large enough to collect sufficient light to provide enough data for a biasing determination. The fiber may be selected based on, for example, numerical aperture or the amount of light it is able to collect. This is based on the material of the fiber, and a numerical aperture of 0.1 to 0.5 may be sufficient to provide for enough light to be collected in various embodiments.

The light may be in at least one of two ranges: fluorescence (e.g., wavelengths at or above about 400 nanometers (nm)), and scatter light, which would have the same wavelength as the illumination laser (e.g., about 355 nm). Alternatively, filters that filter light closer to the wavelength of the illuminating laser (e.g., greater than 360 nm) may be used.

The fiber optic may terminate in a beam splitting cube which uses a dichroic optic to effect wavelength-based separation, so as to separate the fluorescence wavelengths from the scatter wavelengths. The two wavelength ranges may be focused on photo detectors (e.g., PMTs or APDs), and signals from these detectors may be processed using, for example, embedded hardware (FPGA). The corresponding peak intensity signals can be plotted as a 2-dimensional histogram as shown in FIGS. 5 and 7. The second detector signal system (FIGS. 5 and 6) provides additional information over the single detector (FIG. 4) which allows identification of the contaminating female cells. With two detectors, the additional information enables the creation of a gate which can better isolate the male population from the female population in various embodiments. For example, the gates disclosed in FIGS. 11B, and 13C. One skilled in the art will understand further gates may be used to isolate various populations.

In various embodiments, rather than using two detectors, a single detector with multiple pixels may be used, and lights from both detection points (e.g., along a first axis and a second axis corresponding to the different directions, such as side and forward) may be routed to the same multi-pixel detector. In certain embodiments, a bundle of fibers may be used at the side direction (e.g., second axis) and the fibers may be split off at the detector end of the bundle to different areas or zones on the detector such as a multi-pixel APD or a camera (e.g., a charge-coupled device (CCD) detector). Processing may be performed on the intensity of the emissions detected at the different pixels or areas of the detector or camera and this may be used to obtain additional information so as to functionally separate out a spatial location or to comparatively analyze the intensities at the different pixels or locations.

Moreover, a large fiber (as described above) may be used to capture more than one color or wavelength of laser or fluorescence emission at slightly different main channel locations. This information may be combined, summed, or differentiated to obtain additional information about the particle such as its size, shape, content, position, or orientation. Additionally or alternatively, a phase difference may be determined for the light captured by the fiber. These may be referred to as "physical or positional characteristics" of the particle.

In various embodiments, determining a positional characteristic of a particle using light intensities measured at first and second pixel detection regions may be very similar to the measured lights from two separate detectors, except that use of multiple pixel detection regions may be implemented using multiple pixels on a single detector. The light intensities and pixels could be from a same direction (bundle of fibers) or separate directions. The different measured light intensity levels can indicate a primary, secondary, or tertiary detection surface (e.g., flat-on, edge-on, or in-between). The different measured light intensity levels may also indicate a position (X, Y, Z) within the core stream. The specific mathematical operations that would be performed to provide the positional characteristics depend on the pixel location and the anticipated cell orientation/location with relation to those pixels. In various embodiments, extraction of characteristics could come from mathematical manipulation, regression, machine learning, or other approaches.

In various embodiments, component 850 may be used to guide and/or detect light that is transmitted through fiber optic 830. Component 850 may be another fiber optic, such as a fiber optic that is part of the sample platform 154 or other component of the sample processing system 150. In certain embodiments, fiber optic 830 remains with a removable microfluidics chip 158, while a fiber optic 850 may remain with sample processing system. The fiber optic 850 may have various shapes (e.g., such as a curvilinear section) and sizes to guide the light towards a detector and otherwise reduce cross-talk between components. In some embodiments, component 850 may be, or may comprise, a light detector.

Figure 8A:
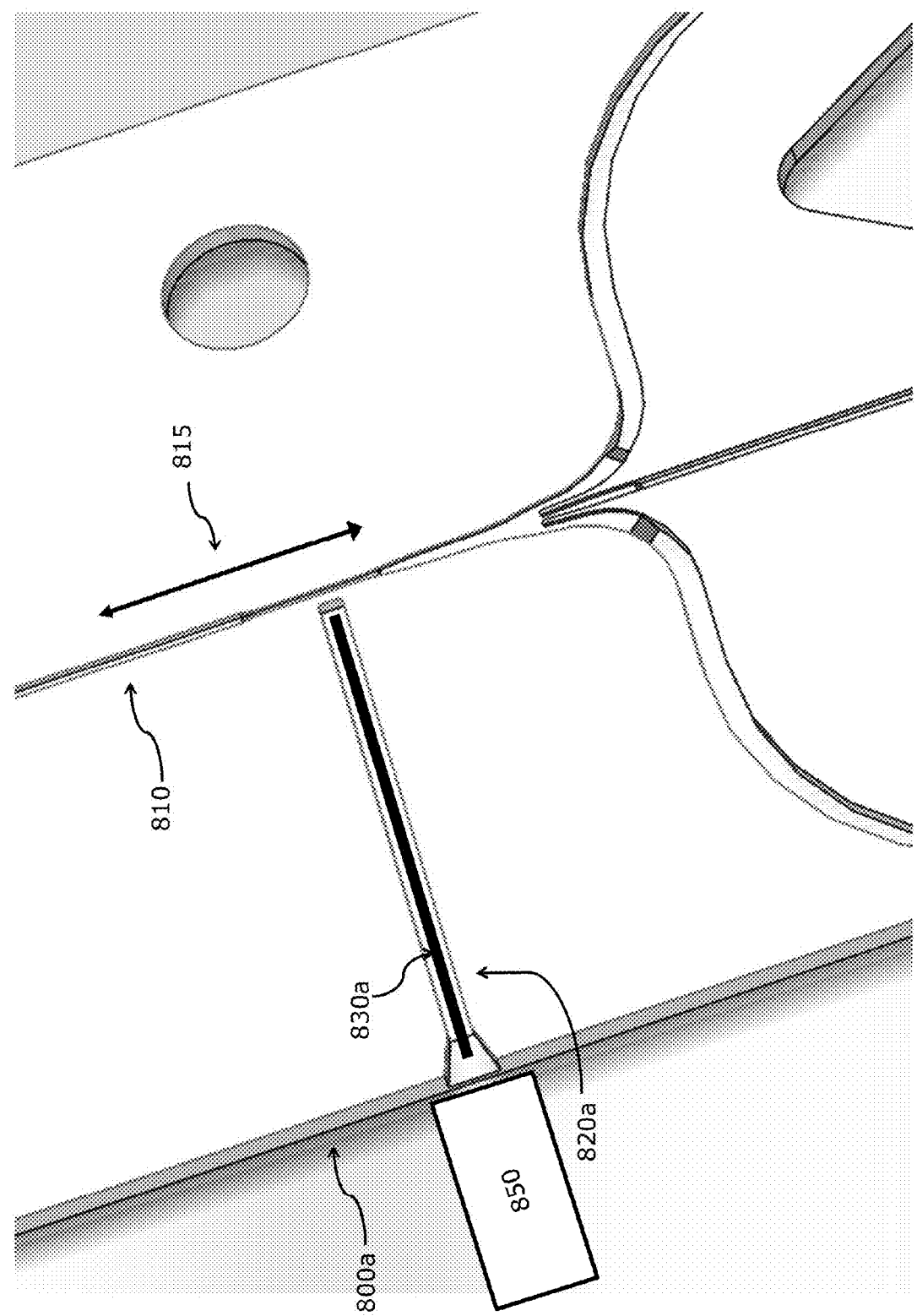
FIGS. 8A, 8B, 8C, and 8D include cutaway drawings of example microfluidic chips with side ports and fiber optics according to various potential embodiments.
Figure 8B:
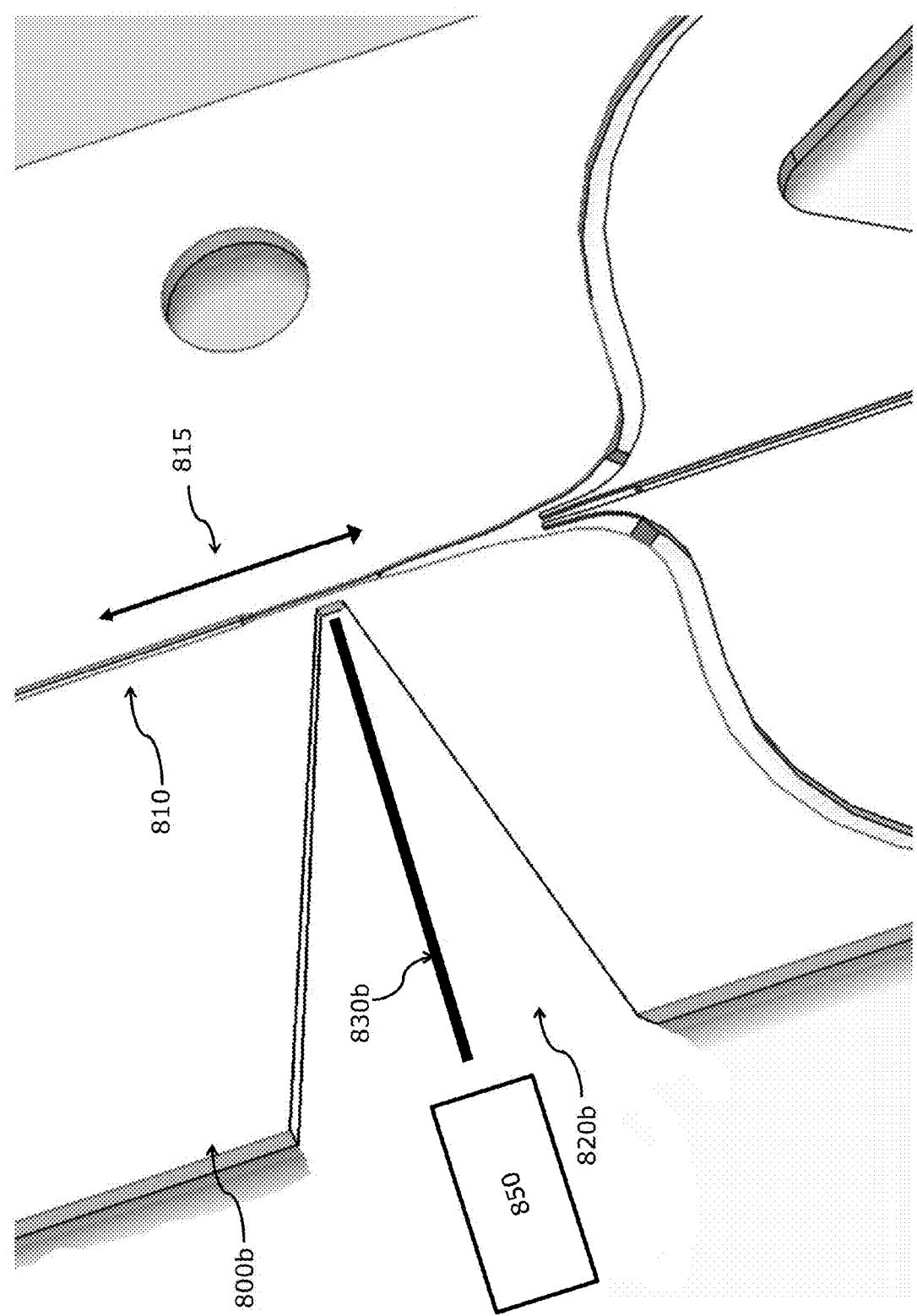
Figure 8C:
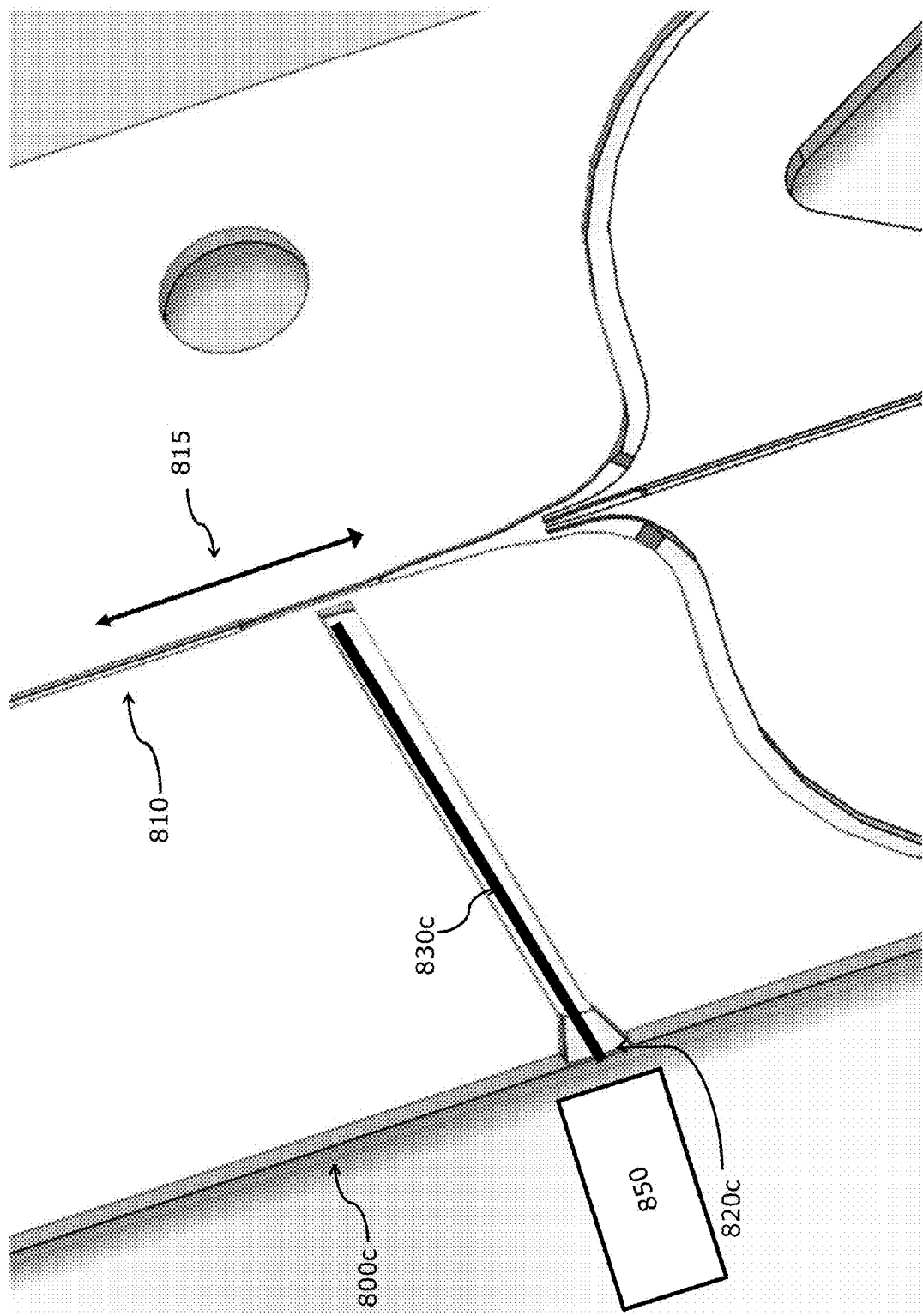
Figure 8D:
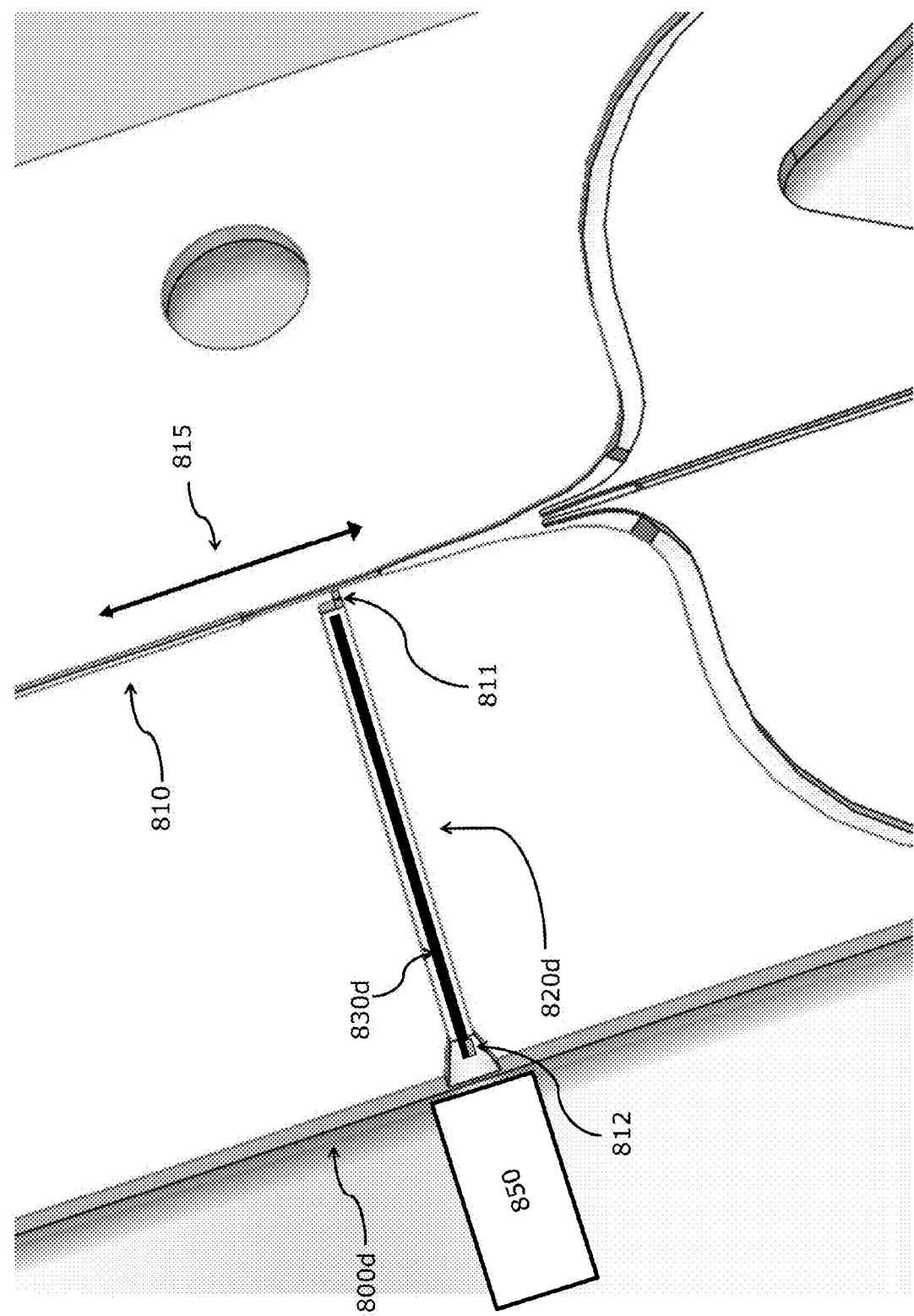

In various embodiments, fibers or other waveguides may enter a microfluidic chip at an angle as shown in FIG. 8C. Such a configuration could prevent light—either direct laser emissions or fluorescence emissions—from the kill location from entering the fiber and causing signal interference or simply overwhelming the detection signal. Alternatively or additionally, a partial filter or mask on either the microfluidic chip or fiber may be used as shown in FIG. 8D.

In various embodiments, lenses may be used to filter, mask, or better image the lights collected by the fiber. A filter at the chip-end could provide for masking or filtering at the detector-end of the fiber. A lens may also provide for better imaging for the use of a camera (e.g., CCD) for greater image analysis at the detector end.

Figure 9B:
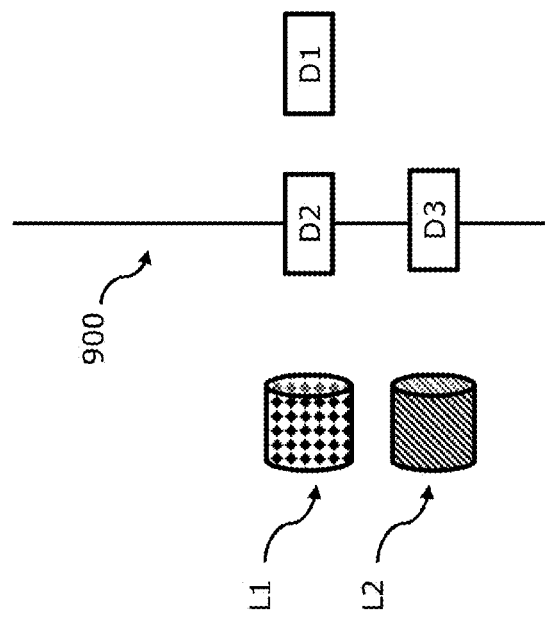
FIGS. 9A and 9B depict an example configuration that includes three detectors as components of a sample processing system according to various potential embodiments.
Figure 9A:
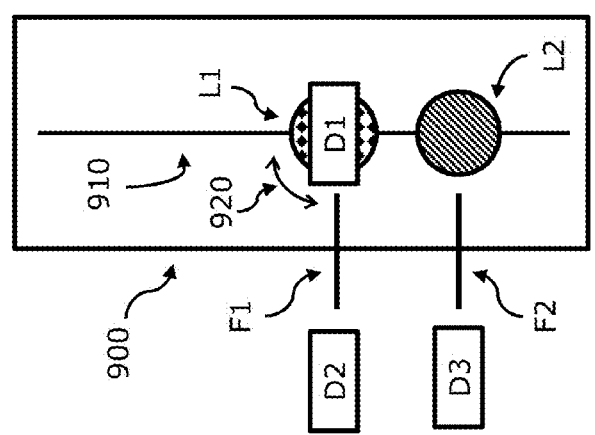

Referring to FIGS. 9A and 9B, alternative arrangements for components of a microfluidics sample processing system are depicted. In FIGS. 9A and 9B, microfluidics chip 900 is shown from two different perspectives, face-on in FIG. 9A, and edge-on in FIG. 9B. Chip 900 includes a sample channel 910 through which a sample flows in a downwardly direction. In FIG. 9A, a first light source L1 (e.g., an illumination laser) emits light from behind the chip 900 in a first direction (e.g., a forward direction or illumination axis) that travels out of the page. Light coincides with the sample (and cells or other particles therein) in the sample channel 910 as the sample flows down. Light from the chip 900 (e.g., fluorescence resulting from excitation resulting from light from L1 and/or scatter) traveling in the forward direction is detectable using a first detector D1 situated in front of the chip (on a side opposing the side on which L1 is situated). The light from L1 may be at a first wavelength, while the light from the chip that is detected by D1 may be a second wavelength (e.g., fluorescence). Light (e.g., side fluorescence or side scatter) from chip 900 traveling in a second direction can be collected via a first fiber F1, and detected using a second detector D2. It is noted that F1 collects light traveling along an axis that is orthogonal as shown (see 920) to the direction of sample flow in sample channel 910. Accordingly, light detected at D2 may be traveling at a substantially 90-degree (or other) angle with respect to both the illumination axis and the axis of sample flow. In various embodiments, the angle between the first and second directions may be between 75 and 105 degrees, or between 60 and 120 degrees, or between 45 and 135 degrees, or between 30 degrees and 150 degrees. Similarly, the angle 920 between the first direction and the flow direction may be between 75 and 105 degrees, or between 60 and 120 degrees, or between 45 and 135 degrees, or between 30 degrees and 150 degrees.

A second light source L2 may be placed downstream (e.g., further down along the sample channel 910 as depicted in FIG. 9A). L2 may be a biasing light (e.g., ablative laser, deactivating laser, activating laser, etc.) that emits light from behind the chip 900 along an axis that is parallel to the first direction such that the emitted light hits the sample in the sample channel 910 after the sample is no longer in the path of light from L1. Light (e.g., side fluorescence or side scatter) from chip 900 traveling parallel to the second direction can be collected via a second fiber F2, and detected using a third detector D3. Light from L2 can be used to, for example, deactivate (e.g., slice or otherwise "kill") cells in the path of L2 light. Cells traveling through sample channel 910 may travel through sample channel 910 in a single line, one cell after another, such that each cell in the sample coincides with both the L1 light and the L2 light. Light detected at D3 can serve as, for example, confirmation that each cell in the sample channel was hit with (and thus deactivated by) light from L2. For example, L2 light may also serve to excite fluorophores in the cells and result in side fluorescence. In such a case, if a burst of side fluorescence is detected at D3 following emission of L2 light, that side fluorescence could be used as an indication that the cell has been hit with deactivating light from L2.

In the perspective shown in FIG. 9B, light from L1 travels from the left of chip 900, rightward in the first direction, and hits the sample in the sample channel of chip 900. Light from chip 900 traveling in the first direction along the same axis is detected at D1 to the right of chip 900. Light from chip 900 traveling in the second direction (orthogonal to the first direction) travels outward of the page toward second detector D2 (positioned in front of the chip from the perspective in FIG. 9B). Similarly, light from L2 travels from the left of chip 900, in a rightward direction (parallel to the first direction), and hits the sample downstream in the sample channel of chip 900. Light from chip 900 traveling along an axis that is parallel to the second direction is detected at third detector D3 (positioned in front of the chip from the perspective in FIG. 9B). Data from D1 and D2 can be used to determine orientational features and cell types, and data from D3 may be used to provide confirmation of a "kill shot."

Figure 10:
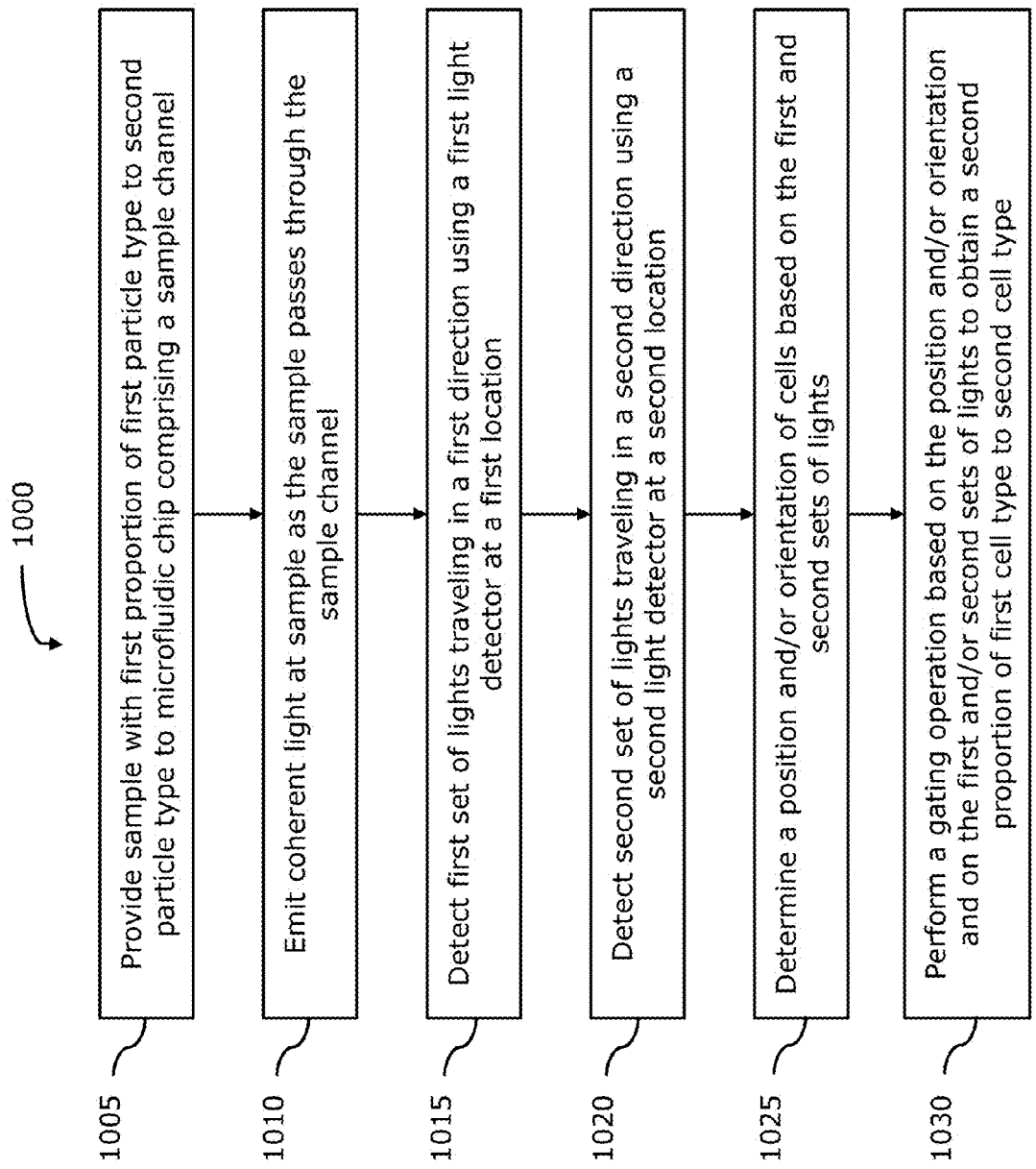
FIG. 10 represents an example flowchart for processing a sample to obtain a modified particle population according to various potential embodiments.

Referring to FIG. 10, an example process 1000 for enhanced differentiation of components of a sample is depicted according to various potential embodiments. At 1005, a sample may be provided to a sample channel of a microfluidics chip. For example, control unit 114 may signal fluidics components 166 (e.g., based on user inputs received through user interfaces 134) to effect delivery of the sample to the microfluidics chip 158 when the chip is at sample platform 154. The sample may have an initial (first) proportion of first particle type (e.g., first cell type) to second particle type (e.g., second cell type). The cells or other particles in the sample may have been dyed with a fluorophore before being flowed through the sample channel.

At 1010, a coherent light may be emitted at the sample as the sample flows through the sample in the sample channel. For example, control unit 114 may send control signals to an illuminating light 182 (such as an excitation laser) to emit light (which may have, e.g., a wavelength of 355 nm). At 1015, a first set of lights (with one or more wavelengths) traveling in a first direction (e.g., a forward direction that is along the illumination axis) may be detected. The first set of lights may be scatter lights (e.g., at the same wavelength as the illuminating light, 355 nm) and/or fluorescence (e.g., with a wavelength if about 400 nm). The control unit may control a first light detector 194 to detect light along the illumination axis, and receive signals therefrom corresponding to the detected light. The signals can be supplied by the control unit 114 to the analysis module 118 for processing. At 1020, a second set of lights (with one or more wavelengths) traveling in a second direction (e.g., a side direction that is orthogonal or otherwise angled with respect to the forward direction) can be detected using a second light detector at a second location.

At 1025, a position and/or orientation of a cell in the sample may be determined based on the first and second sets of detected light (e.g., as discussed above with respect to FIGS. 7 and 9. For example, histogram unit 122 may identify a cell's orientational feature based on which region in a histogram its light falls in. At 1030, a biasing operation may be performed based on the orientational feature and on the detected lights. For example, control unit 114 may control a deactivating light 186 (e.g., an ablation laser) directed at the cell identified as being an unwanted cell type. In this way, a modified proportion of cell types can be achieved in the sample.

Figure 11A:
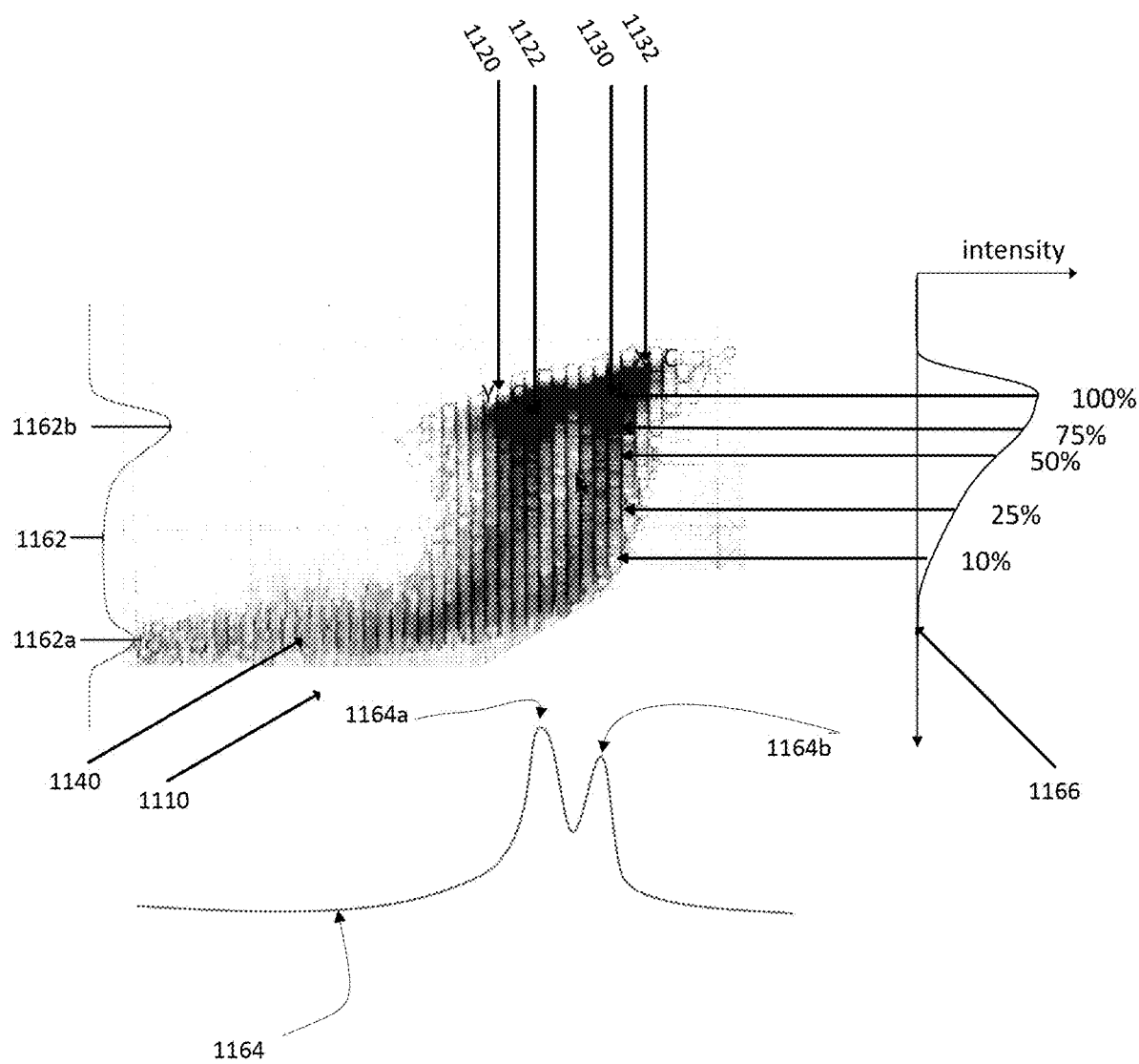
FIGS. 11A and 11B depict logically constructed gates which isolate male and female populations, according to various potential embodiments.
Figure 11B:
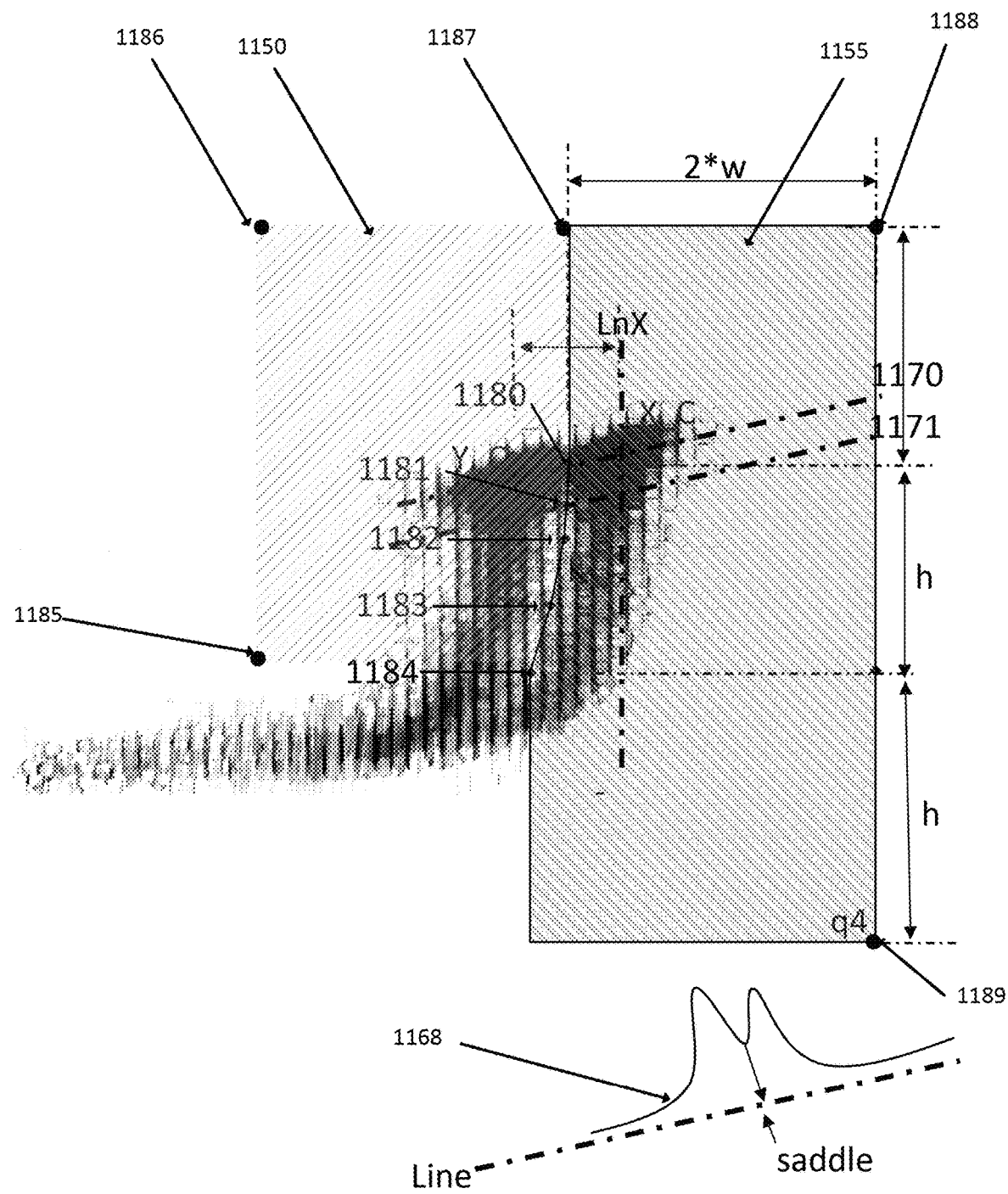

Referring to FIGS. 11A and 11B, a plurality of gates are disclosed which cover male and female populations. The logical isolation of each population may aid in counting, tracking, or observing the populations, and may be used in conjunction with biasing methods and systems such as those herein described to effect a biased population (e.g., predominantly male or predominantly female). As one skilled in the art will understand, similar gates may be used to identify populations along other dimensions. For example, an inactive or dead population may be gated. Similarly, such a population may be biased, tracked, etc. in conjunction with said gate. The intensity map 1110 may be assembled similarly to the histograms of FIG. 5, based on a plurality of peak forward and side florescence measurements, which may be determined by similar methods and systems. In some embodiments, additional or fewer sensors may be used to collect an intensity map. For example, additional sensors may be used to generate an n-dimensional intensity map 1110, or to increase the accuracy, detection rate, etc. of a two-dimensional intensity map 1110.

FIG. 11A depicts an intensity map without any overlaid gates. The intensity map 1110 depicts a similar population as FIG. 5, having an identifiable male population 1120, an identifiable female population 1130, and a tail 1140, which may comprise comingled male and female specimens. In some instances, the identifiable populations may be comingled as well. For example, the identifiable male population may comprise a small percent of female specimens and vice versa, where an insufficient dead band exists between the populations to fully segregate them. Each depicted population has a population center defined by the peak intensity within the identifiable population. In the depicted embodiment, the populations of male and female are approximately equal, and the peak intensity of each population is roughly equal. In some embodiments, the peak intensities of the two populations may be unequal. For example, a population resulting from an iterative biasing process, to further increase the skew of a population, a naturally diffuse population such as inactive specimens, a bi-modal population, tri-modal population, etc. In some embodiments the population center may be defined by alternate criteria, for example, by a geographic mean of the population rather than a point or area of peak intensity.

In the depicted embodiment, the two population centers are defined according to the two areas of highest intensity. The two population centers correspond to a male population and a female population; the male population center 1122 and the female population center 1132 are depicted. In some embodiments, two populations centers may be located based on an intensity profile. For example, a first intensity profile 1162 may be disposed along one axis of the intensity map, and indicates a summation of the detected population in the depicted rows. The first intensity profile may comprise a first local maximum 1162a, which may correspond to the tail 1140 of the intensity map 1110, and a second local maximum 1162b which may correspond to one or more of the population centers. In some embodiments, the first intensity profile may also comprise a third local maximum, which may correspond to an additional population center. For example, a male population center 1122 and a female population center 1132 may be separately discernable from the first intensity profile. In the depicted embodiments, the two populations are not readily discernable as pictured, however, further processing may enable their discernment.

A second intensity profile 1164 is also depicted having two local maximums, a first local maximum 1164a relating to the male population center 1122, and a second local maximum 1164b relating to the female population center 1132. A third intensity profile 1166 may then be calculated, based on the intensity at a vertical line drawn along the second local maximum of 1164b of the second intensity profile, so as to exclude the intensity contribution of the male population. A fourth intensity profile (not depicted) may be calculated based on the intensity at a vertical line drawn along the first local maximum 1164a of the second intensity profile 1164, so as to exclude the intensity contribution of the female population. Each of the third 1166 and fourth intensity profiles may then be evaluated to determine a center of the male and female population centers, respectively. In addition to the maximum intensity defined by the third intensity profile 1166, a plurality of additional intensities may be recorded along the vertical line passing through the female population center. For example, points at 75% of maximum intensity, 50% of maximum intensity, 25% of maximum intensity, and 10% of maximum intensity are selected. As one skilled in the art will understand, these numeric values are merely one possible set, and other numbers may be selected which may better form for particular data. Further, according to a selected coordinate system, any operations based on vertical or horizontal lines may be reversed or truncated, and such descriptions are intended only to describe the figures here within, and not to limit this disclosure.

Turning now to FIG. 11B, the same intensity map 1110 is depicted wherein a first sloped line 1170 passes through the male population center 1122 and female population center 1132. The distance between the two population centers may hereinafter be referred to as W, for use as a constant, and may refer to the vertical distance alone, or to the total distance, according to various potential embodiments. A fifth intensity profile is generated along the first sloped line 1170, wherein a saddle point (i.e., a local intensity minimum disposed between two local intensity maximums) is defined as the first point 1180. An additional set of intensity profiles are calculated along additional corresponding lines which are parallel to the first sloped line 1170. For example, a second sloped line 1171 is depicted. A saddle point is determined along each subsequent line. Saddle points 1180, 1181, 1182, 1183, and 1184 are shown, and may be determined based on the saddle point of the intensity profiles generated along various sloped lines (of which, only the first 1170 and the second 1171 are depicted). One or more gates may be bounded, in part, by a line formed along the saddle points. A first gate 1150, covering a predominantly male population and a second gate 1155, covering a predominantly female population is depicted.

In alternate embodiments, additional or fewer saddle points may be selected. In some embodiments, saddle points may be skewed to the left or right (e.g., to minimize female specimens gated by the first gate, or male specimens gated by the second gate). Additionally, the final saddle point (herein depicted as 1184) may be adjusted upward (e.g., in order to maximize the number of gated specimens, which may maximize skew) or downward (e.g., in order to minimize the number of gated specimens, which may maximize eligibility). For example, a gate may extend through the entirety of the tail, which may result in a substantial increase in gated specimens, but may reduce skew between populations.

In some embodiments, the intensity map 1110 may be oriented based on the two population centers. For example, the two population centers may be disposed along, or approximately along, a horizontal axis of the intensity map. For example, the intensity map 1110 may be drawn based on collected data, or based on historical data, in order to maintain the horizontal alignment of the population centers which may minimize computational intensity. In such an embodiment, the sloped line may have a slope of zero. Alternatively, a slope of zero may be presumed, in order to minimize or otherwise reduce computational requirements, or impose an offset relative to the depicted saddle points.

Various gates may also be bounded by the selection of appropriate bounding points. The bounding points may be predefined, or based on the saddle points or other measurements. In the depicted intensity map 1110, the first gate 1150 is bounded by a first bounding point 1185 placed at a point horizontal to the bottommost saddle point 1184, at a distance equal to twice the distance between the centers of the male population and female population. A second bounding point 1186 is placed at a point along a vertical line extending upward from the first bounding point 1185, twice the distance between the uppermost 1180 and the lowermost saddle point 1184 (which may be referred to, hereinafter, as "H", wherein the second bounding point 1186 is disposed 2H above the first bounding point 1185). A third bounding point 1187 is disposed at a point where a vertical line from 1180, and a horizontal line from 1186 intersect. Other bounding points locations are possible. For example, the first bounding point 1185 could be disposed 1H or 3.5H, with other bounding points adjusted, mutatis mutandis.

The second gate 1155 may be generally symmetrical to the first gate, or may differ. In the depicted embodiment, at the upper-right bound of the second gate, a fourth bounding point 1188, may be symmetric to the second bounding point 1186 (i.e., is located 2 W from the third bounding point in an opposite direction). A lower bound is defined at a fifth bounding point located H below the bottommost saddle point 1184, and the bounds of the second gate 1155 is completed by reference to the point where a horizontal line drawn from the lower bound 1189 intersects with a vertical line drawn from the right bound 1188. Thus the second gate 1155 may extend lower than the first gate 1150, which may, advantageously, increase eligible specimens, without the diminished skew that a lower gate would result in for the first gate 1150, due to the comingled tail.

Although additional populations may not be visible on the intensity map 1110, in some iterations, additional populations may be present. For example, inactive populations, XY specimens, etc. may be present. Thus bounding points may require additional specificity in some embodiments. Additional or fewer bounding points may bound the gate. Further, in some embodiments, a plurality of gates may be overlaid. For example, a plurality of gates may be disposed, and Boolean functions may be operated thereupon.

Figure 12:
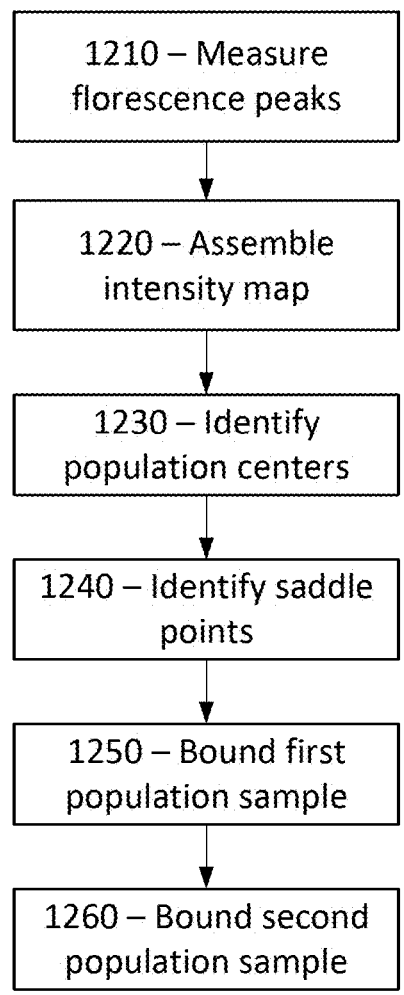
FIG. 12 represents an example flowchart for logically imposing a saddle gate over a histogram of forward fluorescence and side fluorescence, according to various potential embodiments.

Referring to FIG. 12, a method 1200 is disclosed for generating a saddle map. At operation 1210, florescence intensity peaks are measured in a first direction. For example, according to various embodiments disclosed herein, the first direction may correspond to a florescent detector oriented to detect front florescence (a "forward" fluorescence) from a sample. Further at operation 1210, florescence intensity peaks are measured in a second direction. The second direction may be disposed generally orthogonal (e.g. a side) to the first direction, or may not. For example, the second direction could be in the same direction at a different point in time.

At operation 1220, an intensity map is generated. The intensity map is a two dimensional representation of the peak intensity observed in each of the two directions. Thus, similar to the histogram of FIG. 5, the intensity map indicates a two dimensional representation of a population. The creation of the map may reveal a clustering of similar specimens of a population. For example, viable sperm may be tightly clustered on such a map. Further, male and female sperm may be discernable, but may require additional processing to delineate the population due to their proximity.

At operation 1230, population centers are identified. Population centers may be identified according to a peak intensity, and/or an expected location. For example, if two peak intensities are immediately adjacent, and another, slightly lesser peak intensity is disposed an expected distance, or in an expected direction away, the lesser intensity may be selected as a population center. If no suitable population centers can be located, additional data may be collected, an error may indicate a sensor problem, or data may be archived for later review.

At operation 1240, saddle points are identified. Saddle points may be identified based on local minimums bounded by two maximums. They may be identified based on a sloped line parallel to a line between the two population centers, a sloped line between two areas of equal density, along a row, etc. Saddle points may be defined at regular intervals, or as a pattern selected to maximize skew, or may be otherwise be selected.

At operation 1250, a first population is bounded by forming a gate comprising the population between the saddle points and outer bounds. The outer bounds may be defined statically, in relation to population features, manually, etc. In some embodiments, the bounds (and/or the saddle points), may be dynamically adjusted. For example, an offset from a saddle point may be used to bound a population. In order to maximize skew, a gate may be formed which does not include saddle points. For example, a gate may include left or right shifted points from calculated saddle points in order to increase the proportion of a population bounded by a gate or the overall number of specimens bounded by a gate (e.g., by reducing or increasing the captured comingled populations).

At operation 1260, a second population is bounded in a similar manner as the first population. This operation may be performed in addition to or instead of operation 1260. For example, in many embodiments, only a single gate may be formed. In some embodiments both gates may be formed (e.g., for data tracking/analytics) but only a single gate (or no gates) will be used in conjunction with a biasing process. The disclosed steps disclose some embodiments of a method 1200, however, one skilled in the art will understand that certain steps may be added, omitted, altered, etc. according to other embodiments of this document. For example, a related method may be performed based in three measurements, (e.g., florescence or other measurements) as a three dimensional system.

Figure 13A:
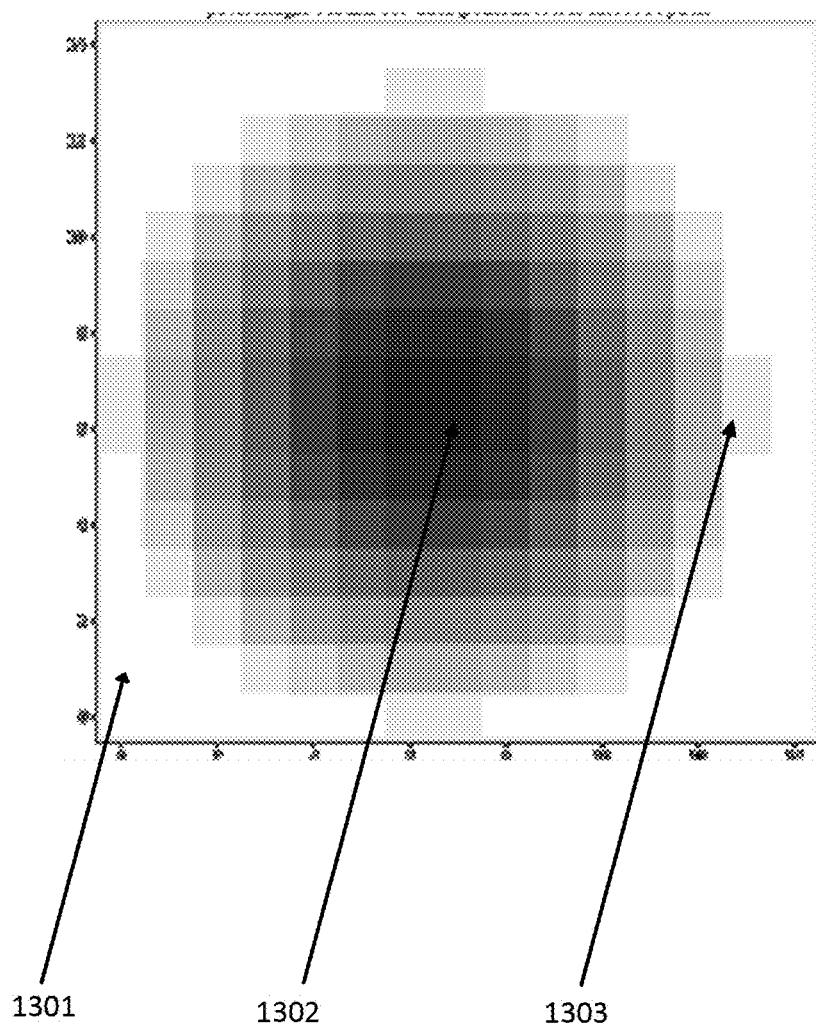
FIGS. 13A, 13B, 13C, and 13D depict the logical imposition of a kernel density estimation gate over a fluorescence histogram, according to various potential embodiments.

Referring to FIG. 13A, a digital approximation of the Epanechnikov kernel 1301 is disclosed. Similar approximations may be considered with other kernels, such as a Gaussian kernel. A plurality of kernels may be placed which may smooth a resulting dataset. For example, the depicted kernel may have n-bits of depth (i.e., each pixel may be represented by a probability value of between 0 and $2^n-1$) for each pixel, and a resolution of m pixels. For example, an 8 bit kernel may have 256 possible values for each pixel thereof. Thus, the center value (i.e., root pixel 1302) may have a value of 200, and an outer pixel 1303 may have a value of 10. The depicted kernel has a radius of 7 pixels. Increased pixel resolution may better capture the kernel (e.g., the parabolic Epanechnikov kernel), and thus smooth the display, however, such a smoothing may increase the computational load on a system. In some embodiments, a system must operate in real time (e.g., in certain systems relying on the classification of specimens to bias them), thus computation load may be managed according to available computing resources. For example, one embodiment may have 4 bits of depth and a 5 pixels radius, while another may have 8 bits of depth, and a 32 pixel radius. Note that although the kernel is depicted pictographically, the pixels of FIG. 13A, like other datasets, need not be presented on a display, to a user, etc. The pixel nomenclature is intended to describe the various discrete locations used to sum the various kernels, and does not necessarily relate to display technology. Each kernel may represent a measurement of a cell (e.g., a sperm cell). Each measurement may comprise a plurality of detections. For example, the florescence of a cell may be measured in two directions, and placed onto a pixel map based on the dimensions (e.g., a side florescence may determine a location along an x-axis, and a front florescence may determine a location along a y-axis). Additional or fewer measurements may result in a pixel map with additional or fewer dimensions.

Figure 13B:
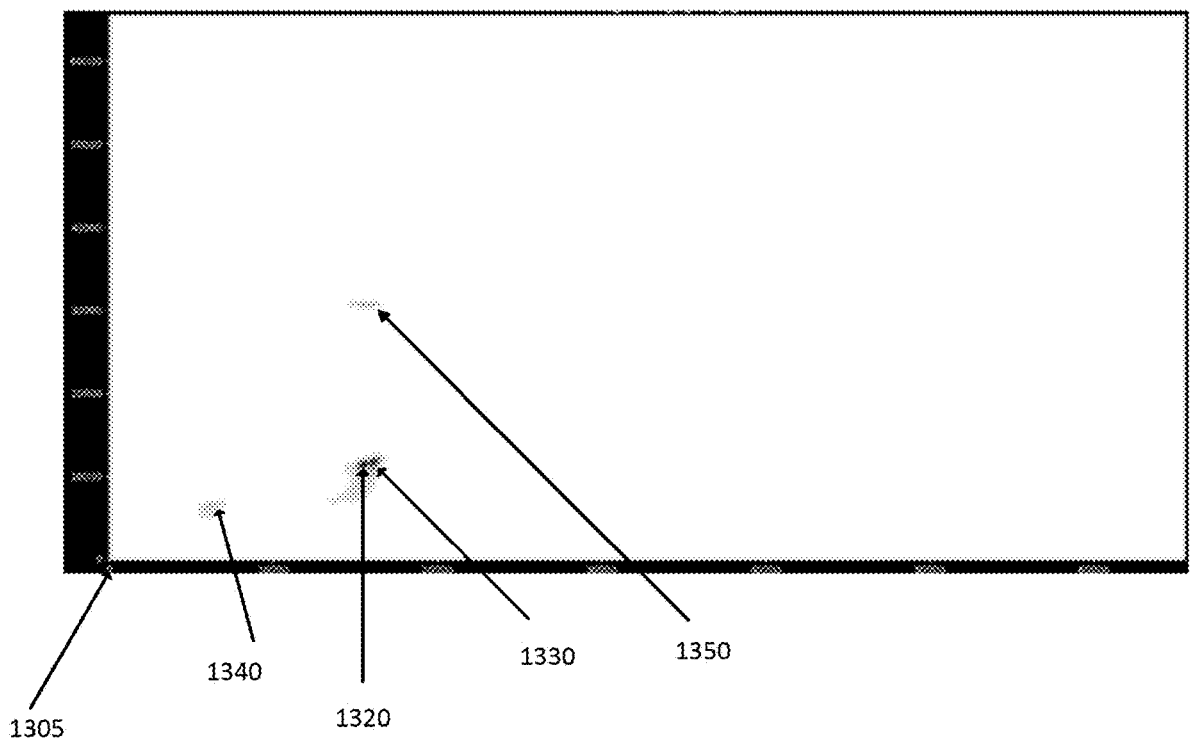

Referring to FIG. 13B, a plurality of pixels may be summed onto the pixel map 1305. For example, if two partially offsetting pixels are overlaid such that one pixel value of 200 overlays a pixel value of 10, then a value of 210 is generated. Additional kernels may continue to be added to form a pixel map 1305 that represents a density function of the kernels, such as in relation to the florescence of a plurality of cells measured from two directions. Thus, the florescence of the various cells may be mapped so as to reveal the relative florescence of various identifiable populations of cells. For example, one population of cells may be described as a population of inactivated cells 1340, male cells 1320, female cells 1330, etc. Some populations may describe instrumentation limitations or errors. For example, some cells may be detected with very high levels of florescence in one direction (e.g., a side direction) due to interference from other system components, such cells may be termed as saturated cells 1350. In some embodiments, such cells may be categorized as male, female, inactive, etc., such as by taking further measurements, or by additional data processing steps.

Some populations or errata may be removed from a pixel map in order to better analyze one or more populations of interest. A population of interest may be identified based on characteristics, location, or past experience. Referring again to FIG. 13B, two populations of interest are disclosed, a male population 1320 and a female population 1330. The populations show the same characteristic shape as FIGS. 7 and 11. Further, the populations are substantially denser than other detected populations. For example, a presumed inactive population 1340 and a presumed saturated population 1350.

The populations of interest may be better analyzed by adjusting pixel map 1305 to exclude extraneous populations, unpopulated space, noise, etc. The columns of the pixel map may be summed to plot a histogram, and a derivative of the histogram may be used to locate local maximums and minimums of the histogram based on the zero crossings of the derivative. In certain embodiments, a dead band is used to suppress noise induced zero crossings. The dead band may be fixed, or may be dynamic. For example, the dead band may be based on a percent of a peak derivative value. For a defined population, various critical points may be generally predictable, and may be defined based on the emergence location, direction of exit/entrance from dead band space, slope, etc. All columns outside of the range of interest may be cleared to reduce noise and information regarding undesired populations.

Such filtering of a column histogram may not adequately remove noise or extraneous populations. For example, the saturated population 1350 may be vertically aligned with the populations of interest, and consequently, may not be removed by column filtering. Thus, a second histogram of rows is generated and a derivative of the histogram is generated. Similar to the column filtering, known populations may be identified for inclusion or exclusion, and noise may be removed by the use of a dead band. Known or desired populations may be determined based on the zero crossings of the derivative, and/or row by row parsing (e.g., row by row parsing near a local maximum or minimum determined according to the derivative).

Figure 13C:
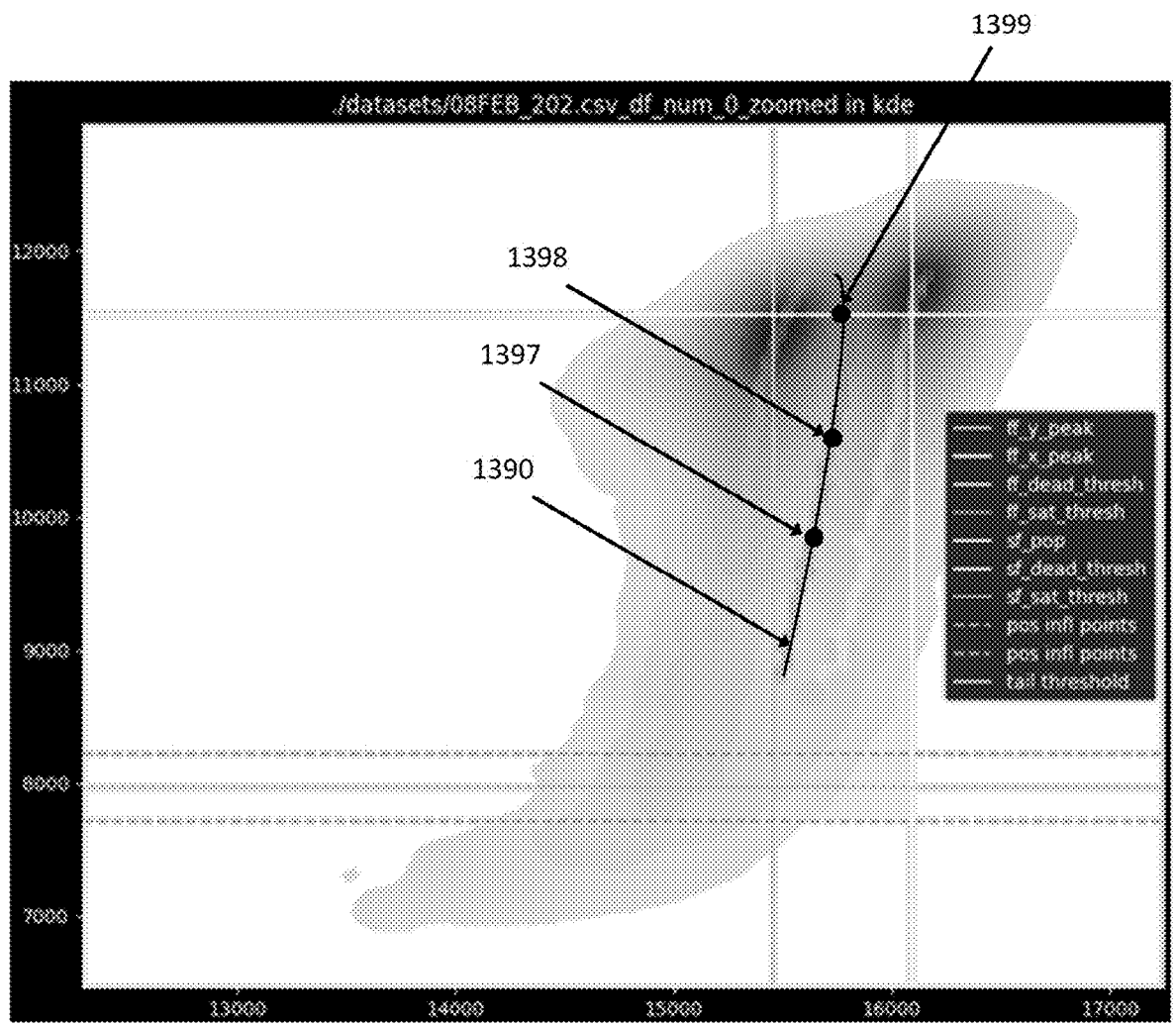

FIG. 13C illustrates a zoomed version of FIG. 13B, with focus on the male/female populations. The particular area of interest may be calculated according to the analysis of the histograms described above. Because the populations of interest are disposed closely to each other, and may be comingled, a division of the two populations is more computationally intensive. However, because much of the pixel map has been eliminated, the computationally intensive task may be performed on a localized portion thereof, such as the depicted portion.

A second histogram of rows is generated, and used to determine a lower threshold. The lower threshold eliminates the tail where the male and female cells may be heavily comingled. The lower threshold may be defined according to a minimum density, or an inflection in the change of density. For example, the generally decreasing density of the pixel map along the negative y axis of the pixel map may be slowed by the curvature of the tail, at which point an inflection point may establish a threshold of the tail.

With the threshold established, the pixels above the threshold may be sampled row by row to establish a trough line 1390. The trough line 1390 is defined by a local minimum disposed horizontally between two local maximums. A critical point 1399 is defined by the point on the trough line vertically disposed at the maximum density according to the row histogram, and may be a terminus of the trough line 1390. The slope of the trough line 1390 is zero at the critical point 1399 (i.e., as depicted, is vertical). Additional points along the trough line are also collected. A second trough line point 1398, and third trough line point 1397 are depicted. Because increased points generally improve the fitting of the trough line, and hence improve skew, several points may be defined. For example, a trough line point may be defined for every row.

In some embodiments, the plotted trough line 1390 may be used directly. In other embodiments, a function (e.g., a LaGrange polynomial) may be generated based on the trough line 1390. The generation of the trough line 1390 may include rotating the pixel map by 90 degrees to simplify the needed computations. Moreover, restricting the polynomial to a second order polynomial, and forcing the polynomial to traverse through the critical point with a slope of zero may further reduce computations, and may fit some trough lines 1390 well. In other embodiments, higher order polynomials may be selected, and a best fit line may be accepted. In some embodiments, either the generated trough line 1390 or the generated function may be approximated by a fixed number of points. For example, a polynomial may be reduced to 4, 6, or 8 line segments. Advantageously, such an approximation may reduce the computation required to define a gate based on the trough line in certain systems.

Like the saddle of FIG. 11, the trough line 1390 may be bounded based on fixed points, relative distances, or other criteria. For example, the vertical distance between the critical point and the tail threshold, or the distance between the two peaks at the row of the critical point may be used as a base measurement. A bounding point of the population to the left or the right of the trough line 1390 may be some multiple (e.g., 0.1×, 0.25×, 0.5×, 1×, 2×, 5×, 10×, etc.) of the base measurement to define a gate. A base measurement for width may also be defined or computed.

Figure 13D:
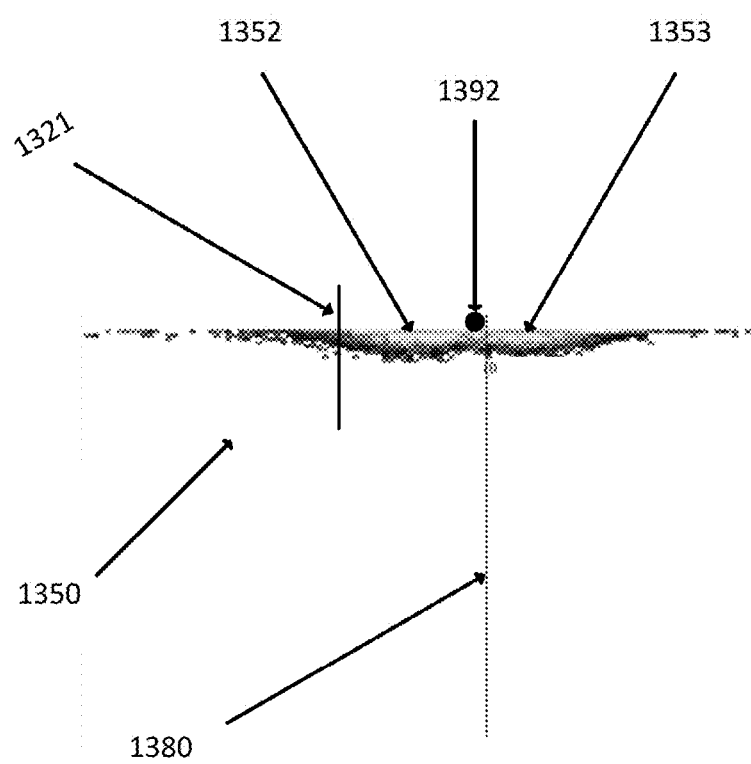

Referring to FIG. 13D, a zoomed view of the saturated population 1350 is visible, and generally divided into two populations, a predominantly male saturated population 1352, and a predominantly female saturated population 1353. A vertical extension 1380 of the critical point 1399 is depicted approximately bisecting the saturated population into male 1352 and female 1353 constituent portions. By extending the gate vertically upward from the critical point, the saturated population 1350 may be included in a gate comprising a the population to the left or the right of the trough line 1390 (e.g., because the extension of the polynomial trough line may not bisect the population, or may impose additional computational load, relative to extending the critical point upwards).

Although it may be computationally acceptable (i.e., not too computationally intensive and thus not too time consuming for a particular application), extending the critical point 1399 vertically upwards may be undesirable because the concavity of the trough line 1390 above the critical point may impact the separation of the unsaturated male and female populations. Thus, the gate may be selectively extended, based on the presence or non-presence of saturated cells. For example, a row histogram may indicate the presence or non-presence of a saturated population 1350. If a saturated population 1350 is present, which may be determined according to a minimum density of a first row histogram, the gate may be extended upwards to include the saturated population. Advantageously, this may maximize eligible cells. Where a saturated population 1350 is not present, the gate may be constructed without regard to any potential saturated cells. Advantageously, such an embodiment may maintain a desired skew within the main population by maintaining the concavity of the trough line above the critical point 1399 in the non-saturated population.

Alternatively, or in addition, it may be useful to bisect the population by another method. For example, the polynomial may be generated without regard to the saturated population and, thereafter, a line segment may extend from above the critical point 1399 to a saturation bisection point 1392 on or above the saturated population 1350. Thus, the main population above the critical point may maintain skew performance, and the population may be more accurately bisected.

The saturation bisection point 1392 may be computed similarly to the points along the trough line 1390, for example, based on a row histogram showing a local peak kernel density at about the center of the saturated cells 1350, and may then be offset (e.g., raised vertically a fixed number of rows). Because the comingled "tail" cells of the saturated population may not be readily discernable, a potential gate may be more tightly bound. A first bounding line 1321 is shown disposed close to the center of the male saturated population 1352. Although the first bounding line 1321 may result in bounding many male specimens out of a gate, it may also increase selection specificity (i.e., skew). The first bounding line 1321 may be moved leftward or rightward in order to balance skew and eligibility. For example, the first bounding line 1321 may be placed to avoid exclusion of the entire saturated population, which may, advantageously, increase the number of gated cells. Similarly, another bounding line (not depicted) may be disposed along a right side of the saturated cells. However, as the saturated population 1350 exhibits similar characteristics as the non-saturated population, limited comingling may be present on the right side, and thus a wider bounding line may be selected, such as a bounding line extended from the right side of the population.

In some embodiments, a plurality of gates may be used in combination (e.g., separate gates may be used for the saturated populations and the non-saturated populations). Advantageously, additional gates for a discrete population may be generated parallel to any other gates present, which may be better suited for at least some systems than a single more complex gate. In such embodiments, the additional gate may be imposed in a similar fashion to any gates associated with the non-saturated populations, or may be imposed by a different method, for example, may be imposed by the saddle method disclosed by FIG. 12, or another method.

Figure 14:
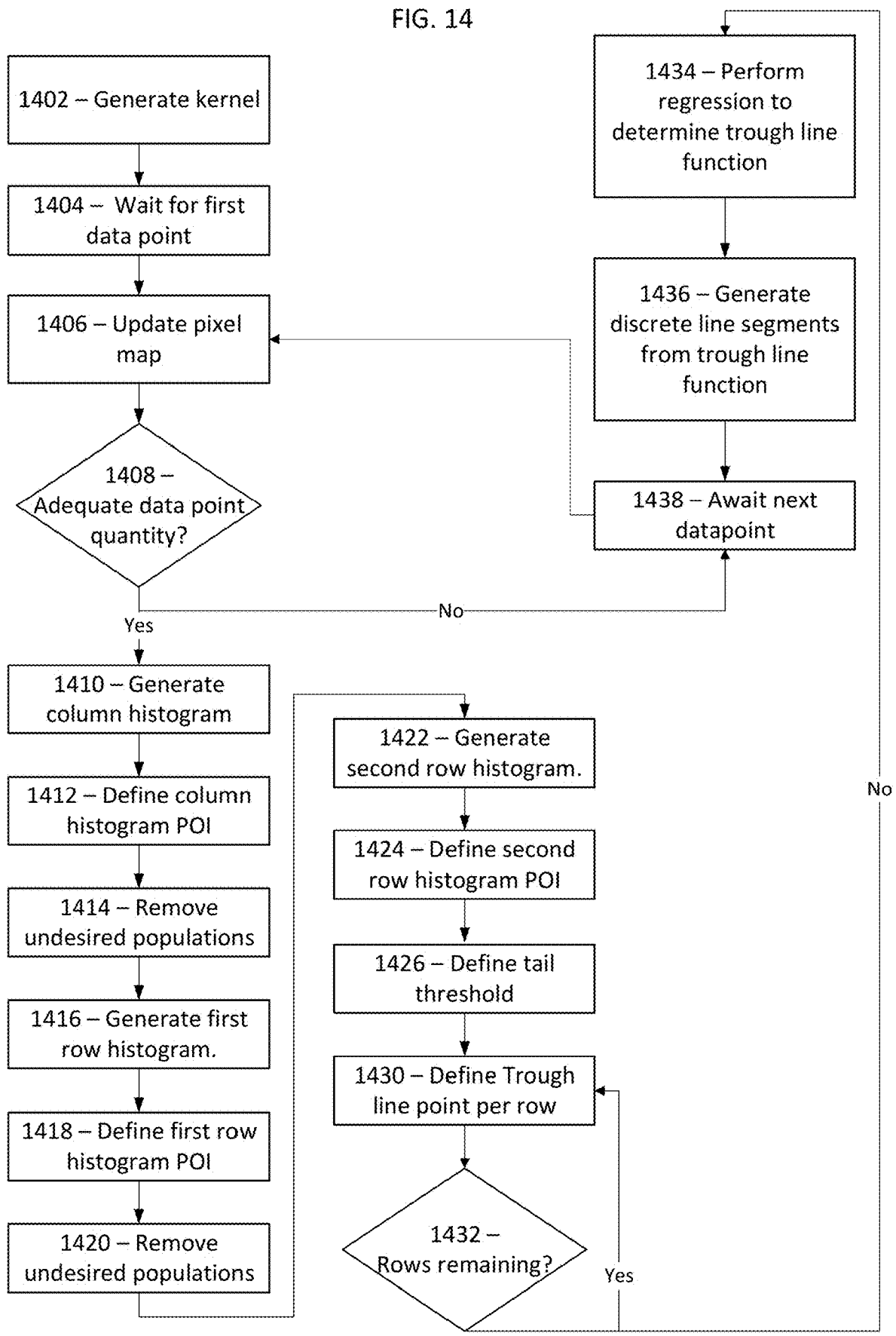
FIG. 14 represents an example flowchart for logically imposing a kernel density estimation gate over a fluorescence histogram, according to various potential embodiments.

Referring to FIG. 14, a method 1400 is described to generate a Kernel Density Estimation Gate. The method may be performed upon many data sets according to various embodiments, such as the data sets illustrated in FIGS. 13B, and 13C. At operation 1402, a kernel is generated. The kernel may be selected for computational performance, accuracy, etc. For example, a kernel may be selected according to the implied accuracy of various sensor devices detecting cells, and according to quality of results. In some embodiments, a plurality of kernels may be generated for a dataset (e.g., real time data, historical data, etc.) and the method 1400 may be performed with each, and comparing the results. Once the kernel is selected, a digitally resolved kernel is generated according to system requirements (e.g., the amount of computer memory or processing resources, detector resolution, etc.). In some embodiments, a minimum resolution, depth, etc. of the kernel may be determined, and a system may be designed to support such a system. In some embodiments, a digitally resolved kernel may be configured to operate on particular available hardware.

At operation 1404, the system awaits a first data point. The data point relates to the properties of a cell (i.e., individual) of a population of cells. For example, the data point may be a florescence of DNA comprised within various populations of sperm according to a plurality of detectors. For example, one dimension of the data point may relate to the florescence detected in a first direction (e.g., a "front" direction), and the second data point may relate to the florescence detected in a second direction (e.g., a "side" direction). In some embodiments, the absolute florescence may be graphed, in other cases, the fluorescence may be normalized (e.g., to account for detector differences, to preprocess data, etc.). For example, data may be range checked to minimize later processing.

At operation 1406, a kernel representing the data point is added to the pixel map. The addition of the data point may include a root pixel, representing the probabilistic center of the location data point, as well as the remaining kernel, representing a (typically decreasing) probability moving away from the root pixel to the outer edges of the generated kernel. If the addition of the kernel overlays any existing kernels, each overlapping pixel is added to the pixel map, so that cumulative kernels may show probability densities on the pixel map in excess of that available in each pixel. For this reason, pixel map depth may need to exceed kernel depth (e.g., each pixel may require 32 bits of depth to display pixels having 8 bits of depth). Because solving the kernel for the desired resolution and depth may be computationally expensive, in many embodiments, the pre-generated kernel may be summed to each pixel, based on offsets from a root pixel, which may be at a center of the kernel or otherwise.

At operation 1408, the number of data points is checked for adequacy. In some embodiments, a simple numeric check may be performed (e.g., at least 100,000 data points, 120,000 data points, or 140,000 data points). In such an embodiment, this operation may further comprise incrementing a data point counter. In some embodiments, another check may be performed instead of or in addition to a counter. For example, the pixel map may be checked for a minimum density. For example, if any population exceeds a density of X, an adequate number of data points may be collected. Alternatively, or in addition, additional operations 1410 through 1434 may be tentatively performed (e.g., against a copy of the pixel map so the data is not impacted) in order to check if the number of data points is adequate. Advantageously, such a method may enable earlier identification of gate zones which may allow the biasing or other operations upon the populations. If the number of data points is determined to be insufficient, the operation may proceed to operation 1438, and await future data points.

If the number of data points is determined to be adequate, a first histogram is generated at operation 1410. Although FIG. 14 describes a column histogram, the first histogram may be taken in any dimension (indeed, the method 1400 may be suitable to be performed in an n-dimensional system, thus the first histogram may be neither a row or column histogram). The first histogram is taken to eliminate certain populations and noise from the chart. For example, dead cells, noise, and saturated cells may be desired to be eliminated from the pixel map. The histogram may be one-dimensional, or, in some embodiments, n-1 dimensional, and measure the density function represented by the pixel map across at least one axis.

By generation of the first histogram, various points of interest can be established at operation 1412 to identify population(s) of interest, and other population(s) may be removed. For example, the density function of the pixel map may be plotted, along with additional processed functions (such as derivatives, keep out bands, minimums, etc.). Points of interest showing local minimum or local maximum may be used to determine a center of a population location, and the population of interest may be selected according to dynamic or static processes. In some embodiments, a predetermined or set number of pixel columns (such as 500 pixel columns) may be selected, centered about the center of peak density, or offset therefrom. In other embodiments, a variable number of columns may be selected according to sensed data (e.g., based on local minimums or maximums). In some embodiments, a fixed number of columns, rows, pixels, etc. may be limited by available computing power. Regions of interest (ROIs) are determined based on the selected points of interest. Some embodiments comprise multiple regions of interest. For example, in one embodiment, a saturated population may be a region of interest in addition to the X/Y populations discussed henceforth. In such embodiments, additional processing may be performed within each region which may be similar or different than the present method 1400.

At operation 1414, data of populations falling outside of the regions of interest is discarded, archived, deleted, etc., so that ongoing processing may be based on the selected region of interest. Alternatively or in addition, elements of the pixel map may be filtered according to defined locations or properties. For example, if a location of a population of interest is known in advance of plotting, certain measurements may not be plotted, and pixels falling below a pixel threshold (e.g., due to noise, errant samples, etc.) may be suppressed, regardless of region.

At operation 1416, another histogram is generated, a first row histogram. In some embodiments, such as those depicted in FIGS. 13B and 13C, the first row histogram includes side-fluorescence data taken of various populations of sperm, and is a density histogram of rows of the pixel map. In alternate embodiments, the second histogram may be based on an orthogonal axis, which may or may not relate to a physical dimension (e.g., where the first histogram is a first fluorescence measurement, and the second measurement is based on a second orthogonal or non-orthogonal florescence measurement, or another measurement such as a speed, position, etc.). The second row histogram may be generated over a limited portion of the pixel map, since a portion of the pixel map may have been deleted, zeroed, archived, etc. at operation 1410.

In some embodiments, the second histogram may be omitted. For example, the use of pre-processing or an appropriate coordinate system may be generated to minimize populations not captured by the first histogram. In some embodiments, the second histogram, or the first histogram, may be generated only once (e.g., following a determination of adequate sample size) which may, advantageously, minimize processing requirements which may lower associated hardware requirements, or enable increased resolution and/or depth.

At operation 1418, various points of interest are found on the first row histogram. Determining the points of interest may be based on a maximum density, or additional processing may occur. For example, a derivative of the histogram may also be plotted to detect zero points (e.g., local maximums and minimums), and such local or global maximums and minimums may be used to determine a region of interest for further inspection and processing.

At operation 1420, data concerning undesired populations may be discarded, archived, deleted, etc. For example, all data outside of a region of interest on the pixel map may be so disposed of In some embodiments, some data may be discarded without regard to what region the data falls in. For example, pixels below a threshold of density may be discarded (i.e., set to 0 density), or other pre-processing may occur to simplify later analysis.

At operation 1422, a second row histogram is generated over a region of interest which may have been reduced by operations 1414 and 1420. According to some data sets, the region of interest may be substantially smaller than the original pixel map, which may enable additional computation.

At operation 1424, a density function of the rows of the pixel map (or a portion thereof) is generated, and a first and second derivative of the density function is generated, which may aid in determining inflection points. The inflection points may be used to identify points of interest (POI) on the map. For example, positive inflection points located below and away from a center of population may indicate a lower threshold. Advantageously, such an approach may enable the location of features of relatively complex pixel maps, such as those having tails, which may be difficult merely considering the density values themselves, or their absolute rates of change.

At operation 1426, a tail threshold is defined. The tail threshold may be defined based on an inflection point of the density function of the second row histogram of operation 1424. For example, the rate of decreased density lowers as the lowered population density away from the population centers slows upon reaching a tail (i.e., due to the tail being aligned along the rows rather than perpendicular to it). In some embodiments, the point of inflection may be used as the tail threshold. In other embodiments, a fixed or variable offset may be used. For example, 25 pixels above or below the inflection point may be selected. In some embodiments, the threshold may be dynamically determined based on a current eligibility or skew of the sample (e.g., the threshold may be adjusted upward to increase skew, or downward to increase eligibility).

At operation 1430, a trough line point is defined for each row. The rows may be a single pixel of height, or another height with a number of pixels greater than one, according to the requirements and available computing power. A histogram of each row is generated to determine a location of a first population, a second population, and a trough line point, disposed between the two populations. Of particular note, there is a trough line point determined at a row having a maximum density according to a row histogram (which is defined as the critical point).

At operation 1432, a determination is made whether all rows have been completed. Rows may be completed according to every row within the region of interest above a tail threshold, or may be further limited. For example, rows may be limited by an upper bound defined according to the density function (e.g., upon reaching a minimum density), or by an inflection point or by the critical point, or an offset therefrom (e.g., 10 pixel rows above the critical point may have associated trough points calculated). In some embodiments, a trough line may be defined according to additional processing steps. For example, a row may be defined along a sloped line on the grid, similar to the process of method 1200.

At operation 1434, a regression is performed along the trough line points to define a polynomial function describing the trough line. The function may be limited by a plurality of trough points, by a slope at the critical point (e.g., slope may be limited to zero), etc. In some embodiments, the trough line may be limited to a second order polynomial. For example, in an embodiment where trough line points are not sampled above a critical point, such an embodiment may enforce a desired concavity. In some embodiments, the polynomial may be left or right shifted, in order to balance a desired skew or eligibility metric. In order to calculate the polynomial, the pixel map may be rotated, since various references to "above" "below," etc. may be arbitrarily defined. In some embodiments comprising a variety of sensors, such references may be understood with regard to n-1 dimensions, n-2 dimensions, etc., down to a single dimension. For example, in a 5-dimensional system, the above may be performed with respect to 1 dimensions, or 4 dimensions.

At operation 1436, a plurality of discrete line segments are generated to fit the polynomial trough line. The number of line segments may be determined according to the intended computing system, or according to a desired performance of the gate. In one embodiment, an 8 segment line may provide adequate gate selection, and be computationally manageable. Some embodiments may make use of additional or fewer segments. Some embodiments may enforce a gate directly employing the polynomial function.

The line segments may bisect the region of interest/pixel map into two gates, or additional bounding points may define gates. For example, a lower bound of a gate may be defined by the tail threshold, or in relation to the tail threshold. An upper bound of the gate may be fixed (e.g., defined by the upper surface of the region of interest), based on the density function (e.g., a minimum density, an inflection point, etc.), in relation to the critical point (e.g., a distance double the vertical distance between the tail threshold and the critical point), or otherwise defined. Additional gates may be formed, which may be non-continuous. For example, one gate could comprise the left side of the image depicted in FIG. 13C, as well as the left side of the saturated population depicted in FIG. 13B. Such non-continuous gates may be referred to as a single (non-continuous) gate, or as multiple (continuous) gates.

Figure 15A:
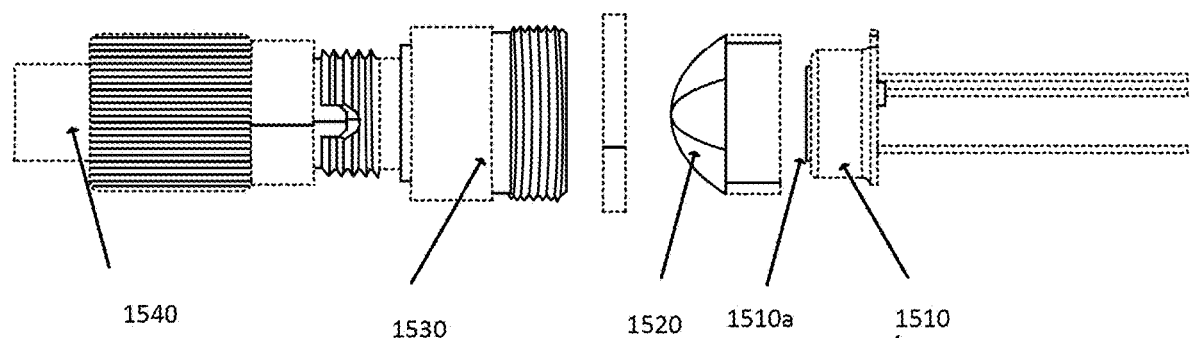
FIGS. 15A and 15B represents an example photodiode detector assembly capable of detecting florescence, in an exploded and assembled view, respectively, according to various embodiments.
Figure 15B:
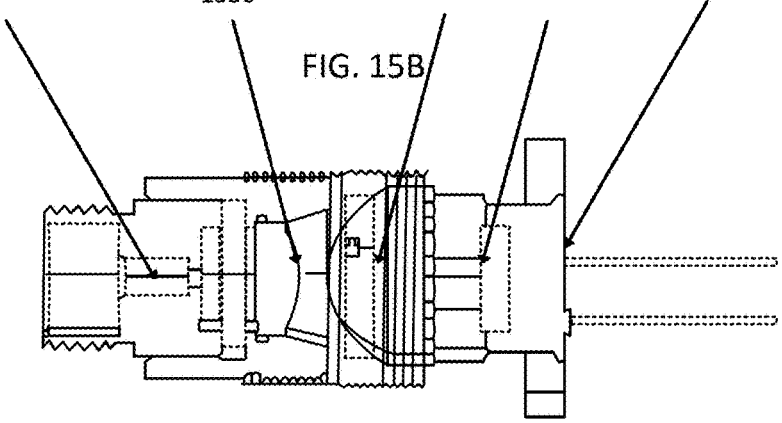

Referring to FIG. 15A, an example detector which may detect florescence from one or more directions is depicted. The detector comprises an avalanche photodiode 1510, having a light sensing surface 1510*a*. Light of various wavelengths may be focused in the avalanche photodiode 1510 by a tube lens 1520, which is configured to direct the light onto the sensor surface 1510*a*. The light entering the lens is itself aligned by a collimator 1530. The collimator 1530 receives light from an optical fiber (e.g., a low-hydroxyl (low-OH) 0.5 NA multimode fiber), which may involve an additional interface. For example, the fiber may be passed through air gaps in various bulkheads. Transmission through air gaps associated with interfaces may not be desired, a system may be designed with adequate margin that some attenuation may be acceptable with little or no impact to system operation. As one skilled in the art will understand, various optical fibers may be selected according to the desired light frequency, wavelength, etc. For example, a low-OH fiber may not be selected for certain light wavelengths. FIG. 15B depicts the assembled device of FIG. 15A.

Figure 16A:
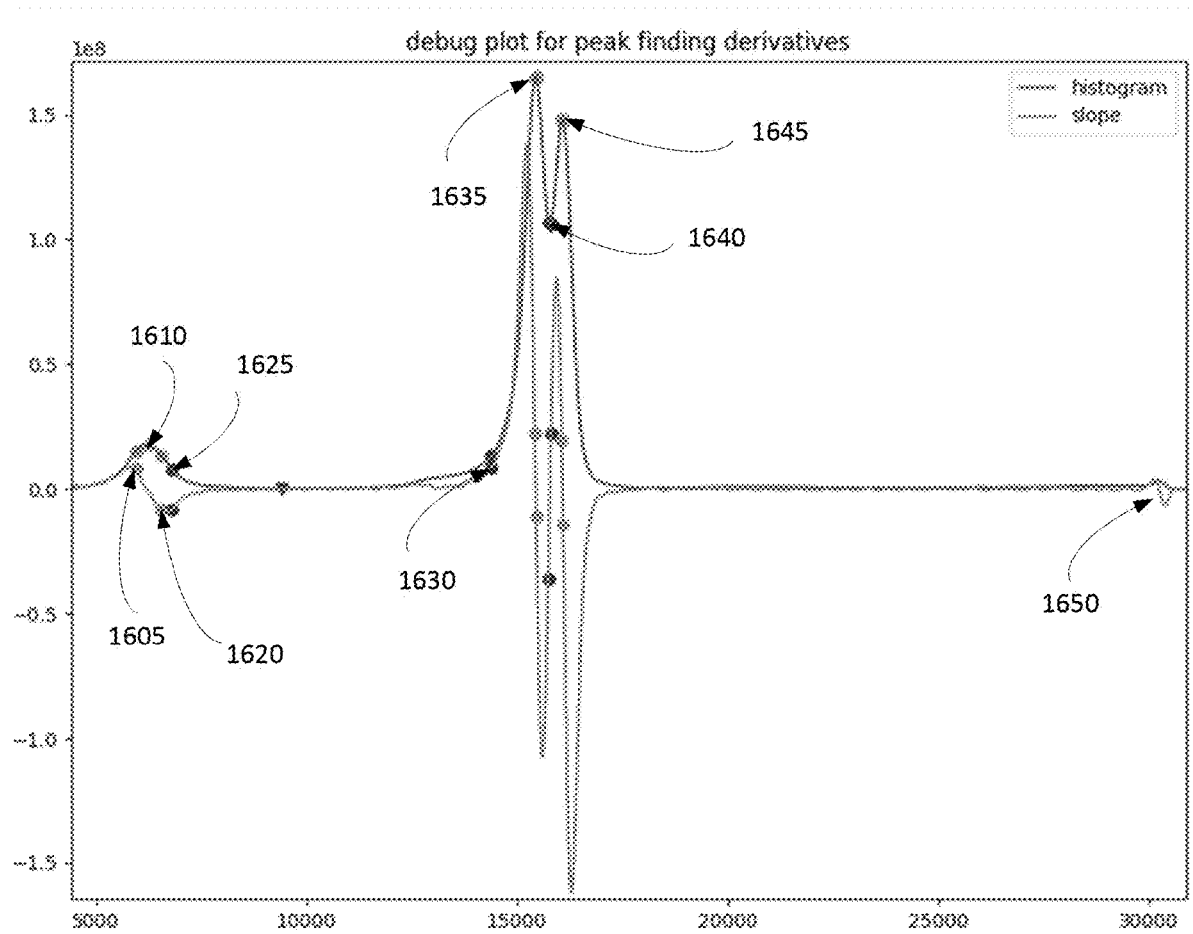
FIGS. 16A, 16B, and 16C represent a column histogram and its derivative, a plurality of points defined by the column histogram and its derivative, and a row histogram with various threshold points, respectively, according to various potential embodiments.

Referring to FIG. 16A, a debug plot showing a histogram and derivative thereof is depicted. The histogram may relate to a pixel map, such as the pixel map of FIG. 13B. At a first POI 1610, a first population peak is indicated by a maximum of the histogram and a zero of the derivative. The first POI 1610 is bounded by a first left-bound 1605, which may be determined based on the inflection point, or based on a slope and/or deviation from zero (e.g., emergence from a dead band). The first POI 1610 is also bounded on a right side. For example, a first right-bound inflection point 1620 and first right-bound dead band cutoff 1625 may define an area of interest. For example, the distance between the first POI 1610 and the right-bound dead band cutoff 1625 may be used to determine a band defining the first population, which may be known or inferred to be a population of inactive cells.

A second POI 1635 may be defined at a maximum, which may correlate to another population (e.g., a male population). A third POI 1640 may define a trough or saddle disposed between the second POI, and a fourth POI (e.g., representing a maximum of a female population). One skilled in the art will understand that various maximums and minimums may be present for various pixel maps. For example, a pixel map having two populations disposed linearly along an axis (e.g., along an X axis, referring to the side florescence of a bimodal population of male and female sperm), may have a single maximum for a histogram taken along an orthogonal axis. Another population 1650 (e.g., a saturated population) is visibly present, however no POIs are visible. This may be because the histogram and/or derivative fail to exit a dead band area, such as due to small sample size, density, etc., or may be as a result of a programmatic decision to disregard this population.

Figure 16B:
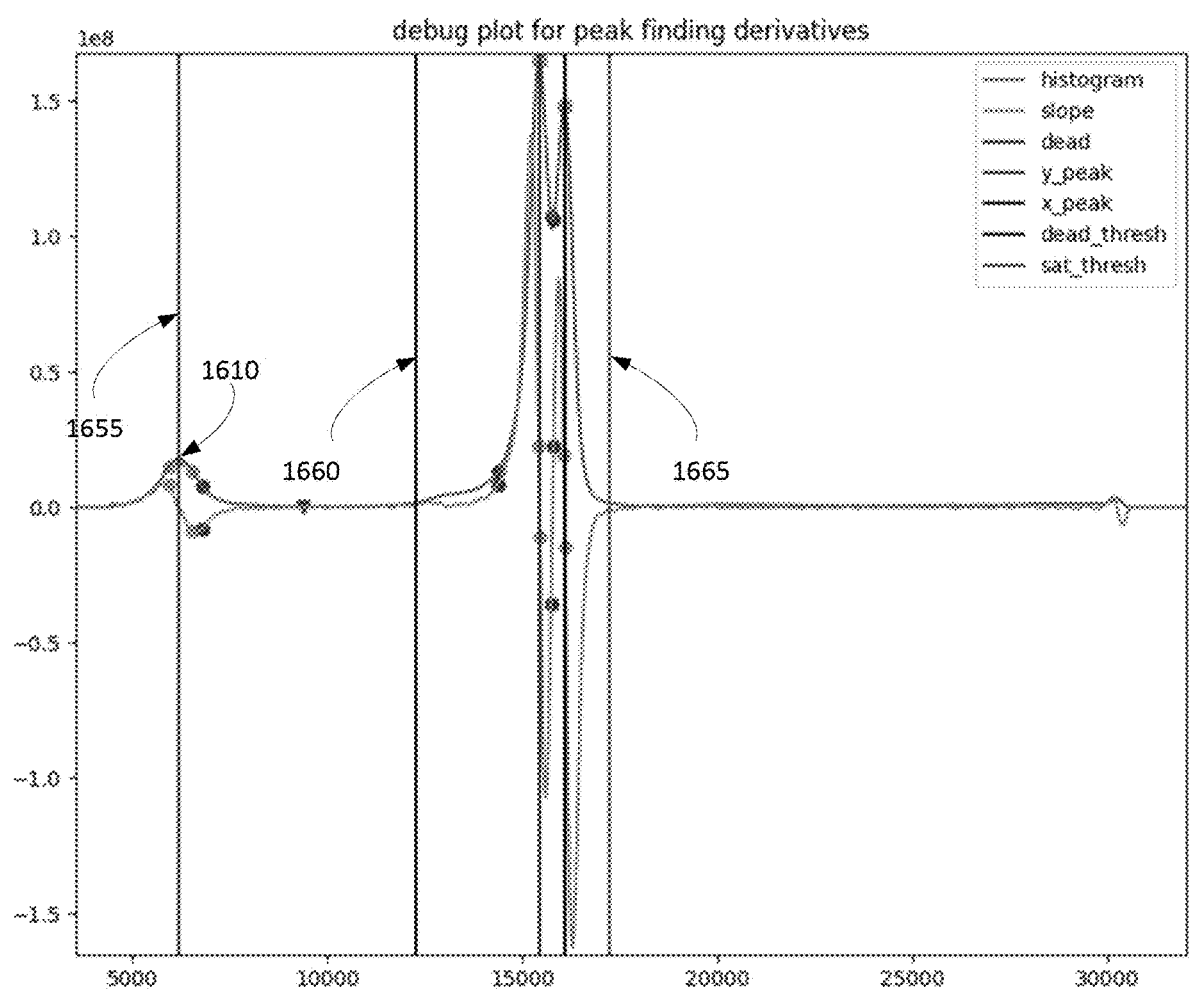

Referring now to FIG. 16B, various limits are imposed over the plot of 16A. A first population center 1655 is disposed along the peak of the density of the first POI 1610. The point may be selected according to the first histogram exceeding a minimum, being in a certain location, etc. or may further be determined according to additional constraints (e.g., disposed to the right of the first left-bound 1605, and to the right of one or more right-bounds). A first population threshold 1660 is shown disposed to the right of the first population center, which may be determined based on a location within a dead band disposed between the first population center 1655 and additional populations, which may be useful in generating future pixel maps, truncating data from a considered pixel map, etc. A second population threshold 1655 is shown as a right bound of one or more populations. For example, the second population threshold may be generated based on a return to dead band, based on additional POI, based on a pre-defined or manually entered point on the debug plot or pixel map, etc.

Figure 16C:
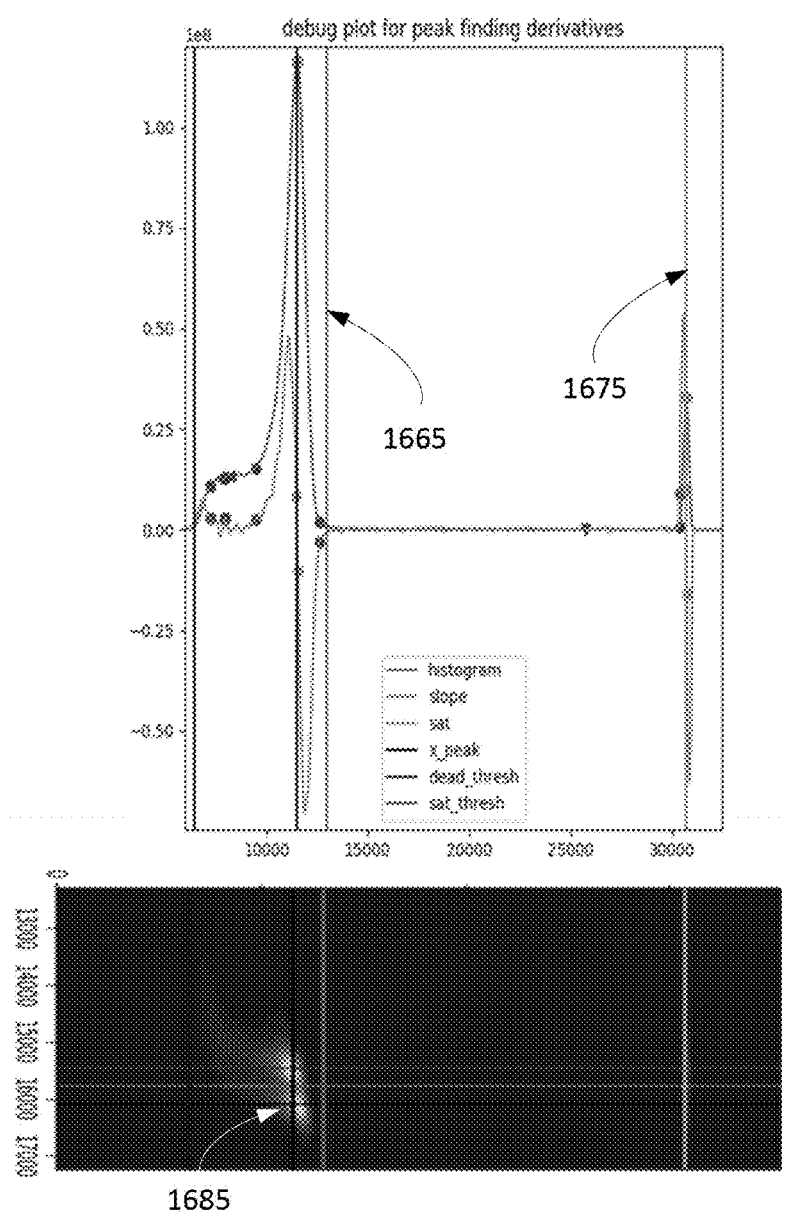

Referring to FIG. 16C, another debug plot comprising additional POIs are disclosed in conjunction with an associated pixel map. The pixel map discloses the same second population threshold as FIG. 16B, as well as a second population center 1675, which may designate a population of saturated cells. As discussed herein, such a histogram may be used for the purpose of deleting the second population from the pixel map, biasing in favor of or against the second population, etc. In some embodiments the second population may be further processed, and further defining a second population (e.g., into male and female) center 1675 may enable further processing steps.

Figure 17:
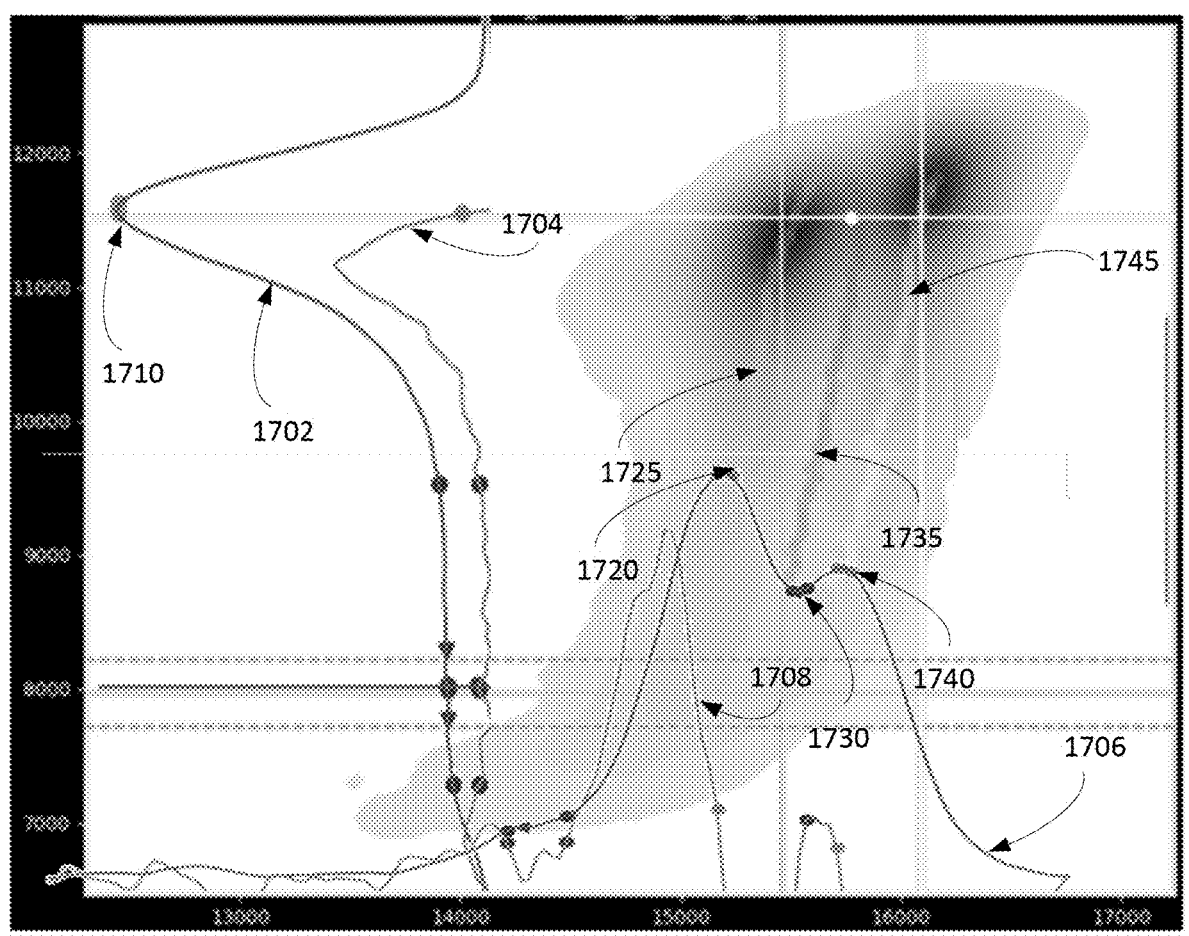
FIG. 17 represents row and column histograms of the region of interest (ROI) of the pixel map, along with their derivatives and various threshold points overlaid the image of FIG. 13C, according to various potential embodiments.

Referring to FIG. 17, the pixel map of FIG. 13C is depicted, having overlaid thereupon a first histogram 1702 along a vertical axis as well as a corresponding first derivative 1704. A vertical maximum density 1710 corresponding with population centers is also depicted. A second histogram 1706 is also overlaid along a horizontal axis as well as a corresponding first derivative 1708. The second histogram comprises a first maximum 1720, a trough point 1730, and a second maximum 1740, which may represent the density along any row(s) of the pixel diagram. These maximum and minimum points may be plotted for each row, resulting in a first maximum density line 1725, a trough line 1735, and a second maximum density line 1745.

Figure 18:
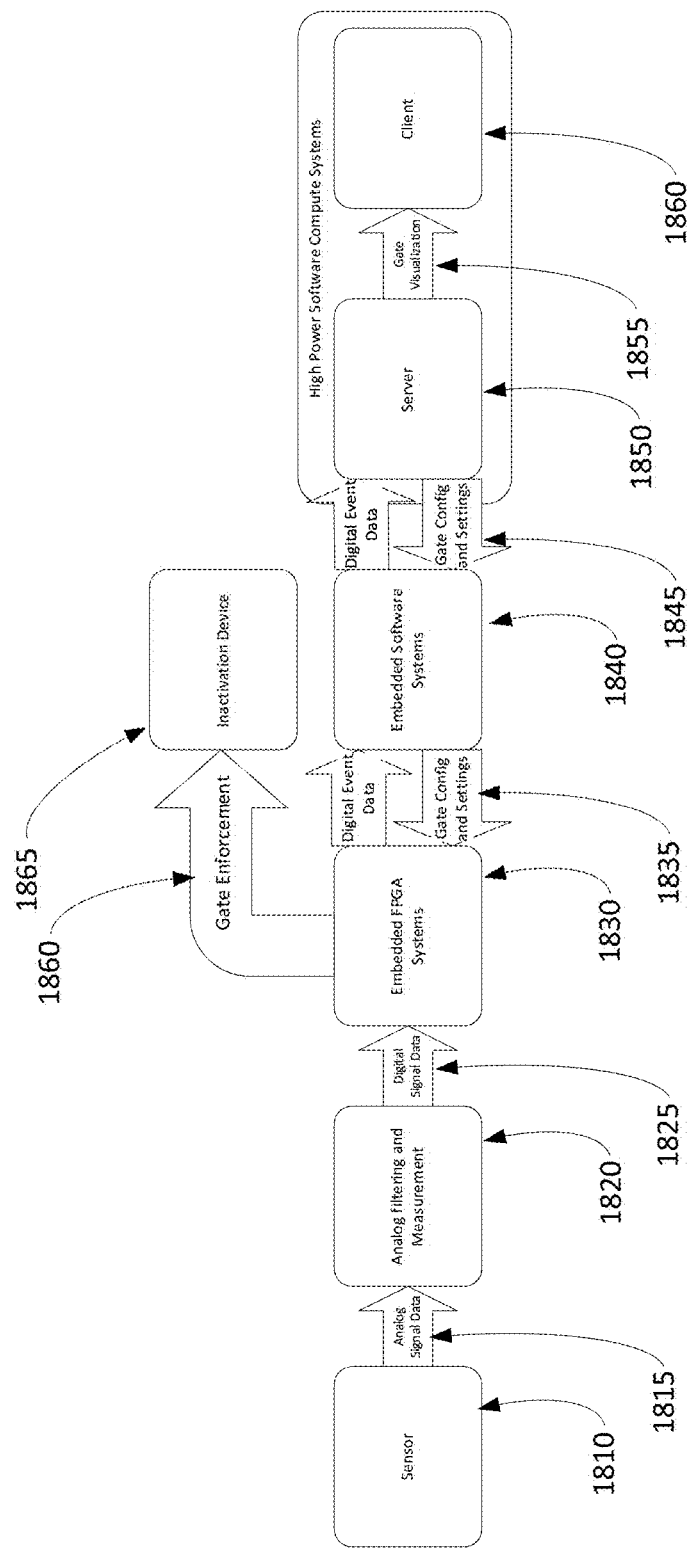
FIG. 18 represents a flow diagram of an example system configured to perform the methods disclosed by FIGS. 12 and 14, and otherwise perform portions of the disclosure according to various potential embodiments.

Referring to FIG. 18, a flow of information through a system is disclosed which may enable various methods (e.g., method 1200, method 1400, etc.). Sensors 1610 are disclosed which may be, or may include, one or more florescence sensors measuring the florescence of cells from a plurality of directions, or another sensor type, which may measure other attributes of a sample or an environment associated therewith. Sensor data may be passed in a first analog form 1815, which may minimize loss. One skilled in the art will understand that the selection of digital or analog filtering may be selected according to a particular implementation. For example, in some embodiments, if a transmission loss of an analog signal would degrade the signal, an analog to digital conversion may be undergone as soon as practical, whereas in a system with very low loss (or uniform loss) of analog signals, various filtering and processing may be undertaken on the analog signals prior to a digital conversion. In the depicted embodiment, analog filtering and measurement 1820 is performed in the transmitted analog signal, resulting in digital signal data 1825 which is input into a digital processing system, which may comprise various field-programmable-gate-arrays (FPGAs), application specific integrated circuit (ASIC) processors, and other components (e.g., an embedded FPGA system 1830), to gate various populations, sub-populations, etc. Gate enforcement data 1860 may be fed into a biasing element 1865 (e.g., a laser or other inactivation device to inactivate select cells) to bias the population.

In addition to, or instead of, gate enforcement data 1860, various data may be provided to an embedded software system 1840, which may perform real time or non-real time data analysis based on digital event data, and provide another component (e.g., the embedded FPGA system 1830) with various gate data, bounds, configuration settings, etc. In some embodiments, the embedded software system 1840 may also interface with a high power software computing system comprising a server 1850 and client (e.g., to store data, off-load certain processing, etc.). The server 1850 may in turn provide summary reports, gate visualizations 1855, prognostic or analytic data, etc. to a client for further processing, adjust various parameters, or provide visual or other presentation to a user, such as through a graphic user interface, which may present various data by graphical representation, such as the pixel maps, plots, etc. disclosed herein.

Figure 19:
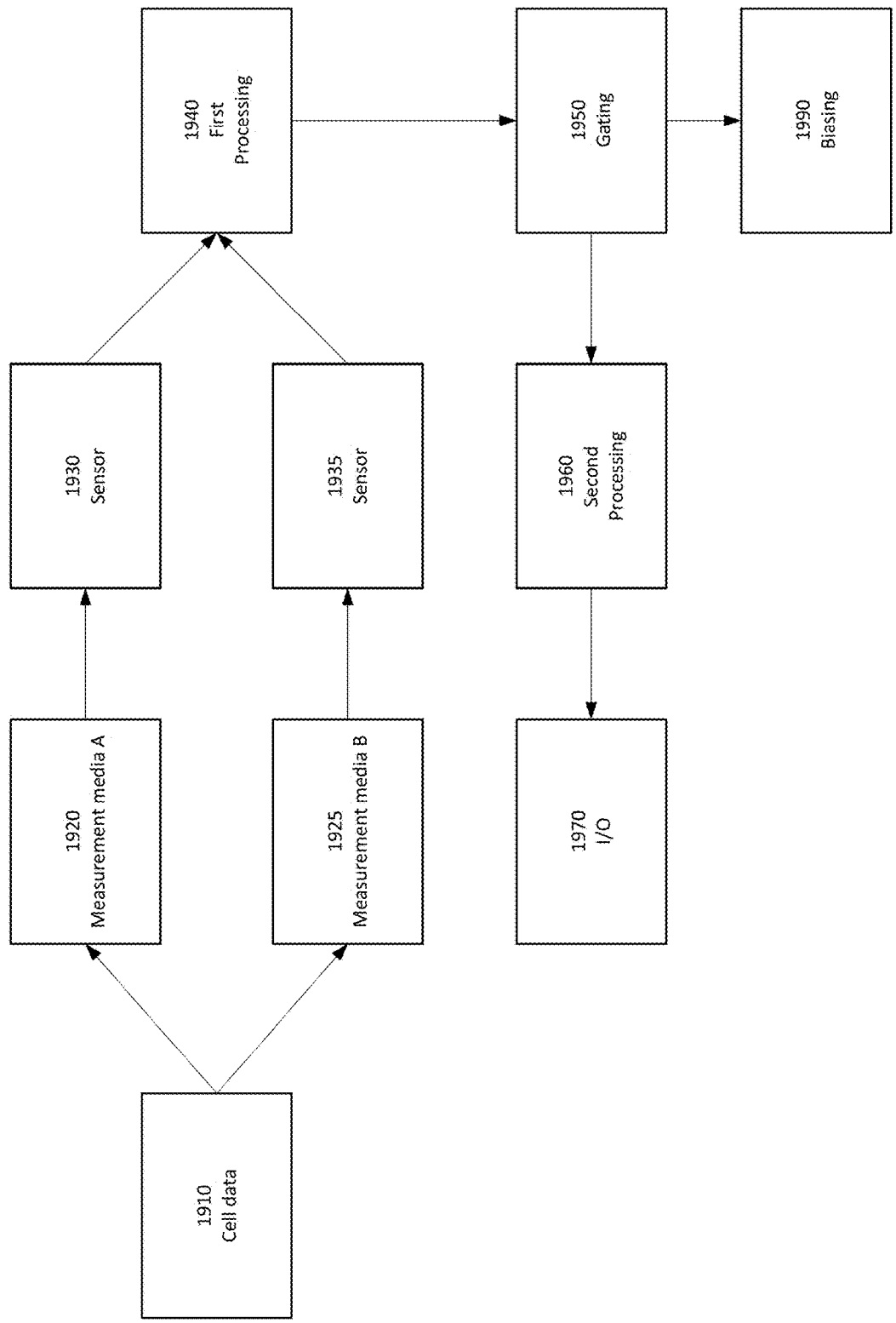
FIG. 19 represents another flow diagram of an example system configured to perform the methods disclosed by FIGS. 12 and 14, and otherwise perform portions of the disclosure according to various potential embodiments.

Referring to FIG. 19, another flow diagram is presented. Cell data 1910 is transmitted through measurement media A 1920. If a desired measurement is one of forward florescence, measurement media A 1920 may comprise various air gaps, optics, lenses, etc. The measurement media may be intended to accurately measure the cell data 1910, or to amplify certain features before passing the data to sensor A (e.g., a light sensing surface of an APD). A second measurement (e.g., side florescence) may be passed through measurement media B 1925, to sensor B 1935. Processing 1940 may be performed upon the sensor measurements, which may comprise analog to digital conversion, data analysis as herein described, etc. Such processing may define gating 1950, the location of which may indicate certain cells should be biased, which may include inactivating some cells (e.g., by a laser). In some embodiments, this inactivation laser may result in interference with sensors such as florescence sensors, resulting in certain cells indicating a saturated level of fluoresce. This saturated population, and other populations may be further processed to optimize gate locations, determine trend data, etc., by second processing 1960. In some embodiments, second processing 1960 determines all gate locations, and first processing 1940 determines whether a cell is within (or not within) a given gate. Second processing 1960 may also interface with various input/output (I/O) devices 1970, such as to a server to offload processing, or to a graphical user interface (GUI) to present various data. In some populations, gate criteria and other system parameters (e.g., parameters of first processing, gating, etc.) may be determined over I/O devices 1970.

As can be seen above, in various embodiments, using a dual-detector setup or system provides for the ability to differentiate a subset of the Y region in a histogram from an X slice of the histogram. For example, in a 2-dimensional histogram of CH2 Prominences on the X axis from 1.75 to 1.875 would cover all Y values in the X range, but the use of a second detector provides for identifying and narrowing the Y values to a subset of all Y values, for example 2.00 to 2.375. Being able to define a subset of all values can provide for the automatic definition of a gate for the Y chromosome bearing sperm population.

In various embodiments, a semen sample, such as a bovine or porcine semen sample, comprising a set or plurality of X chromosome bearing sperm cells and a set or plurality of Y chromosome bearing sperm cells may be processed by a microfluidics system comprising a dual-detector setup or system to produce a sexed or processed semen product. The sexed or processed semen product may have a "purity", or percentage of a population, set, or plurality of a desired first type of sperm cell (e.g., X chromosome sperm cells or Y chromosome sperm cells) relative to a population, set, or plurality of a second type of sperm cell (e.g., a sperm cell comprising a DNA content other than what is desired), wherein the desired purity of the first population is between 50 and 55 percent, between 55 and 60 percent, between 60 and 65 percent, between 65 and 70 percent, between 70 and 75 percent, between 75 and 80 percent, between 80 and 85 percent, between 85 and 90 percent, and between 90 and 95 percent. In various embodiments the desired purity is at least 75 percent, at least 80 percent, at least 85 percent, at least 90 percent, or at least 95 percent.

In various embodiments, a two-detection location or two-detector system may be used to more clearly understand what the X gate should look like. The X gate may be optimized to obtain, for example, a 1% to 2% improvement in X-skewing. Additional improvements may be obtained in collection efficiency of X-chromosome cells at the same skew percentage. For example, the two "comma" shaped tails in the histogram may be analyzed such that not only the "ball" or head of the X peak would be collected. The tail may also be collected at a high skew percentage to increase the overall collection percentage of X chromosome cells for higher eligibility. This analysis technique may also be applied to other "physical or positional characteristics" of other particles for increased collection percentages of a particular characteristic.

In various embodiments, the detectors are substantially 90-degree orthogonal detectors with one oriented substantially perpendicular to a face of the chip and one oriented substantially parallel to the face of the chip (e.g., through or along a side of the chip). Using two orthogonally-oriented detectors can provide for better orientation measurements when compared to a single detector. One or both detectors may be, for example, photomultiplier tubes or avalanche photodiodes.

In various embodiments, the orthogonal positional relationship between the two detectors can provide for the ability to discern both orientation and position information for cells within the flow stream. This is especially valuable information for non-symmetric particles such as sperm cells. The position and orientation information can be used to identify a subset of information from a histogram, to automatically determine a biasing for Y chromosome bearing sperm cells, and to determine the optimal microfluidic conditions (e.g., flow rate, ramps used, etc.) for non-symmetric cell alignment. For example, in one embodiment, a flow rate may be selected between about 10,000 and about 30,000 cells per second, with any particular cells having a velocity of between about 8 and about 15 meters per second. More specifically, a flow rate of between about 13,000, and about 20,000 cells per second may be selected, at a velocity between about 10 and about 12 meters per second. According to sensor sensitivity, light emissivity, and computing power, additional or fewer cells may be passed per second, and may have a higher or lower velocity.

In various embodiments, additional information that can be captured using two detectors that may be beneficial are the brightness of any signal as captured by each detector, the duration of any signal as captured by each detector, and the level or degree of synchronization for the detectors.

In various embodiments, the optical fiber used through the opening or access port in the chip may be angled and/or have a curved profile to reduce cross-talk or interference from a kill laser beam. The orthogonal fiber may be a fiber with a numerical aperture of a certain value, such as 0.4. An optical collection system with an effective numerical aperture of 0.4 could provide, in various embodiments, for collection of enough fluorescence information to use an avalanche photodiode.

In various embodiments, an important aspect in a dual detector system may be the filtering of the signal from the kill laser. A curved or curvilinear profile for the orthogonal (side port) optical fiber may provide for some or all of the required filtering of the kill laser signal. Software or an electronics-based solution may also be used. The signal from the kill laser may be filtered from the signal of the detection laser and/or fluorescence because the pulse width of the kill laser is very short. The fluorescence intensity of the kill laser is sub-microsecond in duration and a much longer fluorescence pulse is detected from a cell being hit by an excitation laser. A digital or analog electronic filter, such as a low pass filter, may be used to filter out the signal from the kill laser to obtain only the fluorescence pulse from the cell.

In various embodiments, the second (orthogonal) detector may also be used for kill confirmation. Instead of or prior to filtering the kill signal (by physical or software means), the fluorescence pulse caused by the kill laser (short micropulse) may be processed to determine if a cell has been successfully hit or deactivated based on the intensity, duration, or timing of the signal. The kill laser signal may be filtered, removed, or split from the detection laser signal (fluorescence pulse from the cell) and may be separately processed to make a kill confirmation decision. Conventional single detector systems use a masking or physical filter (e.g., diffraction grating) to filter the kill laser signal and are not readily adaptable to process both kill and detection signals as in a dual detector setup.

In various embodiments, the fiber being used is an optical fiber that is tuned or configured to the wavelength of light being collected. In various embodiments, the optical fiber in the microfluidic chip may be mounted in such a way as to provide for easy, fast, and/or simple swapping or changing of the microfluidic chip in this system. This may be an interface at the chip or a securing means for the fiber that provides for changing of the chip without "snaking" or carefully feeding in the optical fiber into position each time a chip is changed.

In various embodiments, the orthogonally-positioned dual detector system provides for the effective discrimination of Y chromosome bearing sperm cells from within a sample population. In order to separate out Y chromosome bearing sperm from a population, one may need to also separate out X chromosome bearing sperm that appear dimmer or have an orientation or positional difference when moving through the cytometer. Using a second detector (e.g., an orthogonally-positioned detector using an optical fiber) can provide valuable orientation and position information. This can provide for the differentiation of fluorescent signals due to DNA content from similar signals caused by ordination, potion, lensing, and other factors.

In various embodiments, the flow cytometry system has not more than two detectors. Such a configuration may advantageously provide the relatively smallest, most "lightweight," and inexpensive system possible in various embodiments. This reduces complexity, operator training time, calibration complexity and time, and the cost of goods for any product produced or processed by such a flow cytometry system.

As used herein, gating operations may comprise determining the "gate" or "gating" based on an analysis of data as collected by detectors. Gating may involve determining what is inside and what is outside of a determined gate. A gating operation may involve a determination of how particles are going to be processed, or determining the size or parameters of the gate. In various embodiments, a gating operation may be followed by an "action step" or "action operation" which may be, for example, an enrichment step, a selection step, a sorting step, a deactivation step, an ablation step, a killing step, etc. In various embodiments, the action may be performed after 1) a determination of the size or parameters of the gate, and 2) a determination of whether a particle is inside or outside of the gate.

Additionally, in various embodiments, a single detector gate based system may be optimized using information gathered from a dual detector based system such that it may perform better relative to a non-optimized system, but may approach the performance levels of dual detector system.

In various embodiments, information from a multi-detector system (e.g., a two-detector system) may be used to perform a biasing operation on a one-detector system. For example, in certain embodiments, a two-dimensional histogram is used to identify overlapping "tail" regions that could not be identified using a one-dimensional histogram. A gating is performed using the two detector system and this gate is used by the one-detector system. Some feedback from the one-detector system may be provided to adjust based on the specific measured operation of that system. Effectively the data from the two-detector system allows for better identification of the male and female populations in the overlapping regions. With this knowledge, the two-detector data can be re-evaluated as if the data came from a single detector system, and the gate can be mathematically optimized to increase the skew.

For example, in various embodiments, an example process may involve measuring characteristics and performing gating using a two-detector system, calculating the best gate to be used with a one-detector system based upon specific measured characteristics and operation of the two-detector system, and sort cells using the one-detector system with gate provided by two-detector system.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the terms "exemplary," "example," "potential," and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It is important to note that the construction and arrangement of the devices, assemblies, and steps as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

Some sample embodiments are disclosed below, in order to represent illusory embodiments, which one skilled in the art will understand are may be further modified, combined, constrained, etc. according to the entirety of this disclosure.

Embodiment AA: A method comprising: providing, to a microfluidic chip having a sample channel, a sample comprising a particle population having a proportion of a first particle type to a second particle type; emitting, from a light source, an illuminating light along a first axis such that the illuminating light coincides with particles in the sample as the sample passes through the channel; detecting, using a first light detector, a first light emitted from the sample along a first axis; detecting, using the first light detector or a second light detector, a second light emitted from the sample along a second axis; and performing, based on the detected first light emitted along the first axis and on the detected second light emitted along the second axis, a biasing operation that modifies the proportion of the first particle type to the second particle type.

Embodiment AB: Embodiment AA wherein the first and second particle types are two sexes of viable cells, and wherein the different particle type is an inactivated cell.

Embodiment AC: Embodiment AA or AB wherein the first light and the second light are fluorescence (i) that results from incidence of the illuminating light on particles in the sample and (ii) that travels in multiple different directions from fluorescing particles in the sample.

Embodiment AD: Any of embodiments AA to AC comprising: generating, based on the light emitted from the sample along the first and second axes, an intensity map of peak fluorescence associated with each particle type; detecting, based on the intensity map, a first population center associated with the first particle type, and a second population center associated with the second particle type; calculating a relative intensity along a first line passing through the first population center; calculating a slope of a second line joining the first population center and the second population center; locate a first saddle point along a third line joining a first population associated with the first particle type, and a second population associated with a second particle type; locate a second saddle point along a fourth line joining the first population, and the second population; generate a gate by bounding the first population or the second population, wherein the gate is bounded based on the first saddle point, the second saddle point, and additional bounding points.

Embodiment AE: Any of embodiments AA to AD comprising: calculating a kernel within a pixel map; adding a first instance of the kernel to the pixel map based on the light emitted from the sample along the first and second axes; adding a second instance of the kernel to the pixel map based on the light emitted from the sample along the first and second axes; deriving a first histogram from the pixel map; removing data from the pixel map; deriving a second histogram from a first row of the pixel map; generating a first trough point from the second histogram; deriving a third histogram from a second row of the pixel map; generating a second trough point from the third histogram; generating a polynomial function based on the first and second trough points; bounding a population based on the polynomial function and additional bounding points.

Embodiment AF: Any of embodiments AA to AE wherein the first axis makes an angle with respect to the second axis, and wherein the angle is between 45 degrees and 135 degrees.

Embodiment AG: Any of embodiments AA to AF wherein the angle is between 75 degrees and 105 degrees.

Embodiment AH: Any of embodiments AA to AG wherein the angle is between 85 degrees and 95 degrees.

Embodiment AI: Any of embodiments AA to AH wherein the first axis is orthogonal to the second axis.

Embodiment AJ: Any of embodiments AA to AI wherein the first axis and the second axis are along a same direction, and wherein a beam splitter or a dichroic mirror is used to observe, using the first detector, the first and second lights based on differences in wavelength.

Embodiment AK: Any of embodiments AA to AJ wherein the first light is detected using the first detector situated at a first position along the first axis, and wherein the second light is detected using the second detector situated at a second position along the second axis.

Embodiment AL: Any of embodiments AA to AK wherein no more than two detectors are used to detect light emissions from the sample.

Embodiment AM: Any of embodiments AA to AL wherein (i) the first light is detected using the first detector situated at a first position along the first axis, and wherein (ii) the second light is detected using the first detector via a fiber optic element that transmits light from a second position along the second axis to the first position along the first axis.

Embodiment AN: Any of embodiments AA to AM wherein the first detector comprises an multiple pixel photodetector with a first pixel detection region and a second pixel detection region, and wherein the method further comprises determining, based on intensities of the first and second lights at the first and second pixel detection regions, respectively, a physical positional characteristic of each particle.

Embodiment AO: Any of embodiments AA to AN wherein the biasing operation comprises emitting, using a second light source, a third light at the sample to change states of individual particles in the sample.

Embodiment AP: Any of embodiments AA to AO wherein the third light is emitted to activate a particle in the sample.

Embodiment AQ: Any of embodiments AA to AP wherein the particle is of the first particle type, and wherein activating the particle using the third light transforms the particle to the second particle type.

Embodiment AR: Any of embodiments AA to AQ wherein the second light is emitted to deactivate a particle in the sample.

Embodiment AS: Any of embodiments AA to AR wherein the illuminating light coincides with the sample at a first location in a path of the sample flowing through the sample channel, and wherein the third light is emitted at the sample so as to coincide with the sample at a second location in the path of the sample, wherein the second location is downstream of the first location.

Embodiment AT: Any of embodiments AA to AS comprising determining an orientational feature of each particle in a set of one or more particles in the sample.

Embodiment AU: Any of embodiments AA to AT wherein the orientational feature is determined based on the detected first light and on the detected second light.

Embodiment AV: Any of embodiments AA to AU wherein the biasing operation is performed on each particle based on its orientational feature.

Embodiment AW: Any of embodiments AA to AV wherein the particle population is a cell population, wherein the first particle type is a first cell type, and wherein the second particle type is a second cell type.

Embodiment AX: Any of embodiments AA to AW comprising determining an orientational feature of each cell in the sample based on the detected first light and on the detected second light.

Embodiment AY: Any of embodiments AA to AX wherein the orientational feature comprises a relative orientation of a primary surface of each cell with respect to the second axis.

Embodiment AZ: Any of embodiments AA to AY wherein the primary surface of each cell is a flat side of the cell or an edge side of the cell.

Embodiment AAA: Any of embodiments AA to AZ wherein the first cell type is a male sperm cell with a Y chromosome and the second cell type is a female sperm cell without the Y chromosome.

Embodiment AAB: Any of embodiments AA to AAA wherein the proportion, as modified by the biasing operation, comprises more male sperm cells relative to female sperm cells.

Embodiment AAC: Any of embodiments AA to AAB wherein performing the biasing operation comprises deactivating female sperm cells in the sample.

Embodiment AAD: Any of embodiments AA to AAC wherein the light source is a laser having a first wavelength, and wherein the first and second lights are fluorescence with a second wavelength that is different from the first wavelength.

Embodiment AAE: Any of embodiments AA to AAD wherein the light source is a first light source, and wherein performing the biasing operation comprises using a second light source to emit light at the sample to change a state of particles of either the first particle type or of the second particle type in the sample.

Embodiment AAF: Any of embodiments AA to AAE wherein the biasing operation is performed based on fluorescence detected along the first axis in combination with fluorescence detected along the second axis.

Embodiment AAG: Any of embodiments AA to AAF comprising generating a histogram of intensity along the first and second axes, and identifying a region in the histogram corresponding with particles of the first type or particles of the second type.

Embodiment AAH: Any of embodiments AA to AAG wherein the first light and the second light are fluorescence of particles in the sample, and wherein the histogram corresponds to fluorescence intensity along the first and second axes.

Embodiment AAI: Any of embodiments AA to AAH wherein the first light and the second light are fluorescence, further comprising (i) determining an orientational feature of each particle in a set particles in the sample based on the detected first light and on the detected second light, (ii) generating a histogram of fluorescence intensity in the first and second axes, and (iii) identifying a region in the histogram corresponding with particles having a first orientational feature and particles having a second orientational feature.

Embodiment AAJ: Any of embodiments AA to AAI wherein the method is implemented on a first microfluidics system in which light is detected in multiple directions, and wherein the method further comprises performing, on a second microfluidics system without multi-directional light detection, a second biasing operation based on the identified region.

Embodiment AAK: Any of embodiments AA to AAJ wherein the microfluidic chip further comprises an access port via which the second light emitted along the second axis is collected.

Embodiment AAL: Any of embodiments AA to AAK wherein the access port of the microfluidic chip comprises a fiber optic element for transmitting the second set of lights.

Embodiment AAM: Any of embodiments AA to AAL wherein the fiber optic element terminates in a beam splitting element configured to separate a fluorescence wavelength from a wavelength corresponding to the illuminating light source.

Embodiment AAN: Any of embodiments AA to AAM comprising performing a gating operation based on the detected first light emitted along the first axis and on the detected second light emitted along the second axis.

Embodiment AAO: Any of embodiments AA to AAN wherein the gating operation affects a hydrodynamic flow of the sample in the microfluidic chip.

Embodiment AAP: Any of embodiments AA to AAO wherein the biasing operation requires both the detected first light and the detected second light in order to modify the proportion of the first particle type to the second particle type.

Embodiment AAQ: Any of embodiments AA to AAP comprising calculating a kernel within a pixel map; adding a pre-defined number of instances of the kernel to the pixel map based on the light emitted from a plurality of samples along the first and second axes; deriving a first histogram from the pixel map along the first axis; removing data from the pixel map, based on the first histogram; generating a second histogram from the pixel map along the second axis; determining an area of interest within the pixel map, based on the second histogram; generating an additional plurality of histograms along the second axis of the area of interest of the pixel map; determining a plurality of trough points based on the additional plurality of histograms; generating a polynomial function based on the plurality of trough points; bounding a population based on the polynomial function and additional bounding points.

Embodiment BA: A product comprising the particle population having the modified proportion of the first particle type to the second particle type produced according to the method of embodiments AA to AAP.

Embodiment CA: A method comprising: providing a sample to a microfluidic chip having a sample channel, the sample comprising a particle population having a first proportion of a first particle type to a second particle type; emitting, using an illuminating light source, a coherent light along an illumination axis such that the coherent light coincides with the sample as the sample passes through the channel; detecting, using a first light detector at a first location along a first direction from the microfluidic chip, a first set of one or more lights at one or more wavelengths traveling from the sample in the first direction; detecting, using a second light detector at the first location or at a second location along a second direction from the microfluidic chip, a second set of one or more lights at one or more wavelengths traveling from the sample in the second direction; and performing, based on the first set of lights and the second set of lights, a biasing operation so as to obtain a modified particle population having a second proportion of the first particle type to the second particle type.

Embodiment CB: Embodiment CA wherein the first set of lights comprises fluorescence in the first direction from particles in the sample, and wherein the second set of lights comprises fluorescence in the second direction from particles in the sample.

Embodiment CC: Embodiment CA or CB wherein the illuminating light incident on particles in the sample results in fluorescence of the particles in the sample.

Embodiment CD: Any of embodiments CA to CC wherein the biasing operation comprises a gating operation affecting sample flow in the microfluidic chip.

Embodiment CE: Any of embodiments CA to CD wherein the biasing operation comprises emitting a second coherent light at the sample.

Embodiment CF: Any of embodiments CA to CE wherein the second coherent light is emitted using a second light source.

Embodiment CG: Any of embodiments CA to CF wherein the second coherent light has a wavelength that is lower than the wavelength of the first coherent light.

Embodiment CH: Any of embodiments CA to CG wherein the first coherent light coincides with the sample at a first location along a path of sample flow, and wherein the second coherent light is emitted to coincide with the sample at a second location along the path that is downstream of the first location.

Embodiment CI: Any of embodiments CA to CH wherein the second coherent light activates particles in the sample.

Embodiment CJ: Any of embodiments CA to CI wherein the second coherent light deactivates particles in the sample.

Embodiment CK: Any of embodiments CA to CJ wherein the first light detector is a first pixel detection region of a detector module, and the second detector is a second pixel detection region of the detector module.

Embodiment CL: Any of embodiments CA to CK comprising determining, based on intensities of the first and second lights at the first and second pixel detection regions, respectively, a physical positional characteristic of each particle.

Embodiment CM: Any of embodiments CA to CL wherein the particle population is a cell population, wherein the first particle type is a first cell type, and wherein the second particle type is a second cell type.

Embodiment CN: Any of embodiments CA to CM comprising determining an orientational feature of a plurality of cells in the sample.

Embodiment CO: Any of embodiments CA to CN wherein the orientational feature is determined based on the detected first set of lights and on the detected second set of lights.

Embodiment CP: Any of embodiments CA to CO wherein the biasing operation is performed (i) on each of the plurality of cells, and (ii) additionally based on the orientational feature of each of the plurality of cells.

Embodiment CQ: Any of embodiments CA to CP wherein the first cell type is a male sperm cell with a Y chromosome and the second cell type is a female sperm cell without the Y chromosome, or wherein the first cell type is a female sperm cell with an X chromosome and the second cell type is a male sperm cell without the X chromosome.

Embodiment CR: Any of embodiments CA to CQ wherein the orientational features of the plurality of cells comprise (i) a first orientation corresponding to a primary surface of cells facing the illumination access, and (ii) a second orientation corresponding to a secondary surface of cells oriented facing the illumination axis.

Embodiment CS: Any of embodiments CA to CR wherein the orientational features of the plurality of cells comprise (i) a first orientation corresponding to cells oriented flat side to at least one of the first detector or the second detector, and (ii) a second orientation corresponding to cells oriented edge side to at least one of the first detector or the second detector.

Embodiment CT: Any of embodiments CA to CS wherein the orientational features of the plurality of cells further comprise a third orientation corresponding to cells orientated transitionally between the edge side and flat side.

Embodiment CU: Any of embodiments CA to CT wherein the second proportion is greater than the first proportion such that the modified cell population has more male sperm cells relative to female sperm cells as a result of the biasing operation.

Embodiment CV: Any of embodiments CA to CU wherein performing the biasing operation comprises deactivating one or more cells of the first cell type or of the second cell type in the sample.

Embodiment CW: Any of embodiments CA to CV wherein the first set of lights comprises at least one of light scatter or fluorescence in the first direction, and the second set of lights comprises at least one of light scatter or fluorescence in the second direction.

Embodiment CX: Any of embodiments CA to CW wherein the illuminating light source is a laser having a first wavelength, and wherein the fluorescence has a second wavelength that is different from the first wavelength.

Embodiment CY: Any of embodiments CA to CX wherein performing the biasing operation comprises changing a state of one or more particles of the first particle type or of the second particle type in the sample.

Embodiment CZ: Any of embodiments CA to CY wherein the biasing operation is performed based on fluorescence detected in the first direction in combination with fluorescence detected in the second direction.

Embodiment CAA: Any of embodiments CA to CZ wherein the biasing operation is performed based on (i) fluorescence in the first direction, and on (ii) both light scatter and fluorescence in the second direction.

Embodiment CAB: Any of embodiments CA to CAA comprising generating a histogram of fluorescence intensity in the first and second directions, and identifying a region in the histogram corresponding with particles of the first cell type or particles of the second cell type.

Embodiment CAC: Any of embodiments CA to CAB comprising generating a histogram of fluorescence intensity in the first and second directions, and identifying a region in the histogram corresponding with particles having a first orientational feature and particles having a second orientational feature.

Embodiment CAD: Any of embodiments CA to CAC comprising generating a histogram of fluorescence intensity in the first and second directions, and identifying a region in the histogram corresponding with at least one of (i) particles of the first cell type, (ii) particles of the second cell type, (iii) particles having a first orientational feature, or (iv) particles having a second orientational feature.

Embodiment CAE: Any of embodiments CA to CAD wherein the method is implemented on a first microfluidics system in which light is detected in multiple directions, and wherein the method further comprises performing, on a second microfluidics system without multi-directional light detection, a second biasing operation based on the identified region.

Embodiment CAF: Any of embodiments CA to CAE wherein the first direction is along the illumination axis, and the second direction is along a second axis that is angled with respect to the illumination axis.

Embodiment CAG: Any of embodiments CA to CAF wherein the second direction is orthogonal to the illumination axis.

Embodiment CAH: Any of embodiments CA to CAG wherein the second direction is at an angle with respect to the illumination axis, and wherein the angle is between 45 degrees and 135 degrees Embodiment CAI: Any of embodiments CA to CAH wherein the microfluidic chip further comprises an access port via which the second set of lights is collected.

Embodiment CAJ: Any of embodiments CA to CAI wherein the access port of the microfluidic chip comprises a fiber optic element for transmitting the second set of lights.

Embodiment CAK: Any of embodiments CA to CAJ wherein the fiber optic element terminates in a beam splitting element configured to separate a fluorescence wavelength from a wavelength corresponding to the illuminating light source.

Embodiment CAL: Any of embodiments CA to CAK further comprising filtering a third set of lights from a second illuminating light source.

Embodiment CAM: Any of embodiments CA to CAL wherein the filtering further comprises filtering by an optical fiber defined by a length having a curvilinear shape.

Embodiment CAN: Any of embodiments CA to CAM comprising determining a deactivation of a particle in the sample based on detecting a characteristic of the third set of lights.

Embodiment CAO: Any of embodiments CA to CAN comprising changing, based on the modified cell population, at least one of (i) the microfluidic chip or (ii) a manner in which the sample is provided to the microfluidic chip so as to obtain a third proportion of the first particle type to the second particle type.

Embodiment CAP: Any of embodiments CA to CAO comprising collecting the sample via the channel following the biasing operation.

Embodiment DA: A product comprising the modified particle population having the second proportion of the first particle type to the second particle type produced according to the embodiments AA to CAO.

Embodiment EA: A flow cytometry system comprising: an illuminating light source configured to emit coherent light that has a first wavelength and that coincides with a sample channel of a microfluidic chip; a first light detector that is configured to detect light traveling from the sample channel in a first direction; a second light detector that is configured to detect light traveling from the sample channel in a second direction; and a control unit configured to: (i) illuminate a sample passing through the sample channel of the microfluidic chip, the sample comprising a cell population with a first proportion of a first cell type to a second cell type, (ii) detect a first light using the first light detector and a second light using the second light detector, and (iii) control one or more biasing mechanisms to perform, based on both the first light detected using the first light detector and the second light detected using the second light detector, a biasing operation to modify the cell population to obtain a second proportion of the first cell type to the second cell type.

Embodiment EB: Embodiment EA comprising the microfluidic chip, wherein the microfluidic chip comprises an access port with a fiber optic element through which the second light travels to reach the second detector.

Embodiment EC: Embodiment EA or EB wherein the first direction is an illumination axis of the illuminating light source and the second detector is positioned to detect light that is at an angle with respect to the illumination axis.

Embodiment ED: Any of embodiments EA to EC wherein the angle is between 45 degrees and 135 degrees.

Embodiment EE: Any of embodiments EA to ED wherein the first direction is an illumination axis of the illuminating light source and the second detector is positioned to detect light that travels orthogonally to the illumination axis.

Embodiment EF: Any of embodiments EA to EE wherein the one or more biasing mechanisms comprises a second laser having a higher intensity or lower wavelength relative to the illuminating laser, and wherein the control unit is further configured to use the second laser to deactivate one or more cells of the first cell type or of the second cell type in the sample.

Embodiment EG: Any of embodiments EA to EF wherein the one or more biasing mechanisms comprises an actuator affecting sample flow in the microfluidic chip.

Embodiment EH: Any of embodiments EA to EG wherein the control unit is configured to perform the biasing operation based on forward fluorescence detected using the first detector and side fluorescence detected using the second detector.

Embodiment EI: Any of embodiments EA to EH wherein the control unit is further configured to generate a histogram of fluorescence intensity in the first and second directions.

Embodiment EJ: Any of embodiments EA to EI wherein the control unit is further configured to identify a region in the histogram corresponding with at least one of (i) particles of the first cell type, (ii) particles of the second cell type, (iii) particles having a first orientational feature, or (iv) particles having a second orientational feature.

Embodiment EK: Any of embodiments EA to EJ wherein the control unit is further configured to control, based on the identified region, the one or more biasing mechanisms to perform, using only detected light traveling in the first direction not the second direction, a second biasing operation for a second sample.

Embodiment FA: A microfluidic chip comprising: a sample channel extending from a sample inlet to a sample outlet and configured to receive a sample comprising a cell population; an access port extending from an opening in the microfluidic chip to the sample channel; and a fiber optic element that is situated in the access port and is configured to transmit wavelengths of light having wavelengths corresponding to at least one of light scatter and fluorescence from a sample passing through the sample channel; wherein the microfluidic chip is configured for illumination of the sample using an illumination laser along an illumination axis, and is configured for collection of light emitted co-axially to the illumination axis; wherein the fiber optic element is configured to collect light emitted orthogonally from cells illuminated using the illumination laser; and wherein an orientational feature of a cell in the cell population of the sample are derivable from light collected by the fiber optic element and from light collected co-axially to the illumination axis.

Embodiment FB: Embodiment FA comprising a beam splitting element configured to separate fluorescence wavelengths of light from scatter wavelengths of light transmitted through the fiber optic element.

Embodiment FC: Embodiment FA or FB wherein the orientational feature of the cell in the cell population of the sample is a relative orientation of a primary surface of the particle to the illumination axis.

Embodiment GA: A product comprising a modified cell population having a modified proportion of a first cell type to a second cell type produced according to a method comprising: providing a sample to a microfluidic chip having a sample channel, the sample comprising a cell population having an initial proportion of the first cell type to the second cell type; emitting, using an illuminating light source, a coherent light along an illumination axis such that the coherent light coincides with the sample as the sample passes through the channel; detecting, in a first direction from the microfluidic chip and at a first location, using a first light detector at the first location, a first set of one or more lights at one or more wavelengths; detecting, in a second direction from the microfluidic chip and at a second location, using a second light detector at the second location, a second set of one or more lights at one or more wavelengths; determining at least one of an orientation or a position for each cell in the sample based on the detected first set of lights and the detected second set of lights; and performing, based on (i) the determined at least one of the orientation or the position and (ii) at least one of the detected first set of lights and the detected second set of lights, a biasing operation so as to obtain the modified cell population having the modified proportion of the first cell type to the second cell type.

Embodiment GB: Embodiment GA wherein the first cell type is a male sperm cell with a Y chromosome and the second cell type is a female sperm cell without the Y chromosome.

Embodiment GC: Embodiment GA or GB wherein the modified proportion is greater than the initial proportion such that the modified cell population has more male sperm cells relative to female sperm cells as a result of the biasing operation.

Embodiment GD: Any of embodiments GA to GC wherein the illuminating light source is a laser having a first wavelength, and wherein the fluorescence has a second wavelength that is different from the first wavelength.

Embodiment GE: Any of embodiments GA to GD wherein performing the biasing operation comprises ablating one or more cells of the first cell type or of the second cell type in the sample.

Embodiment GF: Any of embodiments GA to GE wherein the biasing operation is performed based on fluorescence detected in the first direction in combination with fluorescence detected in the second direction.

Embodiment GG: Any of embodiments GA to GF wherein the biasing operation is performed based on (i) fluorescence in the first direction, and on (ii) both light scatter and fluorescence in the second direction.

Embodiment GH: Any of embodiments GA to GG wherein the method further comprises generating a histogram of fluorescence intensity in the first and second directions, and identifying a region in the histogram corresponding with cells of the first cell type or cells of the second cell type.

Embodiment GI: Any of embodiments GA to GH wherein the first direction is along the illumination axis, and the second direction is along a second axis that is angled with respect to the illumination axis.

Embodiment GJ: Any of embodiments GA to GI wherein the second direction is orthogonal to the illumination axis.

Embodiment GK: Any of embodiments GA to GJ wherein the second direction is at an angle with respect to the illumination axis, and wherein the angle is between 45 degrees and 135 degrees.

Embodiment GL: Any of embodiments GA to GK wherein the microfluidic chip further comprises an access port via which the second set of lights is collected.

Embodiment GM: Any of embodiments GA to GL wherein the access port of the microfluidic chip comprises a fiber optic element for transmitting the second set of lights.

Embodiment GN: Any of embodiments GA to GM wherein the fiber optic element terminates in a beam splitting element configured to separate a fluorescence wavelength from a wavelength corresponding to the illuminating light source.

Embodiment GO: Any of embodiments GA to GN wherein the method further comprises filtering a third set of lights from a second illuminating light source.

Embodiment GP: Any of embodiments GA to GO wherein the filtering further comprises filtering by an optical fiber defined by a length having a curvilinear shape.

Embodiment GQ: Any of embodiments GA to GP wherein the method further comprises determining a deactivation of a cell in the sample based on the third set of lights.

Embodiment GR: Any of embodiments GA to GQ wherein the method further comprises filtering a third set of lights from a second illuminating light source.

Embodiment GS: Any of embodiments GA to GR wherein the filtering further comprises filtering by an optical fiber defined by a length having a curvilinear shape.

Embodiment GT: Any of embodiments GA to GS wherein the method further comprises determining a deactivation of a cell in the sample based on the third set of lights.

Embodiment HA: A method comprising: emitting, using an illuminating light source, a coherent light such that the coherent light coincides with a sample as the sample passes through a sample channel of a microfluidic chip, the sample comprising a cell population having a first proportion of a first cell type to a second cell type; detecting, in a first direction from the microfluidic chip and at a first location, using a first light detector at the first location, a first set of one or more lights at one or more wavelengths; detecting, in a second direction from the microfluidic chip and at a second location, using a second light detector at the second location, a second set of one or more lights at one or more wavelengths; determining an orientational feature of a plurality of cells in the sample based on the first set of lights and the second set of lights; and performing, based on (i) the orientational features of the plurality of cells and (ii) at least one of the first set of lights or the second set of lights, a biasing operation so as to obtain a modified cell population having a second proportion of the first cell type to the second cell type.

Embodiment HB: Embodiment HA wherein the first cell type is a male sperm cell with a Y chromosome and the second cell type is a female sperm cell without the Y chromosome.

Embodiment HC: Embodiment HA or HB wherein the second proportion is greater than the first proportion such that the modified cell population has more male sperm cells relative to female sperm cells as a result of the biasing operation.

Embodiment HD: Any of embodiments HA to HC wherein the orientational features of the plurality of cells comprise (i) a first orientation corresponding to cells oriented flat side to at least one of the first detector or the second detector, and (ii) a second orientation corresponding to cells oriented edge side to at least one of the first detector or the second detector.

Embodiment HE: Any of embodiments HA to HD wherein the orientational features of the plurality of cells further comprise a third orientation corresponding to cells orientated transitionally between the edge side and flat side.

Embodiment HF: Any of embodiments HA to HE wherein the first set of lights comprises at least one of light scatter or fluorescence in the first direction, and the second set of lights comprises at least one of light scatter or fluorescence in the second direction.

Embodiment HG: Any of embodiments HA to HF wherein the illuminating light source is a laser having a first wavelength, and wherein the fluorescence has a second wavelength that is different from the first wavelength.

Embodiment HH: Any of embodiments HA to HG wherein performing the biasing operation comprises ablating one or more cells of the first cell type or of the second cell type in the sample.

Embodiment HI: Any of embodiments HA to HH wherein the biasing operation is performed based on fluorescence detected in the first direction and fluorescence detected in the second direction.

Embodiment HJ: Any of embodiments HA to HI further comprising generating a histogram of fluorescence intensity in the first and second directions, and identifying at least one of (i) a first region in the histogram corresponding with cells of the first cell type or cells of the second cell type, or (ii) a second region in the histogram corresponding with cells having a first orientational feature and cells having a second orientational feature.

Embodiment HK: Any of embodiments HA to HJ comprising: generating, based on the light emitted from the sample along the first and second axes, an intensity map of peak fluorescence associated with each particle type; detecting, based on the intensity map, a first population center associated with the first particle type, and a second population center associated with the second particle type; calculating a relative intensity along a first line passing through the first population center; calculating a slope of a second line joining the first population center and the second population center; locate a first saddle point along a third line joining a first population associated with the first particle type, and a second population associated with a second particle type; locate a second saddle point along a fourth line joining the first population, and the second population; generate a gate by bounding the first population or the second population, wherein the gate is bounded based on the first saddle point, the second saddle point, and additional bounding points.

Embodiment HI: Any of embodiments HA to HK comprising: calculating a kernel within a pixel map; adding a first instance of the kernel to the pixel map based on the light emitted from the sample along the first and second axes; adding a second instance of the kernel to the pixel map based on the light emitted from the sample along the first and second axes; deriving a first histogram from the pixel map; removing data from the pixel map; deriving a second histogram from a first row of the pixel map; generating a first trough point from the second histogram; deriving a third histogram from a second row of the pixel map; generating a second trough point from the third histogram; generating a polynomial function based on the first and second trough points; bounding a population based on the polynomial function and additional bounding points.

What is claimed is:

1. A method comprising:
providing, to a microfluidic chip having a sample channel, a sample comprising a particle population having a proportion of a first particle type to a second particle type;
emitting, from a light source, an illuminating light along a first axis such that the illuminating light coincides with particles in the sample as the sample passes through the channel;
detecting, using a first light detector, a first light emitted from the sample along a first axis;

detecting, using the first light detector or a second light detector, a second light emitted from the sample along a second axis; and performing, based on the detected first light emitted along the first axis and on the detected second light emitted along the second axis, a biasing operation that modifies the proportion of the first particle type to the second particle type;

wherein the first light and the second light are fluorescence (i) that results from incidence of the illuminating light on particles in the sample and (ii) that travels in multiple different directions from fluorescing particles in the sample, and wherein the method further comprises:

generating, based on the light emitted from the sample along the first and second axes, an intensity map of peak fluorescence associated with each particle type;

detecting, based on the intensity map, a first population center associated with the first particle type, and a second population center associated with the second particle type;

calculating a relative intensity along a first line passing through the first population center;

calculating a slope of a second line joining the first population center and the second population center;

locating a first saddle point along a third line joining a first population associated with the first particle type, and a second population associated with a second particle type;

locating a second saddle point along a fourth line joining the first population, and the second population; and generating a gate by bounding the first population or the second population, wherein the gate is bounded based on the first saddle point, the second saddle point, and additional bounding points.

2. A method comprising:

providing, to a microfluidic chip having a sample channel, a sample comprising a particle population having a proportion of a first particle type to a second particle type;

emitting, from a light source, an illuminating light along a first axis such that the illuminating light coincides with particles in the sample as the sample passes through the channel;

detecting, using a first light detector, a first light emitted from the sample along a first axis;

detecting, using the first light detector or a second light detector, a second light emitted from the sample along a second axis; and performing, based on the detected first light emitted along the first axis and on the detected second light emitted along the second axis, a biasing operation that modifies the proportion of the first particle type to the second particle type;

wherein the first light and the second light are fluorescence (i) that results from incidence of the illuminating light on particles in the sample and (ii) that travels in multiple different directions from fluorescing particles in the sample, and wherein the method further comprises:

calculating a kernel within a pixel map;

adding a first instance of the kernel to the pixel map based on the light emitted from the sample along the first and second axes;

adding a second instance of the kernel to the pixel map based on the light emitted from the sample along the first and second axes;

deriving a first histogram from the pixel map;

removing data from the pixel map;

deriving a second histogram from a first row of the pixel map;

generating a first trough point from the second histogram;

deriving a third histogram from a second row of the pixel map;

generating a second trough point from the third histogram;

generating a polynomial function based on the first and second trough points; and bounding a population based on the polynomial function and additional bounding points.

3. A method comprising:

providing, to a microfluidic chip having a sample channel, a sample comprising a particle population having a proportion of a first particle type to a second particle type;

emitting, from a light source, an illuminating light along a first axis such that the illuminating light coincides with particles in the sample as the sample passes through the channel;

detecting, using a first light detector, a first light emitted from the sample along a first axis;

detecting, using the first light detector or a second light detector, a second light emitted from the sample along a second axis; and performing, based on the detected first light emitted along the first axis and on the detected second light emitted along the second axis, a biasing operation that modifies the proportion of the first particle type to the second particle type;

wherein the first light and the second light are fluorescence (i) that results from incidence of the illuminating light on particles in the sample and (ii) that travels in multiple different directions from fluorescing particles in the sample, and wherein the method further comprises:

calculating a kernel within a pixel map;

adding a pre-defined number of instances of the kernel to the pixel map based on the light emitted from a plurality of samples along the first and second axes;

deriving a first histogram from the pixel map along the first axis;

removing data from the pixel map, based on the first histogram;

generating a second histogram from the pixel map along the second axis;

determining an area of interest within the pixel map, based on the second histogram;

generating an additional plurality of histograms along the second axis of the area of interest of the pixel map;

determining a plurality of trough points based on the additional plurality of histograms;

generating a polynomial function based on the plurality of trough points; and bounding a population based on the polynomial function and additional bounding points.

4. The method of claim 1, wherein the first axis is orthogonal to the second axis.

5. The method of claim 1, wherein no more than two detectors are used to detect light emissions from the sample.

6. The method of claim 1, wherein the biasing operation comprises emitting, using a second light source, a third light at the sample to change states of individual particles in the sample.

7. The method of claim 6, wherein the second light is emitted to deactivate a particle in the sample.

8. The method of claim 7, wherein particles in the particle population are cells, and wherein deactivating the cells comprises ablating the cells.

9. The method of claim 7, wherein the illuminating light coincides with the sample at a first location in a path of the sample flowing through the sample channel, and wherein the third light is emitted at the sample so as to coincide with the sample at a second location in the path of the sample, wherein the second location is downstream of the first location.

10. The method of claim 1, further comprising determining an orientational feature of each particle in a set of one or more particles in the sample.

11. The method of claim 10, wherein the orientational feature is determined based on the detected first light and on the detected second light.

12. The method of claim 1, wherein the particle population is a cell population, wherein the first particle type is a first cell type, and wherein the second particle type is a second cell type.

13. The method of claim 12, wherein the first cell type is a male sperm cell with a Y chromosome and the second cell type is a female sperm cell without the Y chromosome.

14. The method of claim 13, wherein the proportion, as modified by the biasing operation, comprises more male sperm cells relative to female sperm cells.

15. The method of claim 1, wherein the biasing operation is performed based on fluorescence detected along the first axis in combination with fluorescence detected along the second axis.

16. The method of claim 1, further comprising generating a histogram of intensity along the first and second axes, and identifying a region in the histogram corresponding with particles of the first type or particles of the second type.

17. The method of claim 16, wherein the first light and the second light are fluorescence of particles in the sample, and wherein the histogram corresponds to fluorescence intensity along the first and second axes.

18. The method of claim 1, wherein the microfluidic chip further comprises an access port via which the second light emitted along the second axis is collected.

19. The method of claim 18, wherein the access port of the microfluidic chip comprises a fiber optic element for transmitting the second light.

20. The method of claim 1, further comprising performing a gating operation based on the detected first light emitted along the first axis and on the detected second light emitted along the second axis.

* * * * *